(12) United States Patent
Alabugin et al.

(10) Patent No.: US 8,334,403 B1
(45) Date of Patent: *Dec. 18, 2012

(54) C-LYSINE CONJUGATES AS PH-CONTROLLED, LIGHT-ACTIVATED REAGENTS FOR DOUBLE STRANDED DNA CLEAVAGE AND ASSOCIATED METHODS

(75) Inventors: Igor Alabugin, Tallahassee, FL (US);
Serguei Kovalenko, Martinez, GA (US);
Wang Yong Yang, Tallahassee, FL (US);
Kerry Gilmore, Tallahassee, FL (US);
Boris Breiner, Cambridge (GB)

(73) Assignee: Florida State University Research Foundation, Inc., Tallahassee, FL (US)

( * ) Notice: Subject to any disclaimer, the term of this patent is extended or adjusted under 35 U.S.C. 154(b) by 151 days.

This patent is subject to a terminal disclaimer.

(21) Appl. No.: 12/640,877

(22) Filed: Dec. 17, 2009

Related U.S. Application Data

(63) Continuation-in-part of application No. 11/615,037, filed on Dec. 22, 2006, now Pat. No. 7,695,912.

(60) Provisional application No. 60/753,156, filed on Dec. 22, 2005, provisional application No. 61/138,162, filed on Dec. 17, 2008.

(51) Int. Cl.
*C07C 229/00* (2006.01)
*C12Q 1/68* (2006.01)
(52) U.S. Cl. .......................................... 562/562; 435/6.1
(58) Field of Classification Search ....................... None
See application file for complete search history.

*Primary Examiner* — Kenneth R. Horlick
*Assistant Examiner* — David Thomas
(74) *Attorney, Agent, or Firm* — Allen, Dyer, Doppelt, Milbrath & Gilchrist, P.A.

(57) ABSTRACT

Compounds and methods for double-stranded DNA cleavage of light-activated lysine conjugates are enhanced at the slightly acidic pH suitable for selective targeting of cancer cells by the presence of two amino groups of different basicities. The first amino group plays an auxiliary role enhancing solubility and affinity to DNA whereas the second amino group which is positioned next to the light-activated DNA-cleaver undergoes protonation at the desired pH threshold. Protonation results in two synergetic effects which account for the increased DNA-cleaving ability at the lower pH: tighter binding to DNA at the lower pH; and the unproductive pathway which quenches the excited state of the photocleaver through intramolecular electron transfer is eliminated once the donor amino group next to the chromophore is protonated. The utility of these molecules for phototherapy of cancer is confirmed by the drastic increase in toxicity of five conjugates against cancer cell lines upon photoactivation.

17 Claims, 46 Drawing Sheets

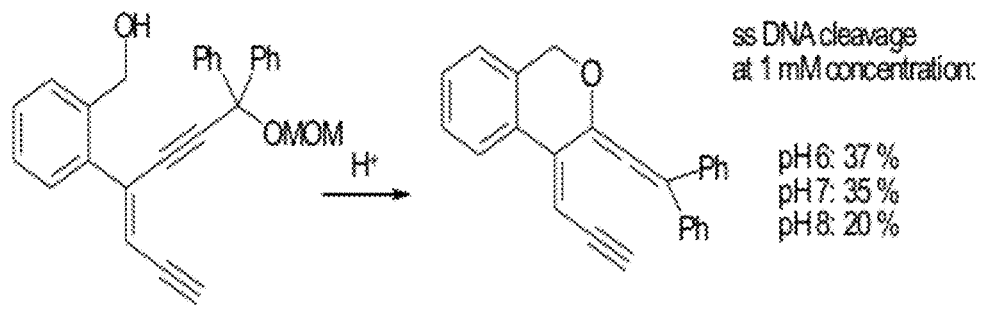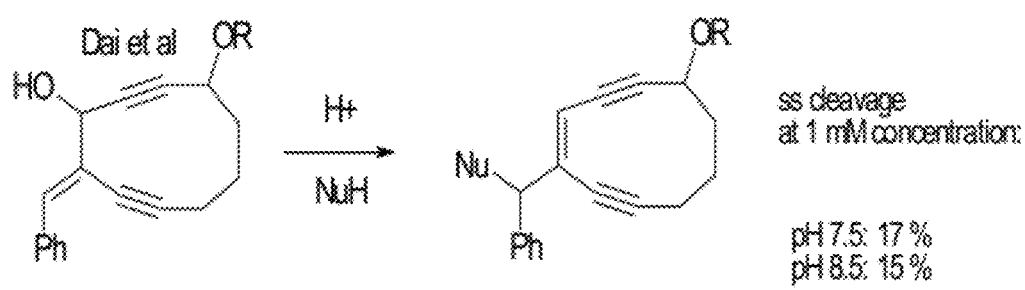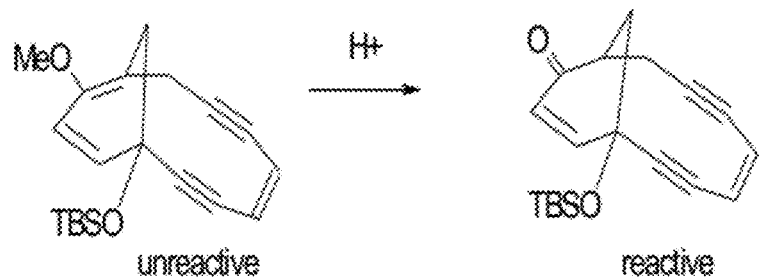
FIG. 1

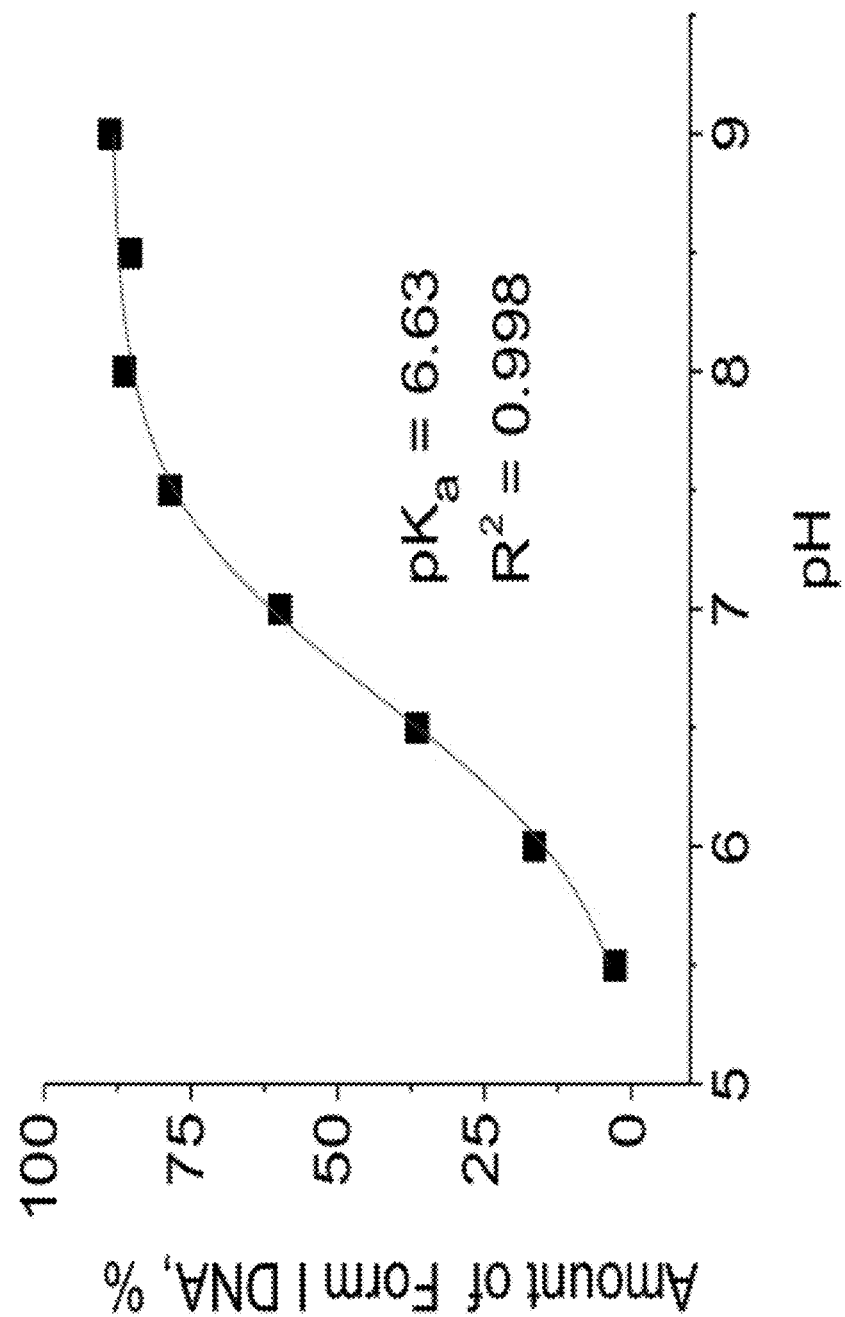
FIG. 7 A: UNREACTED DNA

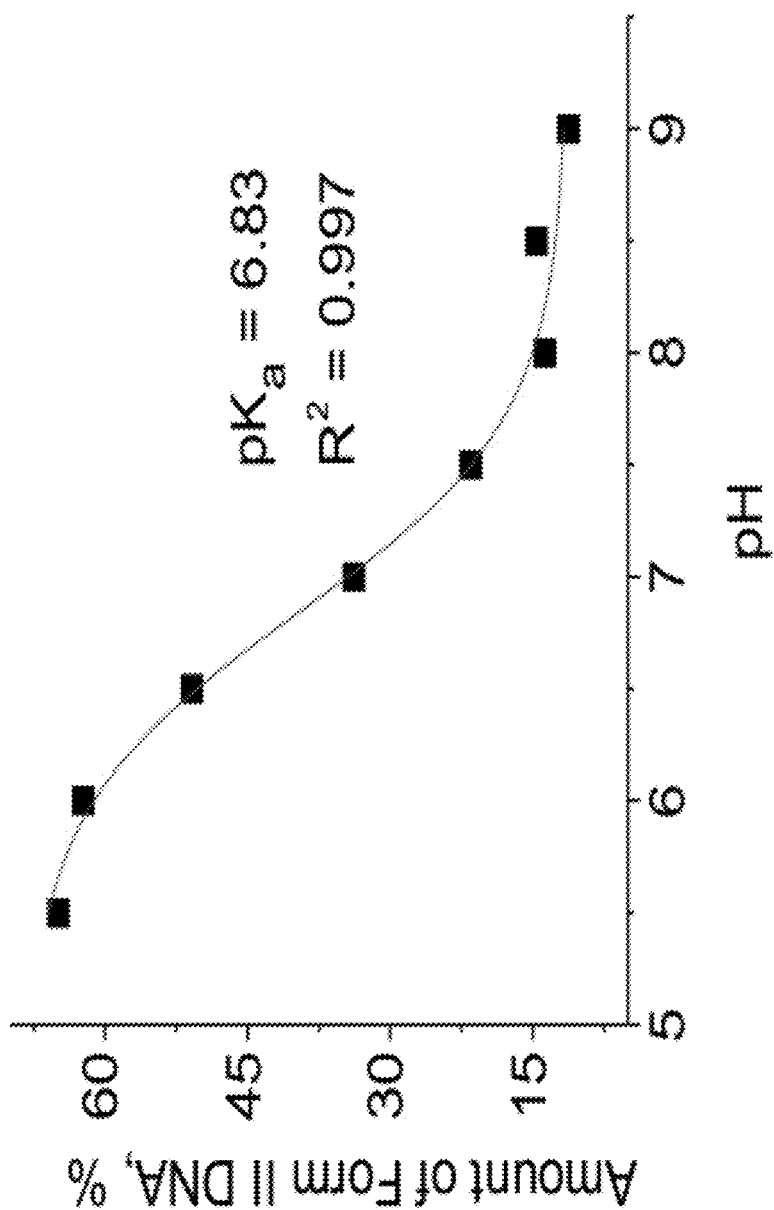
FIG. 7 B: SS-CLEAVAGE

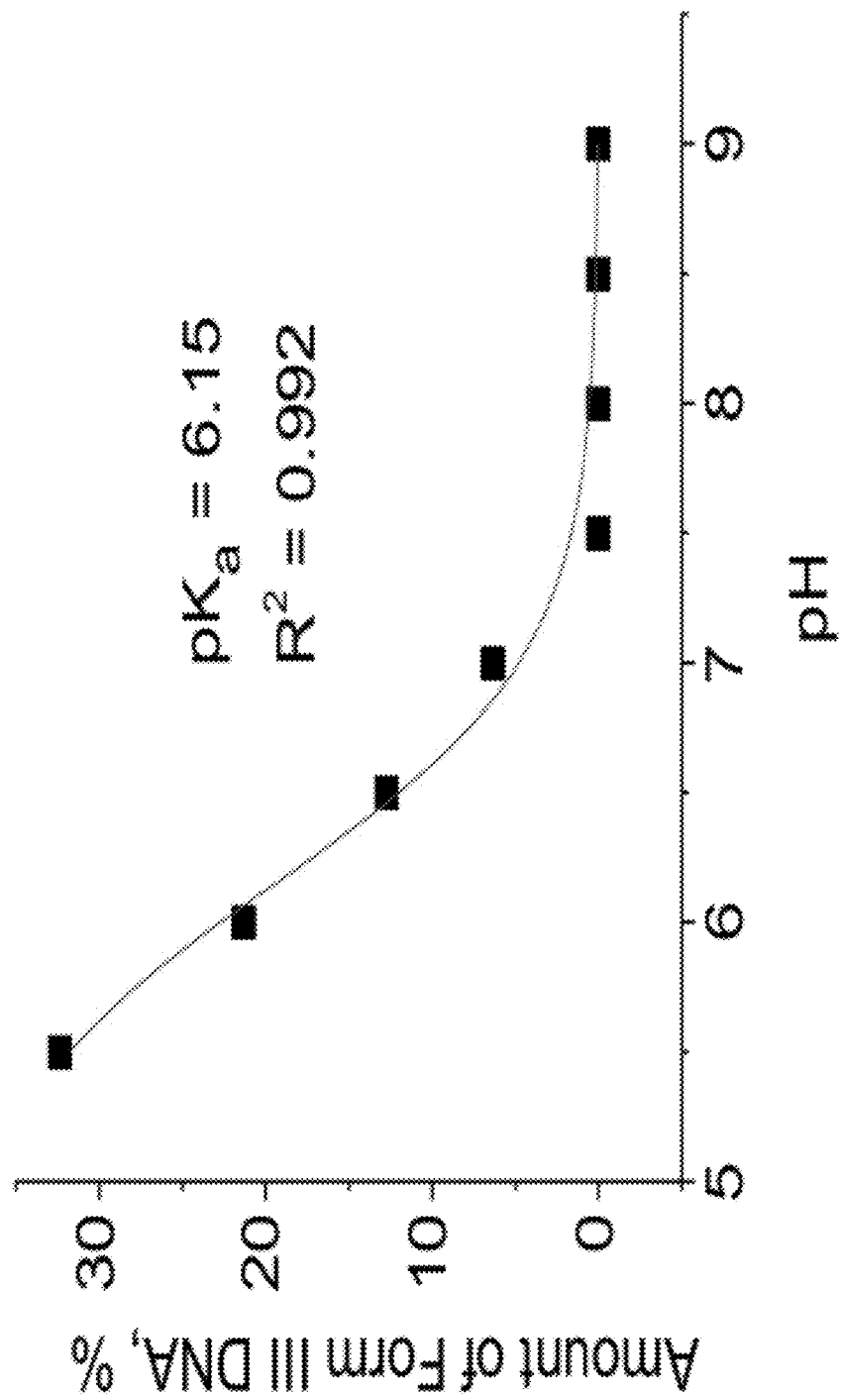
FIG. 7C: DS-CLEAVAGE

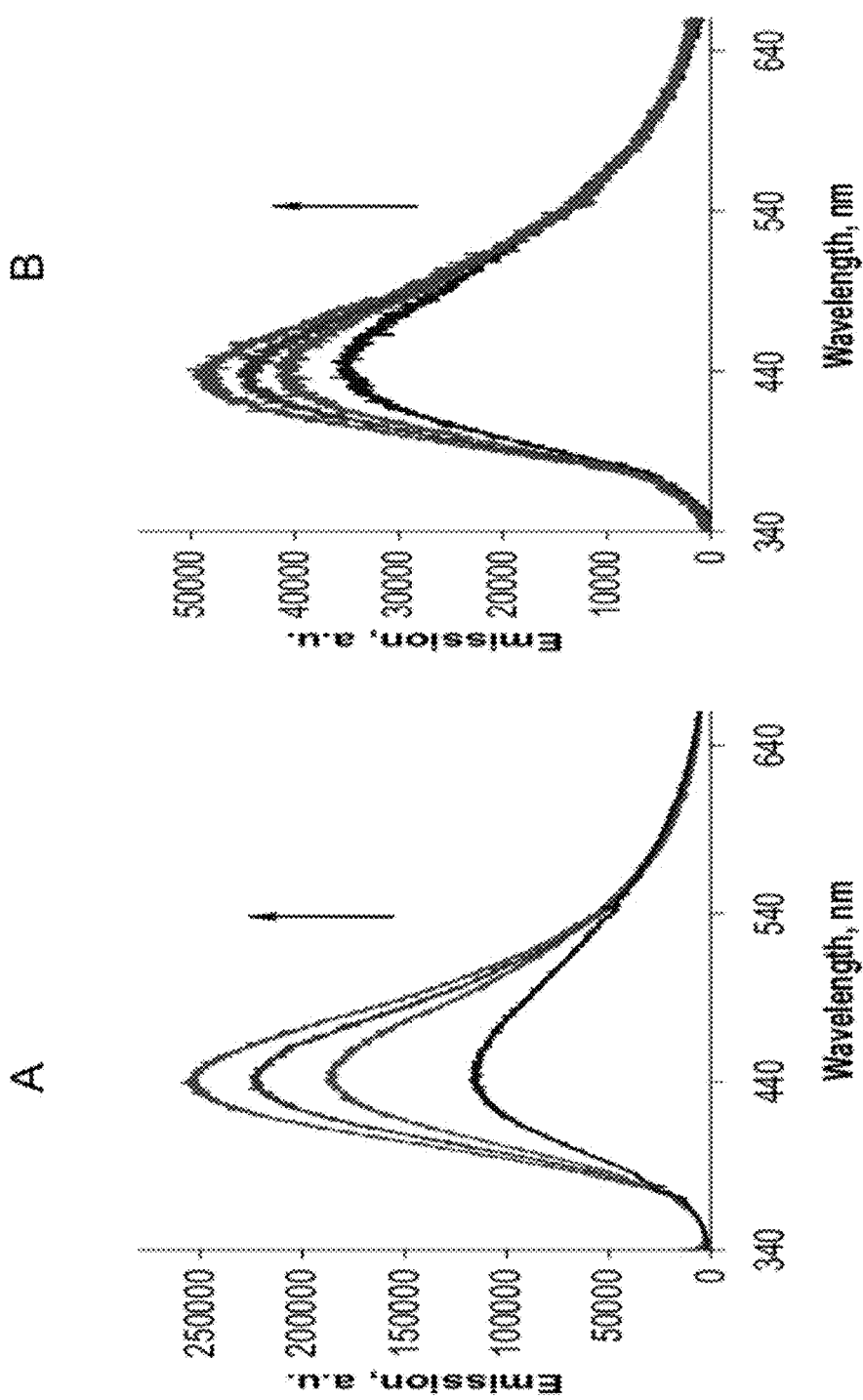
FIG. 17 A-B

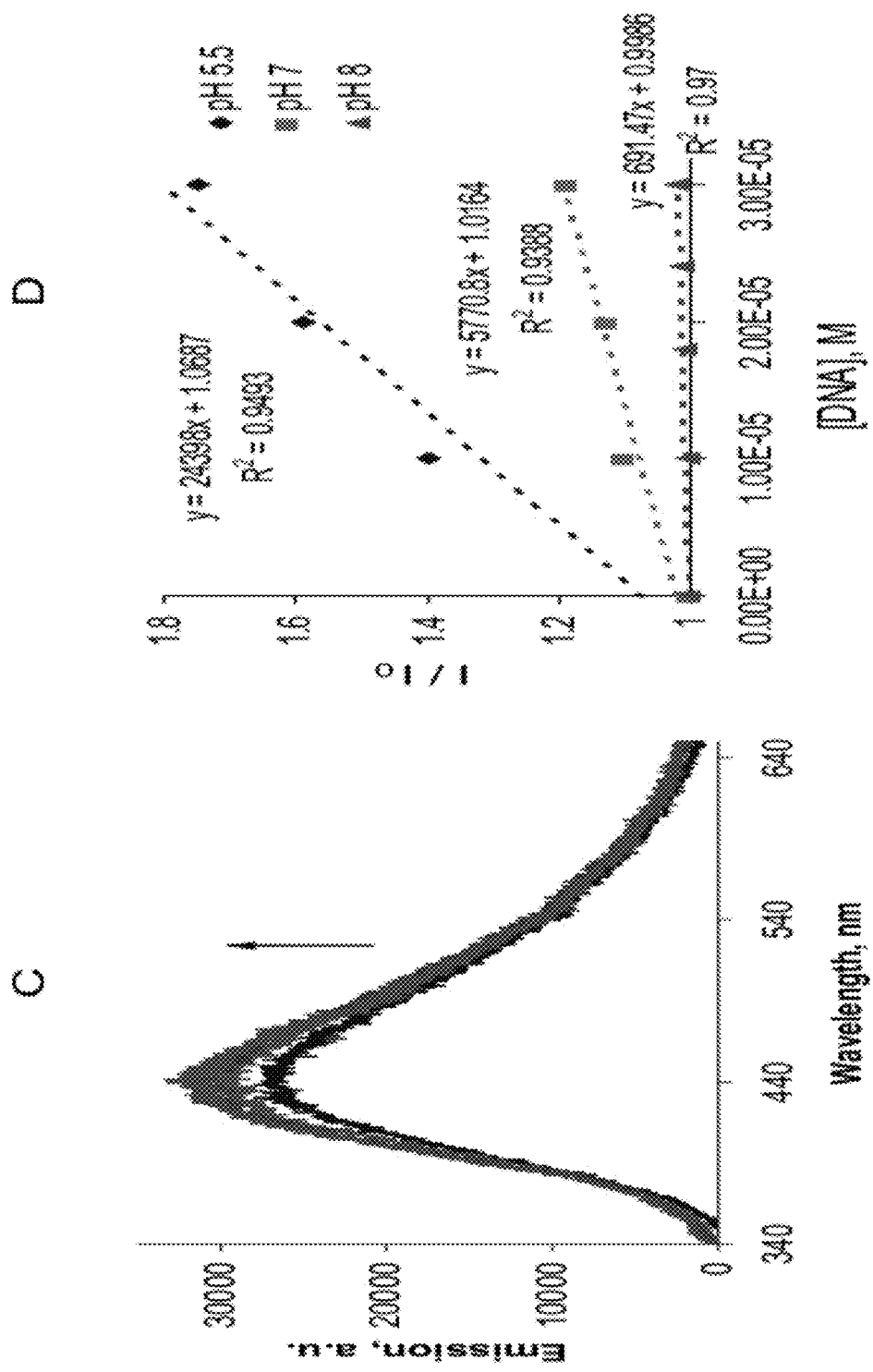
FIG. 17 C-D

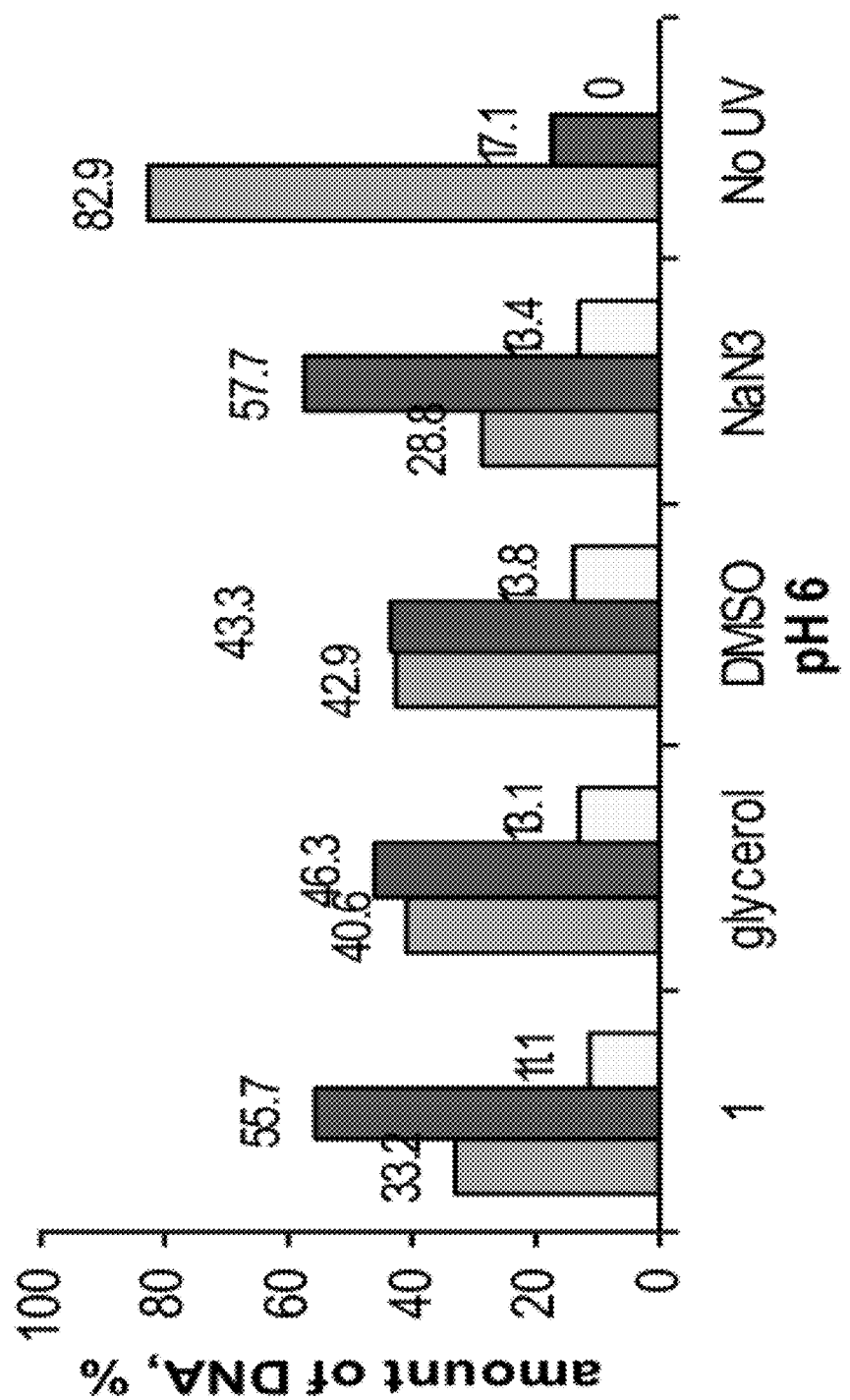
FIG. 21 A1

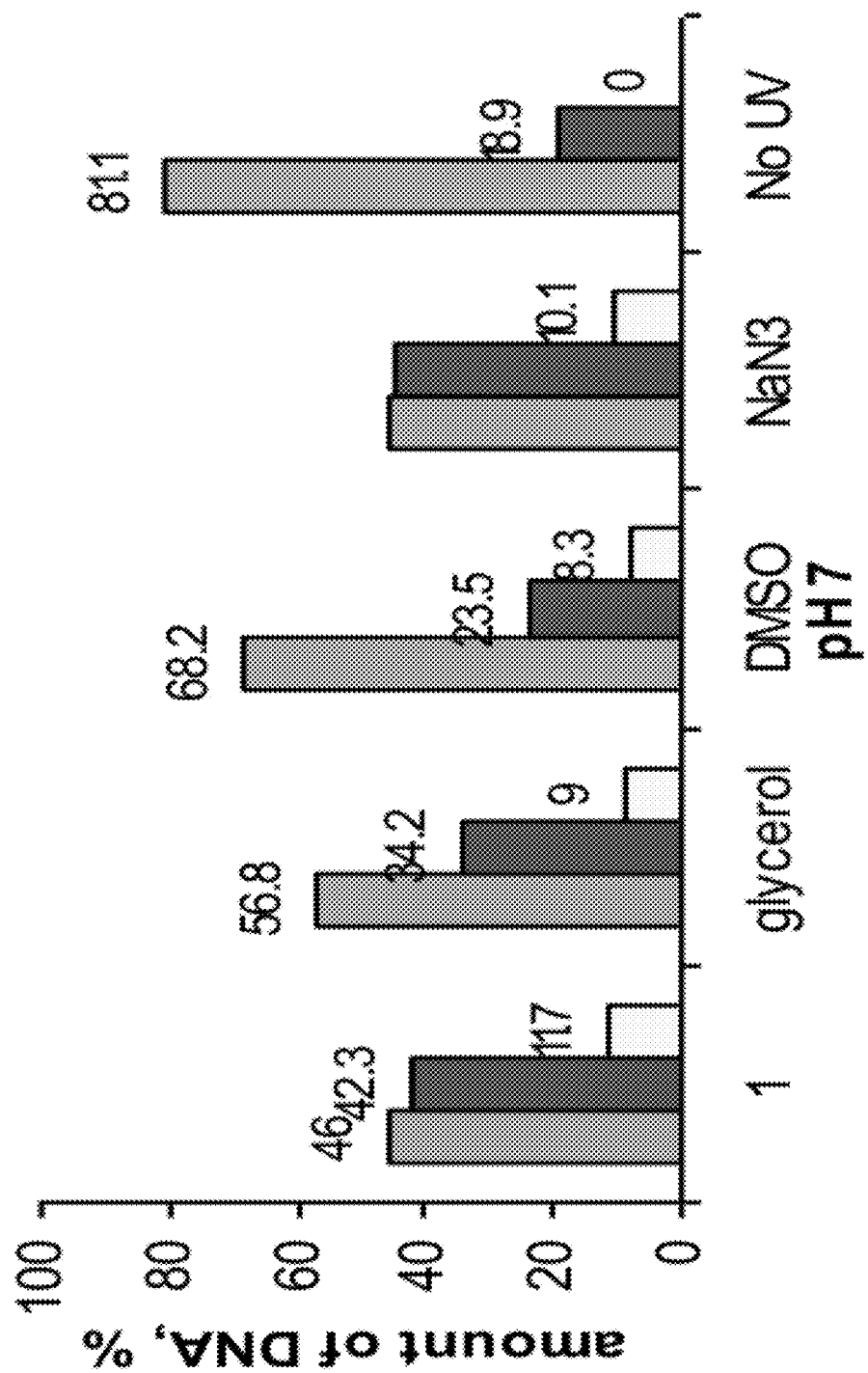
FIG. 21 A2

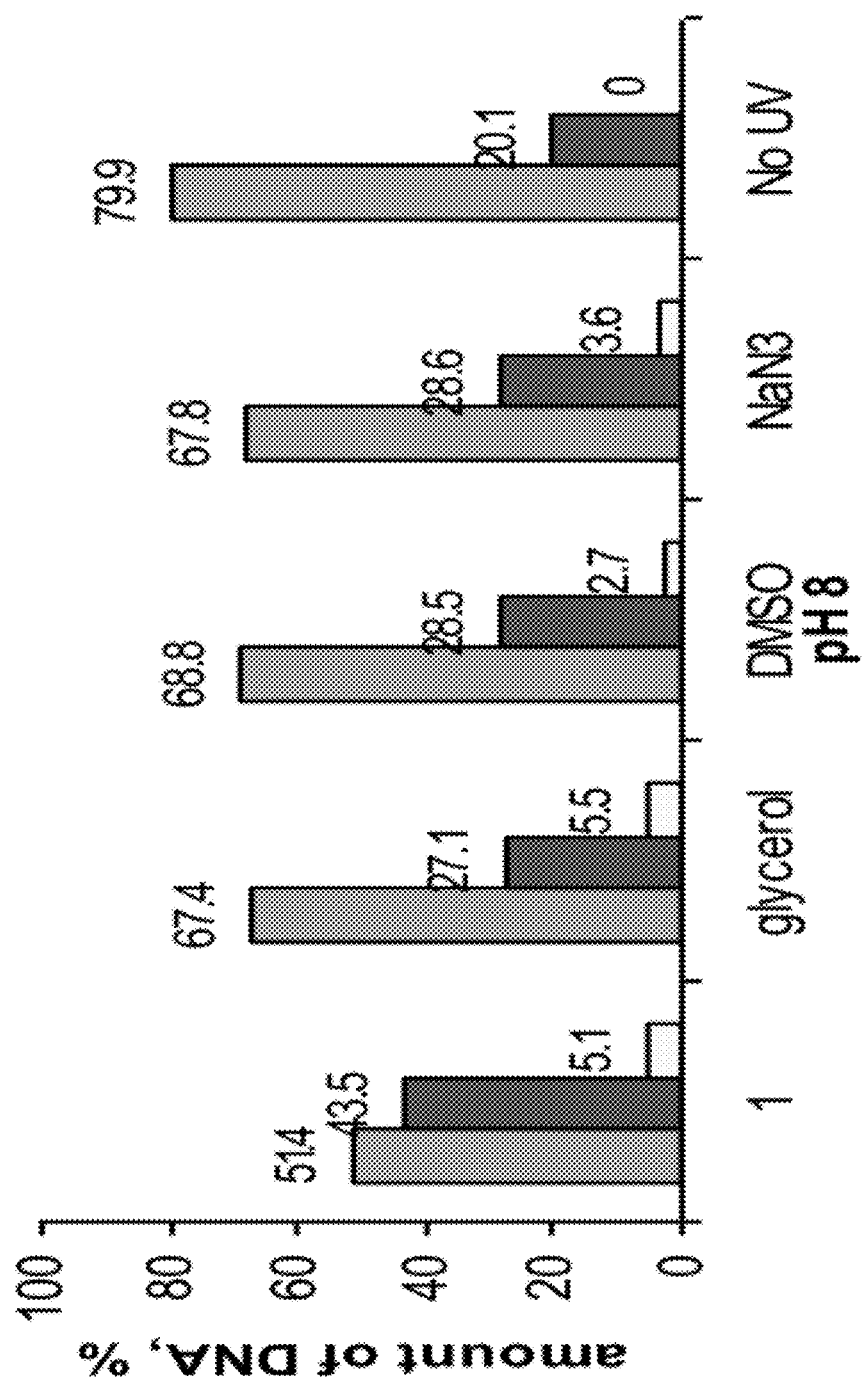
FIG. 21 A3

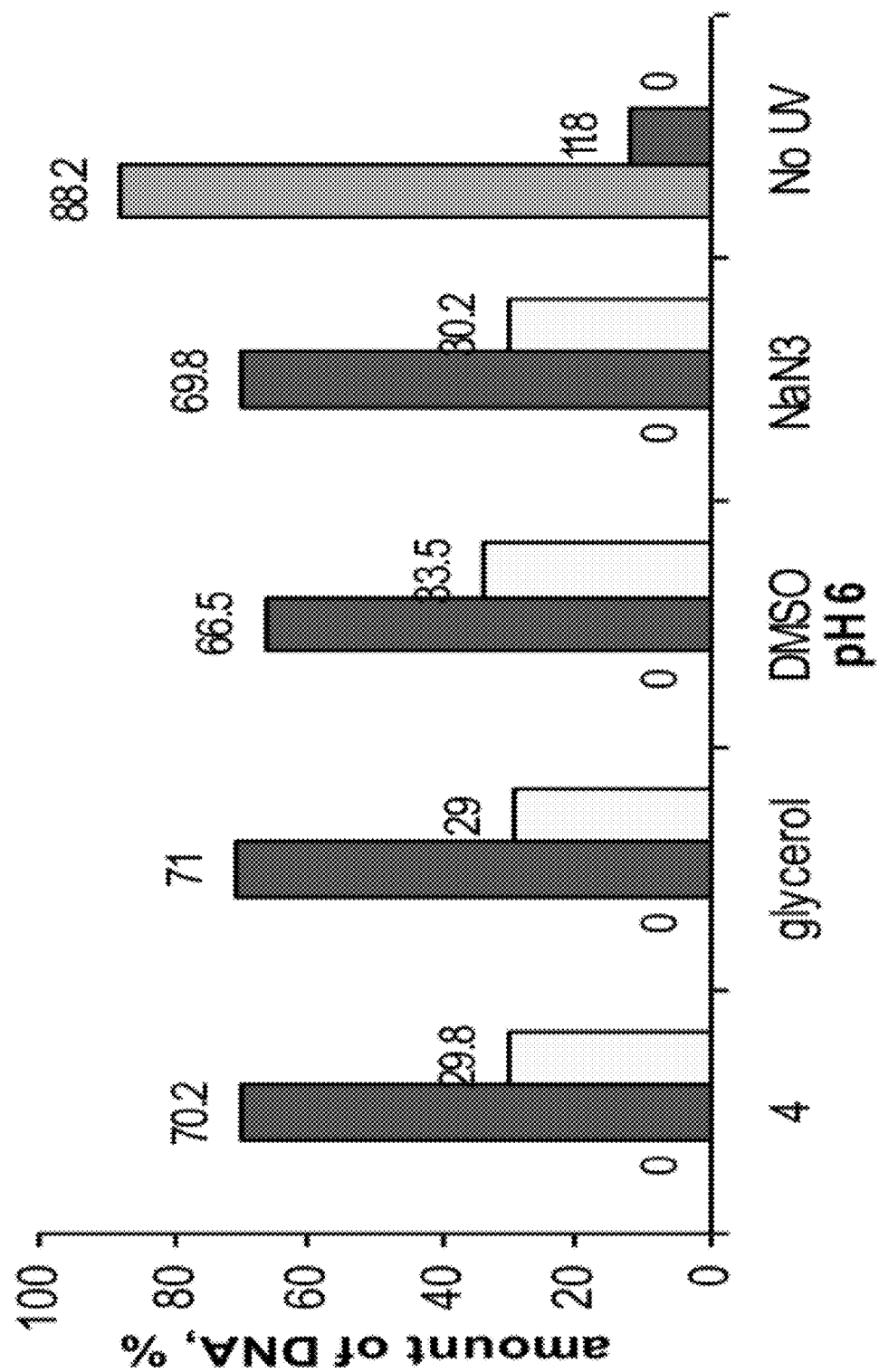
FIG. 21 B1

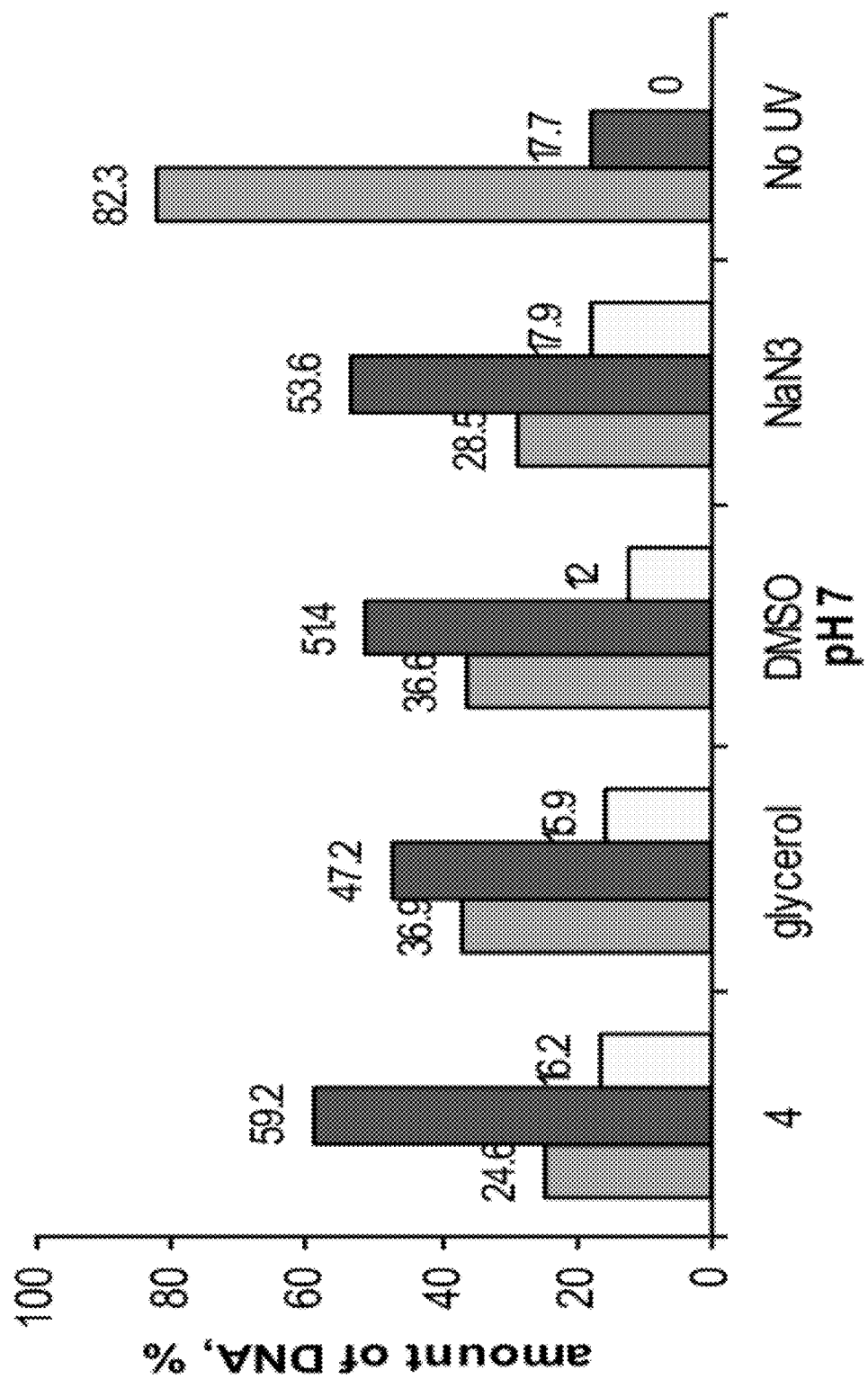
FIG. 21 B2

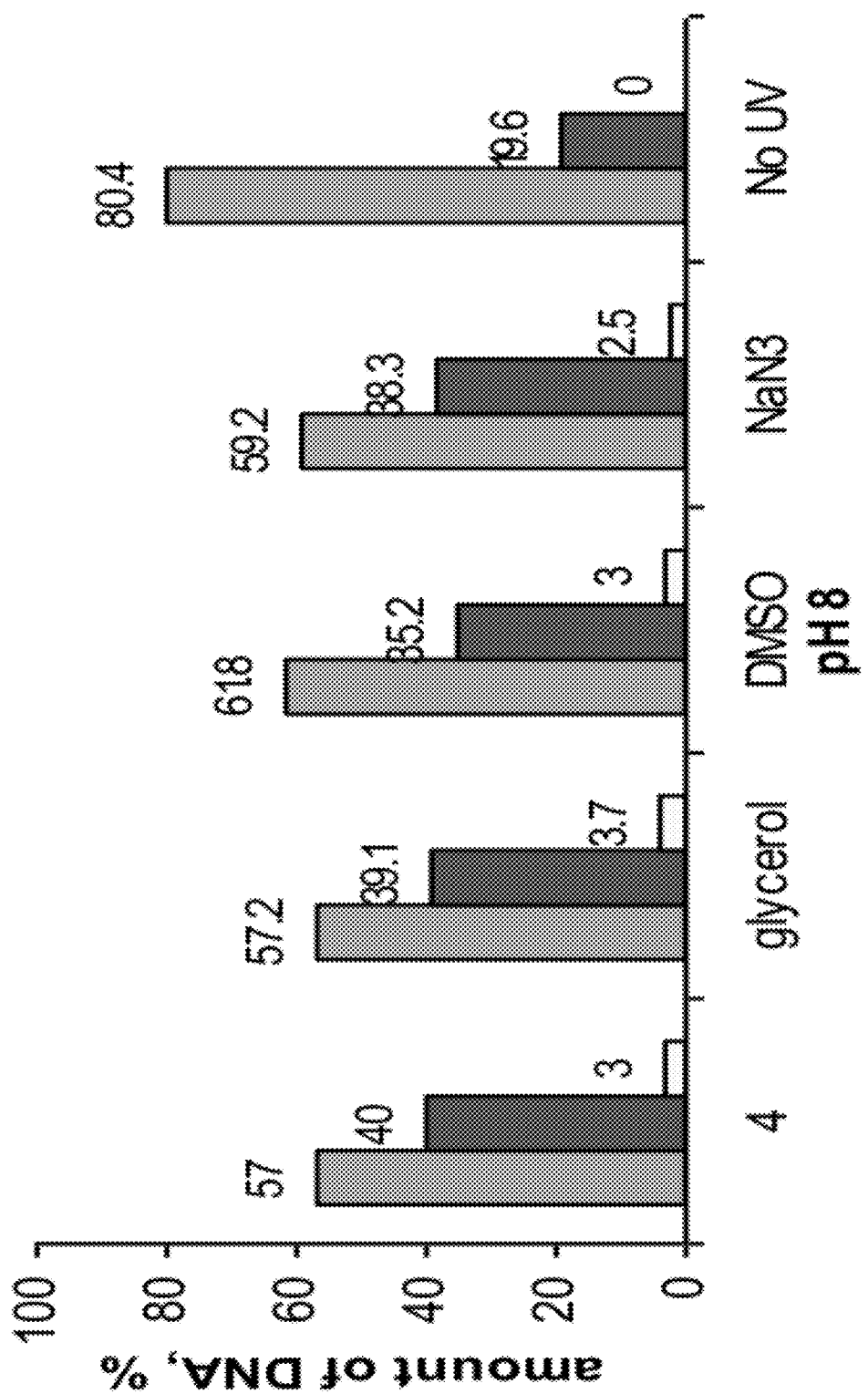
FIG. 21 B3

C-LYSINE CONJUGATES AS PH-CONTROLLED, LIGHT-ACTIVATED REAGENTS FOR DOUBLE STRANDED DNA CLEAVAGE AND ASSOCIATED METHODS

RELATED APPLICATION

This application is a continuation-in-part of application Ser. No. 11/615,037 filed on 22 Dec. 2006, an application which claimed priority to provisional application Ser. No. 60/753,156 filed on 22 Dec. 2005; this application also claims priority from provisional application Ser. No. 61/138,162 filed on 17 Dec. 2008; all said applications being incorporated herein by reference in their entireties.

STATEMENT OF GOVERNMENT RIGHTS

Development of this invention was at least partially supported by a research grant from the U.S. Government. Accordingly, the Government may have certain rights in the invention, as specified by law.

FIELD OF THE INVENTION

The present invention relates to the field of biochemistry of DNA and, more particularly, to compounds effective for pH-controlled, light-activated double-stranded cleavage of DNA and associated methods.

BACKGROUND OF THE INVENTION

Control of chemical reactions becomes especially challenging when chemical processes have to work in the complexity of biological environments. This is one of the reasons why the ability to design molecules with structure, reactivity and biological activity "switchable" via an externally controlled factor continues to draw significant attention, both from the practical and fundamental points of view. Possible applications of such molecules include design of molecular machines and switches, logic gate mimics, optical sensors, drug delivery systems, etc. Since pH-dependent "switchable" molecules are of particular use for processes that occur in biochemical systems and in the environment, interesting pH-sensitive systems were developed to control such diverse phenomena as strand orientation and exchange in peptide assemblies, charge densities in self-assembled monolayers, encapsulation of guests in supramolecular polymers, phase transitions in stimuli-sensitive polymers for drug delivery, rotaxane switching, properties of luminescent devices based on organic fluorophores and metal complexes, permeability of mesoporous materials, growth of nanomaterials, control of recognition-mediated reactions, and the design of bioreactors. Life itself is a pH sensitive phenomenon, as many biochemical processes work only within a very narrow pH window.

In this study, we provide the first example of a "switchable" molecular system for pH-controlled double stranded DNA-cleavage designed for selective targeting of cancer cells. The more acidic extracellular environment of solid tumors, relative to that of the normal cells, results in a pH gradient that has a dramatic effect on drug uptake in tumor cells and can be explored in the design of tumor-specific DNA cleaving agents. It is known that hyperglycemia (e.g., glucose infusion) and/or certain drugs, e.g., amiloride, nigericin, and hydralyzine, are also able to lower the intracellular pH of cancer cells. For example, administration of amiloride and nigericin at dosages that do not affect the normal cells drops the intracellular pH in a number of tumor cell types from 7.2 to 6.2-6.6.'" Moreover, hyperglycemia as well as hypoxia lead to an even further acidification to pH as low as 5.5.'

Although research in this direction has been hampered by the scarcity of suitable pH-dependent cytotoxic agents, a number of approaches can be used for the rational design of such molecules. An illustration of how these ideas can be applied to highly potent class of natural enediyne antibiotics, either through isomerization into more reactive functional groups or through unlocking of structural constraints, is given in FIG. 1. In addition, there have been promising reports of acid-labile drugs that either hydrolyze at lower pH to give toxic products or produce free radicals due to accelerated Co—R bond homolysis. An interesting recent finding involves acid-promoted DNA cleavage by natural antibiotic Varacin C. The authors found a two-fold increase in the extent of single stranded (ss) DNA cleavage at pH 5.5 (47% at 5 µM antibiotic loading) compared with that at pH 7 (23%). Unfortunately, this increase only applies to the ss damage which is, unlike the double stranded (ds) damage, usually repairable by the cell chemical machinery.

Another approach to pH-regulated DNA-cleaving agents involves protonation of basic functional groups. Amine functionality is one of the obvious choices and several elegant experimental designs based on the protonation of this functional group have appeared in the literature (FIG. 2). In particular, the groups of Kerwin, Chen, and Kraka & Cremer reported systems where protonation increased the efficiency of radical damage through simultaneous acceleration of the H-abstraction step and deceleration of p-benzyne diradical deactivation through the retro-Bergman ring opening. After detailed computational studies indicated that properly positioned cationic groups decrease the activation barrier for the Bergman cyclization, Basak and coworkers pursued an alternative approach based on a significant acceleration of the cycloaromatization step imposed by a spatially close ammonium moiety.

Unfortunately, simple aliphatic amines are too basic for the change in the protonation state to occur at the pH window necessary for targeting hypoxic cancer cells. As the result, even when protonation has been shown to accelerate the Bergman cyclization of enediynes, the change in reactivity did not occur in the optimal pH-range. Nevertheless, the basicity of nitrogen bases can be controlled in a number of ways and, thus, the above is not insurmountable. For example, anilines are significantly less basic than aliphatic amines and can be fine-tuned through substitution to accept the proton only at the desired pH-range. Amides, suggested by Chen, and aldimines designed by Kraka and Cremer may offer an excellent solution for fine-tuning the nitrogen basicity.

SUMMARY OF THE INVENTION

With the foregoing in mind, the present invention advantageously describes the development of the first pH-controlled system capable of inducing the much more therapeutically important double-stranded (ds) DNA cleavage. Several challenges presented themselves at the beginning of this study. First, the change in reactivity has to occur at a relatively narrow and predefined pH point (ideally ~pH 7). Second, an efficient DNA-cleaver was needed which could operate within the physiological pH range and be attached to a pH-sensitive functionality without sacrificing its potency.

In order to solve the first problem, we utilized a simple but, to the best of our knowledge, new strategy for the design of pH-regulated molecules which is based on the presence of two amino moieties (or related functional groups) with different basicities. The first amino group should be sufficiently basic to be protonated at a wider range of physiological conditions. This auxiliary group plays three roles through a) enhancing solubility of the conjugates in water, b) increasing their affinity to the negatively charged backbone of DNA, and c) modulating the basicity of the pH-trigger. The pH-trigger itself corresponds to the second amino group which should enable pH-switchable behavior at the desired pH range.

The bifunctional pH-regulated part in our design is derived from a diamino carboxylic acid (lysine) which is connected to the DNA-cleaving moiety through the carboxyl group of lysine (FIG. 3). This mode of attachment is different from the most common way of lysine incorporation into conjugates or proteins through the formation of a peptide bond at the expense of the α-amino group. Importantly, the use of the carboxyl group for the assembly preserves the two amino groups, both of which are essential for solubility, binding to DNA and pH-regulation of DNA-cleavage.

The auxiliary amino group is at the remote terminus whereas the pH-switchable amine is next to the carbonyl group. We were interested in determining whether the presence of a highly polarized acceptor moiety can differentiate the basicities of the two amino groups to the extent where distinct protonation states exist at biologically relevant pH regions (FIG. 4). If this approach is successful, sequential protonation of these groups at different pH can be used to control the photophysical properties of such molecules, their binding to DNA and, ultimately, the efficiency of ds DNA cleavage.

The pH-activated part was combined with light-activated DNA-cleavers in order to take advantage of the high degree of spatial and temporal controls over reactivity inherent to the photochemical activation. We based the choice of the photochemically activated DNA part on our earlier discovery of the C1-C5 cyclization of enediynes which results in the net transfer of four hydrogen atoms to the enediyne moiety.' In particular, the tetrafluoropyridine (TFP) substituted enediynes were found to be both photochemically and thermally stable, unless photoexcitation occurs in the proximity of a suitable electron donor, such as DNA. We have recently shown that these molecules are efficient reagents for the double-strand (ds) DNA photocleavage and that they are amenable to two-photon activation. We have also shown that the lysine conjugates of enediynes, as well as related fulvenes and acetylenes, perform guanosine-specific (oxidative) cleavage at the ends of AT-rich sequences of DNA. After a serendipitous discovery of the photochemical removal of the terminal radioactive label from $^{32}$P-labelled oligonucleotides suggested that the lysine conjugates are capable of recognition of terminal phosphate groups, we utilized this phenomenon for the design of reagents which can recognize the DNA-damage sites (nicked or gapped ss cleavage). These reagents allowed for the first time to achieve a controlled photochemical transformation of the easily repairable ss DNA cleavage to the much more therapeutically important ds cleavage.

These considerations guided our design and prompted us to investigate DNA-cleavage activity and binding to DNA of five lysine conjugates 1-5 in the range of pH 5.5-8 which can be used to differentiate between cancer and healthy cells (FIG. 5). After testing whether the pH-dependent DNA cleavage based on this molecular design is feasible, this paper will concentrate on mechanistic basis of this phenomenon through a combination of photophysical techniques, NMR titrations, analysis of DNA binding trend and effect of chemical additives on the cleavage efficiency.

Accordingly, in its various embodiments, the present invention includes a lysine conjugate selected from the group consisting of compounds having a structure according to formula 1, formula 2, formula 3, formula 4 and formula 5. Additionally the invention includes a method for producing double-stranded DNA cleavage. This method includes contacting a double-stranded DNA molecule having one or more single-stranded nicks at a pH between approximately 5.5 and 8 with the lysine conjugate of claim 1; and irradiating with ultraviolet light.

An additional aspect of the invention includes a method of increasing efficiency of double-stranded DNA cleavage, the method comprising contacting a double-stranded DNA molecule with a lysine conjugate selected from the group consisting of formula 1, formula 2, formula 3, formula 4 and formula 5, in a physiologically acidic environment; and irradiating the contacted DNA with ultraviolet light. In the method the physiologically acidic environment preferably comprises approximately pH 5.5 to 7. In the method irradiation with ultraviolet light is preferably, but not exclusively, carried out at approximately 350 nm.

The invention also includes a method of inhibiting a mammalian cell, the method comprising contacting the cell with the lysine conjugate of claim 1; binding the lysine conjugate with the cell's double-stranded DNA at a pH between approximately 5.5 and 8; and irradiating the cell with ultraviolet light to photochemically activate the bound lysine conjugate to cause a double-stranded cleavage in said DNA. Preferably, in this method the mammalian cell is a human cell, and most preferably the mammalian cell is a human cancer cell.

The invention further includes a method of inhibiting a human cancer cell, the method comprising contacting the cell's double-stranded DNA with a lysine conjugate having a structure selected from formulas 1-5; and irradiating the cell with ultraviolet light. Contacting is preferably effected at between approximately pH 5.5 and 8 and UV irradiation is preferably at approximately 350 nm.

Those of skill in the art will recognize that the invention includes a method of controlling electron transfer from DNA to a photochemical cleaver compound. This method comprises functionalizing the photochemical cleaver compound by attaching thereto a pH-sensitive functional chain or ring having one or more amino groups of sufficient basicity; protonating the one or more amino groups of the photochemical cleaver at a physiologically acid pH; binding the protonated photochemical cleaver to double-stranded DNA; and irradiating the bound protonated photochemical cleaver with ultraviolet light, whereby one or more electrons are transferred from the DNA to the bound protonated photochemical cleaver to thereby cause damage to the DNA.

In this last given method, the functionalized photochemical cleaver compound is a compound according to formulas 1-5. In this method binding comprises having the functionalized photocleaver compound preferably positioned adjacent a single-strand nick in the DNA. As noted above, the physiologically acid pH comprises from approximately pH 5.5 to approximately pH 7.0. The method may be carried on cells, so that the DNA is intracellular.

Accordingly, the presently disclosed invention in its various embodiments discloses molecules, functionalized photochemical cleavers of DNA, which are capable of switching from low efficiency cleaving to high efficiency cleaving, the switch being responsive to the pH of the reaction environment. Additionally, the pH change may be used to differentiate between healthy cells typically near a neutral pH and hypoxic cancer tissues which typically exhibit a physiologically acidic pH between approximately 5.5 and 7.

BRIEF DESCRIPTION OF THE DRAWINGS

Some of the features, advantages, and benefits of the present invention having been stated, others will become apparent as the description proceeds when taken in conjunction with the accompanying drawings, presented solely for exemplary purposes and not with intent to limit the invention thereto, and in which:

FIG. 1 shows approaches to pH-activated enediynes based on acid-catalyzed transformations of unreactive prodrugs, according to an embodiment of the present invention;

FIG. 7 shows the percentage of unreacted DNA (Form I), single-stranded cleavage (Form II) and double-stranded cleavage (Form III) as a function of pH, and the apparent $pK_a$ values corresponding to these plots;

FIG. 17 illustrates emission titrations of 4 (10 µM) in 20 mM phosphate buffer with 0, 10, 20, 30 µM of CT DNA at pH 5.5 (a), pH 7 (b) and pH 8 (c); the initial slopes of plots illustrating changes in fluorescence of 4 as a function of DNA concentration (d);

FIG. 21 six bar graphs show the effects of hydroxyl radical/singlet oxygen scavengers (10 mM) upon the efficiency of DNA cleavage at pH 6, 7 and 8 by conjugates 1 (a) and 4 (b) after 5 min. irradiation; color coding: light blue—Form I, dark purple—Form II, light yellow—Form III;

DETAILED DESCRIPTION OF THE PREFERRED EMBODIMENT

Figure 2:
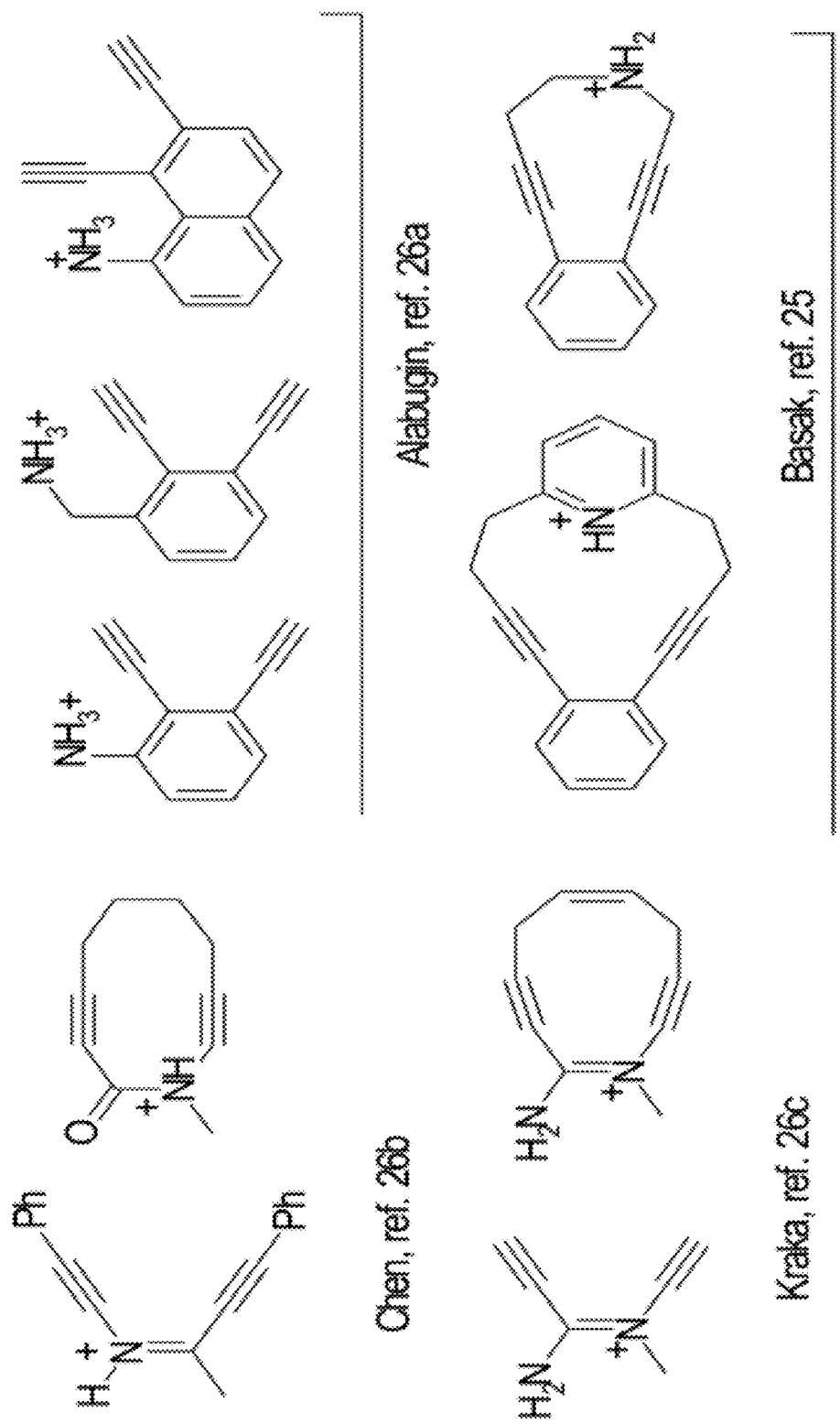
FIG. 2 depicts literature examples of pH-controlled amino enediynes.
Figure 3:
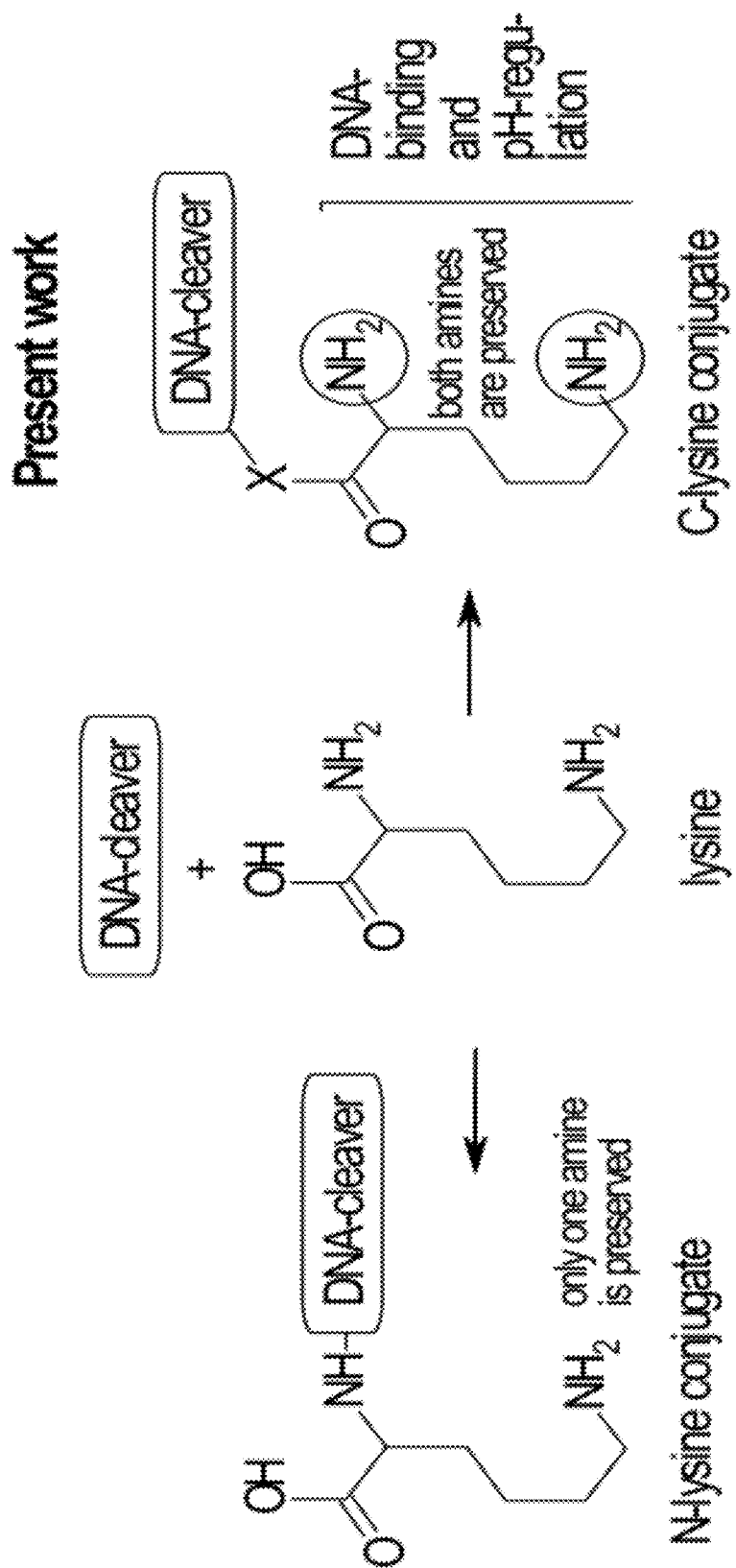
FIG. 3 illustrates two types of lysine conjugates.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control.

In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

This invention, along with extensive experimental support therefor, was published in J. Am. Chem. Soc., 2009, 131 (32), pp. 11458-11470. This scientific peer-reviewed article was first published on the web on 28 Jul. 2009 and is incorporated herein by reference in its entirety.

Materials and Methods.

General information. $^1$H, $^{13}$C and $^{19}$F NMR were collected on a Varian Gemini 300 MHz NMR spectrometer and a Bruker 300 MHz NMR spectrometer. Mass spectrometry data was collected on a Jeol JMS-600H. UV spectra were recorded on a Shimadzu UV-2100. Fluorescence spectra were obtained with SPEX FluoMax spectrofluorimeter using right-angle geometry. pH was adjusted with AB 15 plus pH meter (Accument) after standardization at 25° C. All buffers were prepared and pH-adjusted at room temperature (25° C.).

Plasmid DNA Photocleavage. pBR322 plasmid DNA (4,361 b/p; from BioLabs Inc., 1 μg/μL solution in 10 mM Tris-HCl (pH 8.0), and 1 mM EDTA buffer) was diluted to a concentration of 0.01 μg/μL. The solution containing cleavage agent, DNA (30 μM/bp) in 20 mM sodium phosphate buffer was incubated for 1 hour at 30° C. Samples were placed on ice at a distance of 20 cm from 200 W Hg—Xe lamp (Spectra-Physics, Laser & Photonics Oriel Instruments with long pass filter with 324 nm cut-off wavelength).

Electrophoretic Analysis. The gel electrophoresis was carried out in 1×TBE buffer at 80 V using Miligel FisherBiotech Horizontal Electrophoresis System. All gels were run on 1% agarose slab gels. Before loading, the DNA samples were mixed with 0.33 volume of tracking dye containing bromophenol blue (0.25%) and glycerol (30%) in water. After staining in ethidium bromide solution (2 μg/ml) for 1 hour, the gel was washed with water and pictures were taken with Polaroid 3000$_{ISO}$ type 667 film. The relative quantities of the supercoiled, nicked, and linear DNA were calculated by integrating the "area" of each spot by the image analyzer software Total/Lab (Nonlinear Dynamics Ltd., UK). The amount of supercoiled DNA was multiplied by factor of 1.4 to account for reduced ethidium bromide intercalation into supercoiled DNA.

pH titration by $^1$H-NMR. pH* of compound 8 (3 mM) solution in D$_2$O containing 0.05 wt % 3-(trimethylsilyl)propionic-2,2,3,3-d$_4$ acid, sodium salt (TSP-d$_4$) was adjusted with 10 wt % DCI and NaOD in D$_2$O at 25° C. under argon purged condition.

Spectrometric determinations of pK$_a$. pH of 10 μM of compound solution in H$_2$O was adjusted with 10, 100 mM HCl (aq) and NaOH (aq) solution under argon purged condition. Excitation wavelength was 330 nm and polymethacrylate fluorimeter cuvettes were used.

Absorbance and fluorescence titration with DNA. The concentrations of calf thymus DNA stock solution was determined spectophotometrically using the following molar absorptovity values: $1.32 \times 10^4$ M$^{-1}$ cm$^{-1}$ (per base pair) at 260 nm. All experiments were done in 20 mM sodium phosphate buffer at 25° C. and polymethacrylate fluorimeter cuvettes were used. The same amount of DNA was added to both sample and reference cuvettes during UV/Vis titration.

Determination of excited state lifetimes. The concentration of compound solution was 10 μM in 20 mM sodium phosphate buffer. The photoluminescence lifetime measurements were conducted by exciting the samples with the output of a Nd:VO_4 (Spectra-Physics Vanguard, 2 W, 532 nm, 76 MHz, 10 ps) pumped R6G dye laser (Coherent 702-1). The output of the dye laser (600 nm, Rhodamine 6G) was cavity dumped at 1.9 MHz and frequency doubled using a BBO crystal to excite the fluorophore (the excitation wavelength used was 290 nm). Samples were excited with <1 mW power and the emission was collected at right angles onto a Chromex S3 500 is 0.5 m imaging monochromator with a 50 g/mm grating and 0.5 nm resolution. Output of the monochromator is focused into a Hamamatsu C5680 streak camera operating at a 20 ns window for the fluorophore. Intensity analysis was carried out by integrating the spectral profile in time on the streak camera. Lifetime analysis over 6-7 lifetimes of the fluorophore was conducted by binning the photoluminescence intensity collected on the streak camera over a 20 nm spectral window at the centroid value of the emission of the fluorophore.

Ethidium bromide displacement. The concentrations of stock solutions of calf thymus DNA and ethidium bromide were determined spectophotometrically using the molar absorptovity values: $1.32 \times 10^4$ M$^{-1}$ cm$^{-1}$ at 260 nm; $5.60 \times 10^3$ M$^{-1}$ cm$^{-1}$ at 480 nm. The solutions of 10 μM ethidium bromide and CT DNA in 20 mM sodium phosphate buffer were tested by adding 1.5 μL of compound 1 solution (1 mM) each time. The experiments were carried out at 26° C. and polymethacrylate cuvettes were used. Emission was measured 10 min. after addition of compound to get the equilibrium.

LNCap cell proliferation assays. LNCap cells (P.35) were plated in 24-well plates at a density of 20,000 cells/well, and were maintained in RPMI 1640 medium supplemented with 5% FBS, sodium bicarbonate (2 g/L) and penicillin ($10^2$ U/mL), and streptomycin ($10^2$ mg/mL). Compound 4 was dissolved in serum free RPMI 1640 medium supplemented with sodium bicarbonate (2 g/L), penicillin ($10^2$ U/mL), and streptomycin ($10^2$ mg/mL). A serial dilution was made. The concentration of the compound used to treat the cells include: 0.01 μM, 0.1 μM, 0.3 μM, 1 μM, 3 μM, 10 μM, and 30 μM. On the third day, the cells were washed with PBS (phosphate buffered saline). Thereafter, the RPMI 1640 medium containing compound 4 were added to the cells, 4 wells for each compound concentration. The cells placed in the incubator for 4 h. After 4 h had elapsed, the cells were exposed to UV with plate covers removed for maximum exposure for 10 minutes. After UV exposure, the medium containing the compound was replaced with regular medium and the cells were returned to the incubator for 48 h. The cells were trypsinized and counted.

Synthesis of compounds. All reagents used were obtained from commercial sources and were of the highest grade available. The synthesis of compounds 1 and 2 was described previously by Kovalenko, S. V.; Alabugin, I. V., *Chem. Commun.* 2005, 1444, a publication which is incorporated herein by reference in its entirety.

Figure 25:
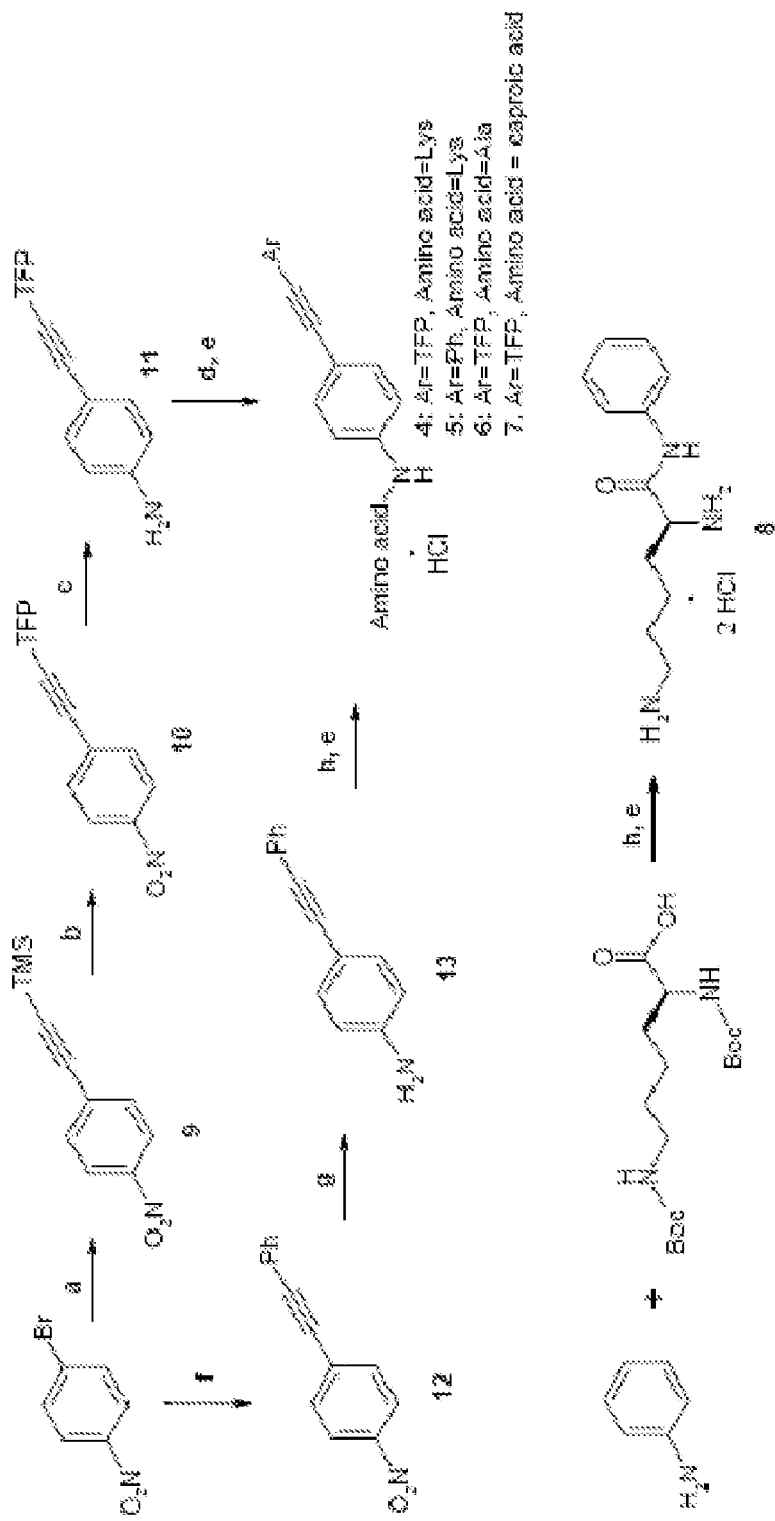
FIG. 25 shows a synthetic scheme for compounds 4-8.

Scheme 1. Synthesis of compounds 4, 5, 6, 7 and 8, as shown in FIG. 25. Reagents and conditions: (a) TMSCCH, PdCl$_2$(PPh$_3$)$_2$, CuI, (i-Pr)$_2$NH, reflux, 12 h; (b) C$_5$F$_5$N, CsF, DMF, 24 h, rt; (c) SnCl$_2$, HCl(aq), THF; (d) N-Boc-amino acid, POCl$_3$, pyridine, −20° C.; (e) HCl(g), THF (or MeOH); (f) PhCCH, PdCl$_2$(PPh$_3$)$_2$, CuI, Et$_3$N; (g) FeSO$_4$, MeOH/H$_2$O, reflux; (h) Boc-Lys(Boc)-OH, DCC, HOBT (or DMAP), CH$_2$Cl$_2$.

4-(Trimethylsilylethynyl)nitrobenzene (9). A mixture of p-bromonitrobenzene (2.02 g, 10 mmol), bis(triphenylphosphine)palladium(II) chloride (0.2 g, 0.3 mmol), and copper(I) iodide (0.05 g, 0.3 mmol) in 40 ml of N,N-diisopropylamine was degassed by freeze/pump/thaw technique (three times). Trimethylsilylacetylene (1.2 g, 12 mmol) was added and the mixture was refluxed for 12 hours. The amine was removed by rotary evaporation, and then the residue was dissolved in $CH_2Cl_2$ and washed with water. The organic layer was dried ($Na_2SO_4$), filtered, and concentrated. The residue was purified by column chromatography (EtOAc/hexanes, 1:10) to afford 4-(trimethylsilylethynyl)nitrobenzene (1.53 g, 70%). All spectral data were analogous to the literature data. Takahashi, S; Kuroyama, Y; Sonogashira, K; Hagihara, N. *Synthesis*, 1980, 627.

4-(2,3,5,6-Tetrafluoropyridin-4-ylethynyl)nitrobenzene (10). A solution of 4-(trimethylsilylethynyl)nitrobenzene, 9 (0.95 g, 4.3 mmol) in DMF (10 mL) was added to the mixture of pentafluoropyridine (0.73 g, 4.3 mmol) and CsF(1.0 g, 6.5 mmol, 1.5 eq.) in DMF (10 mL) for 4 h using syringe pump. The reaction mixture was stirred constantly throughout addition. Water (20 mL) and dichloromethane (50 mL) were added. Organic phase was separated, washed with aqueous ammonium chloride solution. Solvent was evaporated. The residue was chromatographed (EtOAc/hexanes, 1:15) to provide 4-(2,3,5,6-tetrafluoropyridin-4-ylethynyl)nitrobenzene as a slightly yellow solid (0.77 g, 60%): m.p. 155-158° C.; $^1$H-NMR (300 MHz, $CDCl_3$) δ 8.30 (2H, d, J=8.7 Hz), 7.81 (2H, d, J=8.7 Hz, 2H); $^{13}$C-NMR δ (75.5 MHz, acetone-$d_6$) 150.7, 145.3 (dm, J=243 Hz), 144.2 (dm, J=263 Hz), 135.4, 128.4, 125.9, 117.9 (m), 104.8 (t, J=3.4 Hz), 78.5 (t, J=4.2 Hz); $^{19}$F-NMR (282 MHz, $CDCl_3$) δ −137.5 (m), −89.6 (m). HRMS (EI$^+$) calcd for $C_{13}H_4F_4N_2O_2$ 296.02089. found 296.02104.

4-(2,3,5,6-Tetrafluoropyridin-4-ylethynyl)aniline (11). A solution of $SnCl_2$ (1.6 g, 8.4 mmol) in THF (5 ml) was slowly (1.5 hours) added to the mixture of 4-(2,3,5,6-tetrafluoropyridynylethynyl)nitrobenzene (0.5 g, 1.7 mmol) and HCl (1 ml) in THF (5 ml). The reaction mixture was stirred at room temperature for 2 hours. After neutralization with NaOH (1.0 N solution), product was extracted with dichloromethane. Solvent was evaporated and the residue was purified by column chromatography on silica gel using chloroform as the eluent to yield the aniline product as a yellow solid (0.39 g, 86%): m.p. 164-165° C.; $^1$H-NMR (300 MHz, $CDCl_3$) δ 7.43 (2H, d, J=8.7 Hz), 6.66 (2H, d, J=8.7 Hz), 4.04 (2H, br s); $^{13}$C-NMR δ (75.5 MHz, $CDCl_3$) 148.8, 143.5 (dm, J=244 Hz), 141.4 (dm, J=262 Hz), 134.2, 118.2 (m), 114.6, 109.4, 108.6 (m), 72.5 (t, J=4.1 Hz); $^{19}$F-NMR (282 MHz, $CDCl_3$) δ −136.5 (m), −88.6 (m); HRMS (EI$^+$) calcd for $C_{13}H_6F_4N_2$ 266.04671. found 266.04720.

4-(Phenylethynyl)nitrobenzene (12). 4-Bromonitrobenzene (1.2 g, 5.9 mmol), bis(triphenylphosphine)palladium(II) chloride (0.1 g, 0.15 mmol), and copper(I) iodide (0.03 g, 0.15 mmol) were added to 30 ml of triethylamine. The mixture was degassed by freeze/pump/thaw technique (three times) and phenylacetylene (0.7 ml, 6.5 mmol) was added. The solution was stirred at room temperature for 3 days. After filtration, water was added to the filtrate and it was extracted with $CH_2Cl_2$. The organic phase was dried with $Na_2SO_4$ and concentrated in vacuo. The product (75%) was purified by column chromatography. All spectral data were analogous to the literature data. Park, S. B.; Alper, H. *Chem. Commun.* 2004, 1306.

4-(Phenylethynyl)aniline (13). 0.28 g (1.24 mmol) of 4-(Phenylethynyl)nitrobenzene (12) was refluxed with $FeSO_4 \cdot 7H_2O$ (3.5 g, 12.4 mmol) in 20 ml of $MeOH/H_2O$ (1:1) for 11 hours. After cooling the reaction to room temperature, 6 ml of $NH_4OH$ (aq) was added to the mixture and it was refluxed for 1 hour. The reaction mixture was vacuum filtered and MeOH was removed by rotary evaporation. The residue was extracted with EtOAc and the organic phase was dried with $Na_2SO_4$. The product was isolated by column chromatography (EtOAc:Hexane=1:3) with 83% yield. All spectral data were analogous to the literature data. Norio, S. *Org. Lett.* 2004, 6, 1527.

General coupling method of amino acid conjugates. N-Boc protected amino acid and 4-substituted aniline were dissolved in pyridine. The solution was cooled to −20° C. and phosphorus oxychloride was added dropwise with vigorous stirring. The reaction mixture was stirred for 1 h at −20° C. and then at room temperature for 10 h. The reaction mixture was quenched with ice/water and anilide was extracted with EtOAc. The organic layer was washed with sat. $NaHSO_4$ three times, dried with $Na_2SO_4$ and was concentrated in vacuo. The crude product was subjected to chromatography with $CH_2Cl_2/CH_3CN$ as eluent and the desired N-Boc protected amino acid conjugate was obtained. The deprotecting step was achieved by stirring the N-Boc protected conjugate with gaseous HCl to give the HCl salt of the amino acid conjugate.

Figure 26:
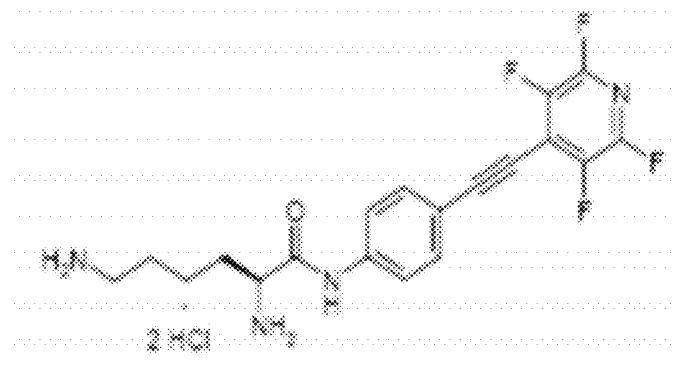
FIG. 26 shows the structure of compound 4.

(S)-2,6-Diamino-hexanoic acid [4-(2,3,5,6-tetrafluoro-pyridin-4-ylethynyl)-phenyl]-amide dihydrochloride (4)—as shown in FIG. 26. L-BocLys(Boc)-OH (1.3 g, 3.7 mmol) was reacted with aniline 11 by the general coupling method to obtain the desired N-Boc protected product as white solid (1.1 g, 51%): m.p. 137-139° C.; $^1$H-NMR (300 MHz, $CDCl_3$) δ 8.92 (1H, br s), 7.61 (d, J=8.4 Hz, 2H), 7.53 (d, J=8.7 Hz, 2H), 5.28 (m, 1H), 4.67 (br s, 1H), 4.23 (m, 1H), 3.14 (m, 2H), 1.96 (m, 2H), 1.70 (m, 2H), 1.53 (m, 2H), 1.46 (s, 9H), 1.45 (s, 9H). $^{13}$C-NMR δ (75.5 MHz, $CDCl_3$) 171.0, 156.5, 156.4, 143.4 (dm, J=244 Hz), 141.6 (dm, J=264 Hz), 140.2, 133.3, 119.4, 117.4 (m), 115.6, 106.9 (m), 80.7, 79.4, 73.2 (t, J=3.8 Hz), 55.2, 39.4, 31.0, 29.6, 28.4, 28.3, 22.5; $^{19}$F-NMR (282 MHz, $CDCl_3$) δ −139.0 (m), −91.0 (m); HRMS (ESI+) calcd for $C_{29}H_{34}F_4N_4Na_1O_5$ 617.23630. found 617.23619.

This compound (0.6 g) was dissolved in THF. Gaseous HCl was passed through that solution for 1 h. The solvent was evaporated, and solid (0.18 g, 40%) was recrystallized from ethanol. m.p. 260-264° C. (decomp.). $^1$H-NMR (300 MHz, $CD_3OD$) δ 7.81 (2H, d, J=8.7 Hz), 7.65 (2H, d, J=8.7 Hz), 4.09 (1H, t, J=6.6 Hz), 2.96 (2H, t, J=7.8 Hz), 1.98 (2H, m), 1.74 (2H, m), 1.55 (2H, m); $^{13}$C-NMR δ (75.5 MHz, $CD_3OD$) 168.9, 145.0 (dm, J=243 Hz), 143.4 (dm, J=262 Hz), 141.6, 134.4, 121.2, 118.5 (m), 117.6, 107.3 (m), 74.2 (t, J=3.8 Hz), 55.1, 40.4, 32.3, 28.3, 23.2; $^{19}$F-NMR (282 MHz, $CDCl_3$) δ −140.0 (m), −92.0 (m); UV/Vis ($H_2O$, pH 7) $\lambda_{max}$: 310 nm, ε: 28143 $M^{-1}$ $cm^{-1}$; HRMS (ESI+) calcd for $C_{19}H_{18}F_4N_4Na_1O_1$ 417.13144. found 417.13226.

Figure 27:
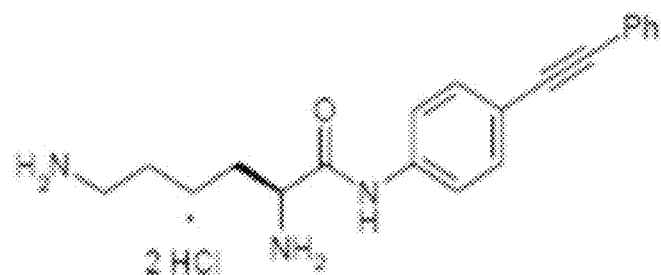
FIG. 27 shows the structure of compound 5.

(S)-2,6-Diaminohexanoic acid [4-(phenylethynyl)-phenyl]-amide dihydrochloride (5)—as shown in FIG. 27. 0.295 g (1.43 mmol) of DCC was added into the solution of compound 13 (0.2 g, 1.02 mmol), L-Boc-Lys(Boc)-OH (0.37 g, 1.12 mmol) and HOBT (0.16 g, 1.22 mmol) in 12 mL $CH_2Cl_2$. After stirring overnight, the mixture was filtered and evaperated in vacuo. Diethyl ether was added into the residue and the solution was washed with 10% citric acid and $NaHCO_3$ (aq). The organic layer was dried with $Na_2SO_4$ and concentrated. N-Boc protected product (0.24 g, 46%) was isolated by silica gel column chromatography (EtOAc:Hexane=1:2). The product 5 was obtained with 45% yield by HCl gas bubbling into the THF solution for 2 hours and crystalization: m.p. 98-100° C. (decomp.); $^1$H-NMR (300 MHz, $CD_3OD$) δ 7.72 (2H, d, J=8.1 Hz), 7.49 (4H, d, J=8.4 Hz), 7.36 (3H, m), 4.14 (1H, t, J=5.7 Hz), 2.97 (2H, t, J=6.9 Hz), 2.01 (2H, m), 1.76 (2H, m), 1.58 (2H, m); $^{13}$C-NMR (75.5 MHz, CD$_3$OD) δ 168.4, 139.2, 133.2, 132.5, 129.6, 129.4, 124.6, 121.0, 120.7, 90.0, 89.8, 54.9, 40.4, 32.3, 28.2, 23.1; UV/Vis (H$_2$O, pH 7) $\lambda_{max}$: 295 nm, ε: 30833 M$^{-1}$ cm$^{-1}$; HRMS (ESI$^+$) calcd for C$_{20}$H$_{24}$N$_3$O$_1$ 322.19194. found 322.19197.

Figure 28:
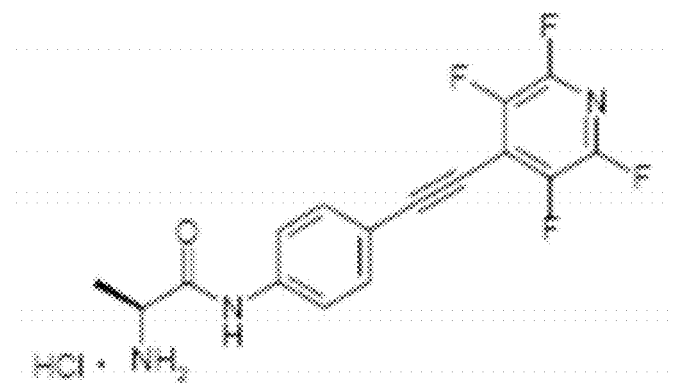
FIG. 28 shows the structure of compound 6.

(S)-2-Amino-propanoic acid [4-(2,3,5,6-tetrafluoro-pyridin-4-ylethynyl)-phenyl]-amide hydrochloride (6)—as shown in FIG. 28. Compound 11 (0.2 g, 0.75 mmol) and L-Boc-Ala-OH (0.28 g, 1.50 mmol) was reacted by the general coupling method to yield N-Boc-protected product with 46%: m.p. 204-210° C. (decomp.); $^1$H-NMR (300 MHz, DMSO-d6) δ 10.03 (1H, br s), 8.28 (2H, d, J=8.7 Hz), 8.10 (2H, d, J=8.7 Hz), 6.77 (1H, br s), 4.72 (1H, m), 1.86 (9H, s), 1.85 (3H, d, J=7.2 Hz); $^{13}$C-NMR (75.5 MHz, Acetone-d$_6$) δ 173.0, 156.6, 144.4 (dm, J=243 Hz), 142.9 (dm, J=261 Hz), 142.6, 134.1, 120.4, 115.6, 107.6 (t, J=3.4 Hz), 79.6, 73.7 (t, J=4.1 Hz), 55.1, 52.1, 28.6, 18.4; HRMS (ESI+) calcd for C$_{21}$H$_{19}$F$_4$N$_3$Na$_1$O$_3$ 460.12602. found 460.12672.

The desired product 6 was obtained by deprotection and recrystallization with 58% yield: m.p. 280-282° C. (decomp.); $^1$H-NMR (CD$_3$OD) δ 7.77 (2Hs, d, J=8.7 Hz), 7.64 (2Hs, d, J=8.7 Hz), 4.10 (1H, q, J=7.2 Hz), 1.62 (3Hs, d, J=7.2 Hz). $^{13}$C-NMR (CD$_3$OD) δ 169.7, 145.0 (dm, J=242 Hz), 143.4 (dm, J=262 Hz), 141.8, 134.4, 121.1, 117.4, 107.4 (t, J=3.3 Hz), 74.1 (t, J=4.5 Hz), 51.2, 17.7; UV/Vis (H$_2$O, pH 7) $\lambda_{max}$: 310 nm, ε: 28650 M$^{-1}$ cm$^{-1}$; HRMS (ESI+) calcd for C$_{16}$H$_{11}$F$_4$N$_3$Na$_1$O$_1$ 360.07359. found 360.07433.

6-Aminohexanoic acid [4-(2,3,5,6-tetrafluoro-pyridin-4-ylethynyl)-phenyl]-amide Hydrochloride (7).

Compound 11 (0.2 g, 0.75 mmol) and N-Boc-Caproic acid (0.35 g, 1.50 mmol) was reacted by the general coupling method to yield the N-Boc-protected product as light yellow power with 36%: m.p. 124-126° C.; $^1$H-NMR (300 MHz, CDCl$_3$) δ 7.72 (1H, br s), 7.64 (2H, d, J=8.7 Hz), 7.57 (2H, d, J=8.7 Hz), 4.62 (1H, br s), 3.13 (2H, dt, J=6.6 Hz), 2.39 (2H, t, J=7.5 Hz), 1.76 (2H, m), 1.53 (2H, m), 1.44 (9H, s), 1.40 (2H, m). $^{13}$C-NMR (75.5 MHz, CDCl$_3$) δ 171.4, 156.2, 143.5 (dm, J=245 Hz), 141.8 (dm, J=251 Hz), 140.3, 133.4, 119.4, 117.5 (m), 115.6, 106.8 (m), 79.3, (t, J=4.3 Hz), 40.1, 37.5, 29.7, 28.4, 26.1, 24.8; HRMS (ESI$^+$) calcd for C$_{24}$H$_{25}$F$_4$N$_3$Na$_1$O$_3$ 502.17297. found 502.17269.

Figure 29:
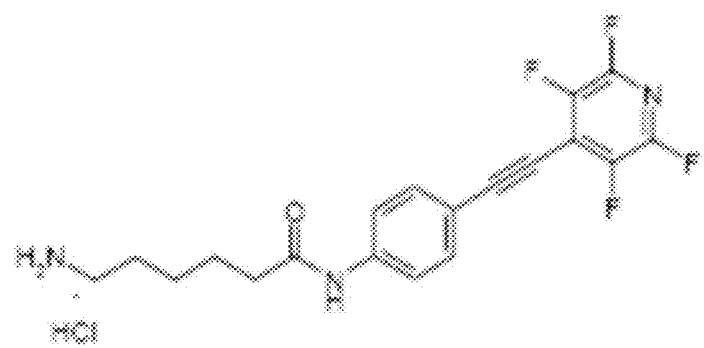
FIG. 29 shows the structure of compound 7.

The desired product 7, as shown in FIG. 29, was obtained by deprotection and recrystallization with 67% yield mp. 209-212° C. (decomp.); $^1$H-NMR (300 MHz, CD$_3$OD) δ10.12 (1H, s), 7.72 (2H, d, J=9.0 Hz), 7.58 (2H, d, J=8.7 Hz), 2.95 (2H, t, J=7.5 Hz), 2.46 (2H, t, J=7.2 Hz), 1.73 (4Hs, m), 1.48 (2H, m). $^{13}$C-NMR (75.5 MHz, CD$_3$OD) δ 174.5, 144.9 (dm, J=242 Hz), 143.2 (dm, J=262 Hz), 142.5, 134.2, 120.8, 118.5 (m), 116.5, 107.7 (m), 73.8 (t, J=4.0 Hz), 40.6, 37.6, 28.4, 27.0, 26.0; UV/Vis (H$_2$O, pH 7) $\lambda_{max}$: 310 nm, ε: 29730 M$^{-1}$ cm$^{-1}$; HRMS (ESI$^+$) calcd for C$_{19}$H$_{17}$F$_4$N$_3$Na$_1$O$_1$ 402.12054. found 402.12062.

Figure 30:
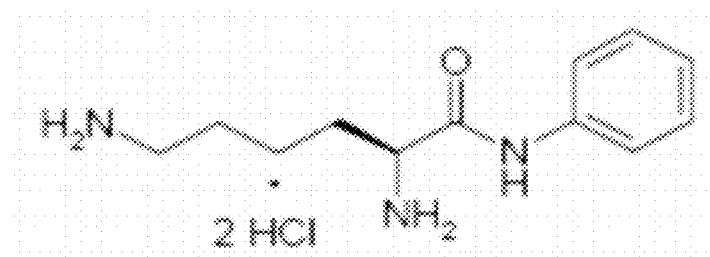
FIG. 30 shows the structure of compound 8.

(S)-2,6-Diaminohexanoic acid phenyl-amide dihydrochloride (8)—shown in FIG. 30.

DCC (0.47 g, 2.22 mmol) and DMAP (0.068 g, 0.56 mmol) were added to L-Boc-Lys(Boc)-OH (0.64 g, 1.85 mmol) solution in 12 ml of DMF. 0.33 ml of aniline (3.7 mmol) was added to the mixture and it was stirred for 20 hrs. After addition of EtOAc, the organic mixture was washed sequentially with saturated aqueous NH$_4$Cl and NaHCO$_3$. The organic layer was dried with Na$_2$SO$_4$ and concentrated. The product was purified by column chromatography (EtOAc: Hexane=1: 3, 1:1) with 30% yield: $^1$H-NMR (300 MHz, CDCl$_3$) δ 8.50 (1H, br s), 7.52 (2H, d, J=7.8 Hz), 7.28 (2H, dd, J=7.8 Hz), 7.08 (1H, t, J=7.5 Hz), 5.30 (1H, m), 4.65 (1H, m), 4.21 (1H, m), 3.12 (2H, m), 1.93 (2H, m), 1.69 (2H, m), 1.52 (2H, m), 1.46 (9H, s), 1.44 (9H, s).

HCl (g) was bubbled through the solution of N-Boc-protected product (215 mg) in 8 ml of MeOH at 0° C. for 1 hr. The reaction was stirred at room temperature overnight. After concentrating the reaction in vacuo, the residue was washed with diethyl ether three times and dried to yield the product quantitatively: $^1$H-NMR (300 MHz CD$_3$OD) δ 7.66 (2H, d, J=7.8 Hz), 7.33 (2H, dd, J=7.8 Hz), 7.13 (1H, t, J=7.5 Hz), 4.13 (1H, t, J=6.6 Hz), 2.97 (2H, t, J=7.8 Hz), 2.02 (2H, m), 1.76 (2H, m), 1.58 (2H, m); $^{13}$C-NMR (75.5 MHz, CD$_3$OD) δ 168.3, 139.0, 129.9, 125.8, 121.3, 54.9, 40.32.2, 28.1, 23.0; HRMS (ESI) calcd for C$_{12}$H$_{20}$N$_3$O$_1$ 222.16064. found 222.16081.

Results and Discussion pH-Dependent DNA Cleavage.

Figure 8:
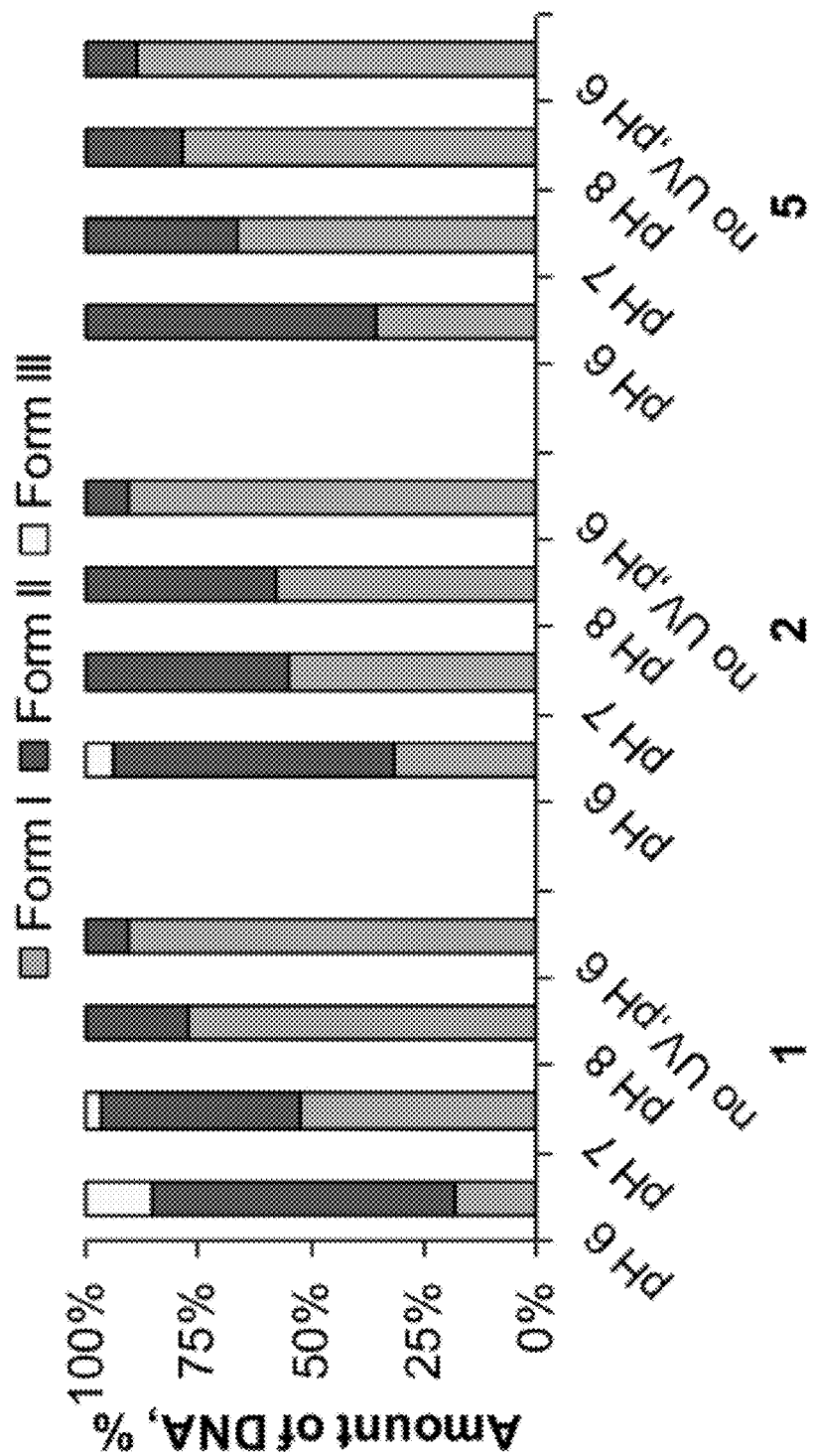
FIG. 8 depicts quantified plasmid relaxation assays with 15 µM of compounds 1, 2, 5 and 30 µM/bp of pBR 322 plasmid DNA in 20 mM of phosphate buffer at pH 6, 7 and 8 after 3 min. irradiation.

The ability of lysine conjugates to cleave DNA upon irradiation was investigated using conversion of supercoiled plasmid DNA into the respective relaxed circular and linear forms (Forms II and III). The relative amounts of the three DNA forms were determined by densitometric analysis of the gel electrophoresis bands. Although enhancement of DNA-cleaving ability has been observed for all lysine conjugates (see FIG. 8), we will focus our discussion below on compound 4.

Figure 6:
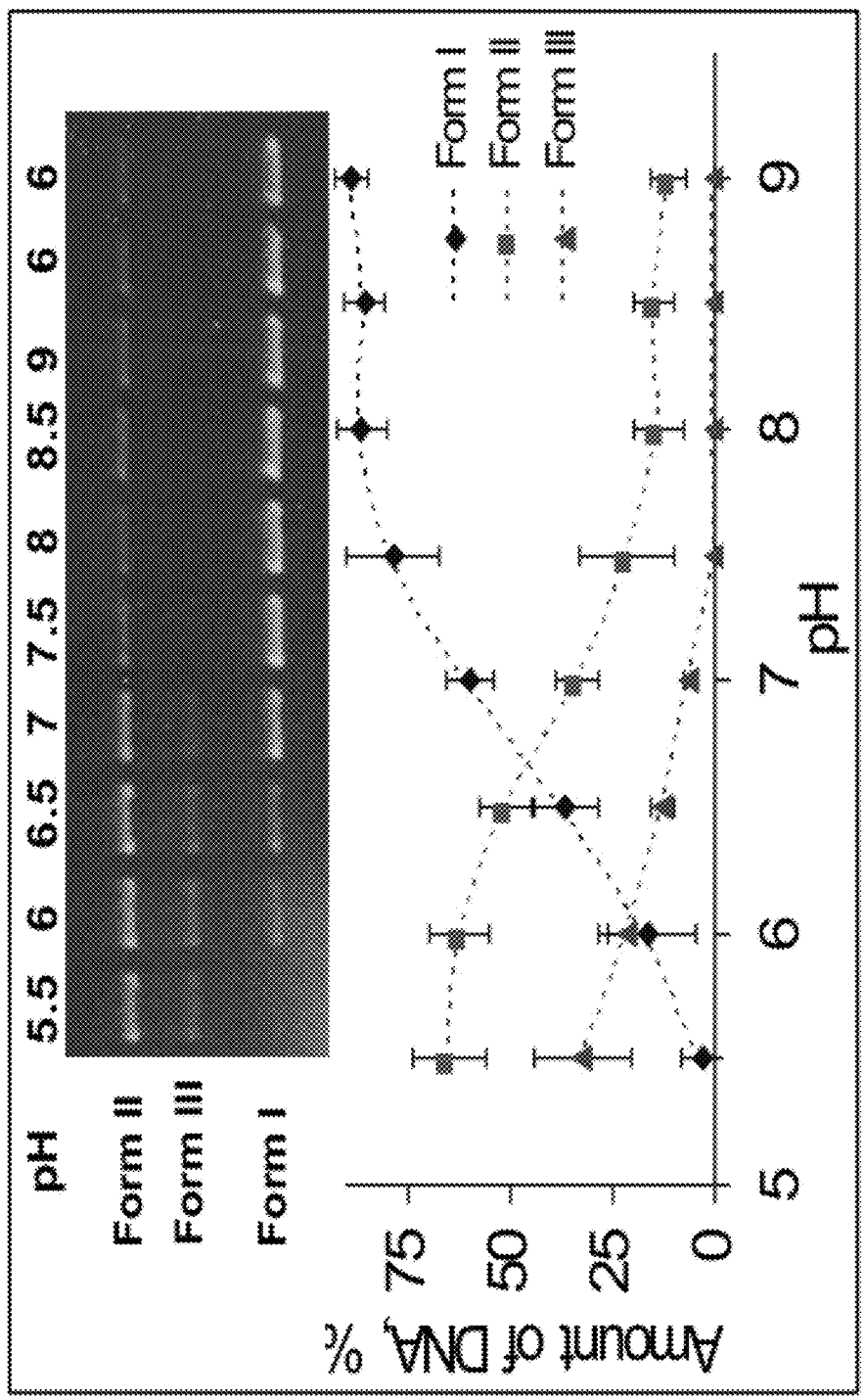
FIG. 6 depicts plasmid relaxation assays with conjugate 4 (15 µM) and pBR 322 plasmid DNA (30 µM/bp) in 20 mM phosphate buffer after 3 minutes of irradiation; Form I=intact supercoiled DNA, Form II=relaxed form (ss cleavage), Form III=linear form (ds cleavage); Lanes 1-8: from pH 5.5 to pH 9, lane 9: no compound+UV, lane 10: compound+no UV; cleavage data were quantified through densitometry; reported values represent the average of four experiments.

The most remarkable observation is the dramatic increase in efficiency of ds DNA cleavage caused by compound 4 when pH changes from neutral to slightly acidic (FIG. 6). While control experiments clearly indicate that no additional DNA cleavage is caused at this pH by the conjugate alone in the dark or by UV itself, the damage is amplified strongly when both light and compound 4 interact with DNA at the lower pH. At pH 6, only 16% of intact DNA (Form I) remained after 3 minutes of irradiation in contrast to 60% and 86% of unreacted DNA at pH 7 and 8, respectively. Even more remarkable is that at the concentrations where hardly any ds cleavage is observed at pH 7, the amount of double stranded cleavage at the lower pH reaches the 2:1 ss:ds ratio, which rivals DNA cleavage mediated by the natural antibiotics calicheamicin γ and bleomycin! Higher concentrations of 4 lead to as much as 50% of ds cleavage which, to the best of our knowledge, is unprecedented for a small molecule-based DNA-cleaver (natural or designed).

Interestingly, the dependences of all three forms of DNA cleavage from pH follow the classic titration curves, which afford the apparent pK$_a$ values of 6.6, 6.8 and 6.2 respectively for the Forms I, II and III (FIG. 7). All of these values agree that a significant change in the efficiency of DNA cleavage occurs at the pH 6-7 window ideal for targeting cancer cells.

Although all lysine-conjugates have similar pH-dependent trends (FIG. 8), conjugates 1 and 4 possess the greatest DNA-cleaving ability. As the result, we focused our mechanistic discussion on acetylene 4 which is not only less toxic than enediyne 1 in the dark (vide infra), but also does not aggregate and precipitate at the higher pH values (~8). When necessary, we have incorporated data for other conjugates as well.

Figure 9:
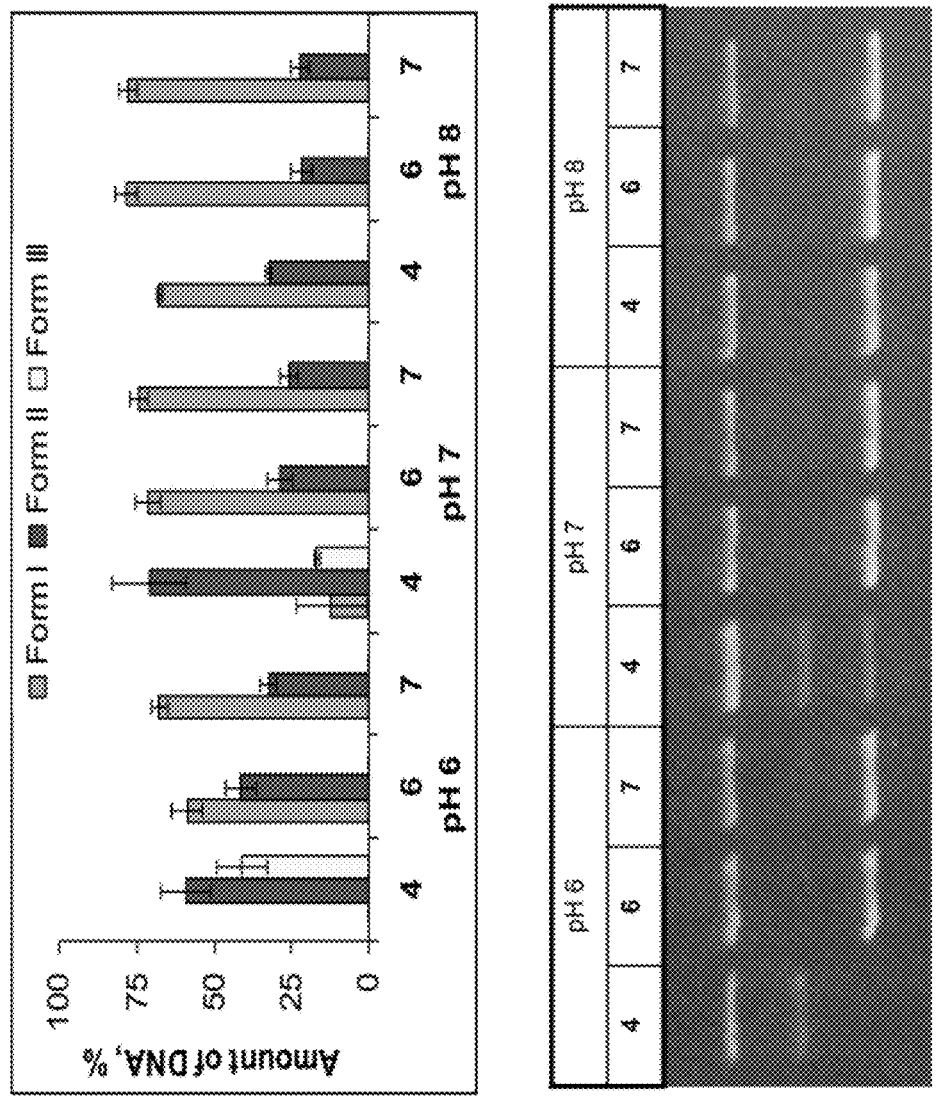
FIG. 9 shows plasmid relaxation assays for DNA photocleavage with 15 µM of compounds 4, 6 and 7 and pBR322 plasmid DNA (30 µM/bp) in 20 mM phosphate buffer (pH 6, 7, 8) after 10 min of UV irradiation; quantified cleavage data are presented on the left, the original gels are on the right.

In order to investigate the relative role of the two amino groups in these conjugates, we extended this study to include DNA cleavage activities of alanine and caproic acid conjugates 6 and 7. These compounds have only one amino group (at the α- and ε-carbon, respectively) and, as expected, show different behavior (FIG. 9). Even though the monoamines 6, 7 are comparable in reactivity to diamine 4 at pH 8, the two conjugates lacking one of the two amino groups rapidly fall far behind in their efficiency at the lower pH values and do not produce any ds-cleavage even at pH 6.

The fact that only the lysine conjugates produces clear ds cleavage under these conditions suggests that both amino groups are required for this process to occur. Several explanations are possible. For example, the remarkable ability of lysine to recognize a nick in DNA and facilitate a break of the complementary strand (the ss→ds cleavage conversion) discovered in our previous work may play some role in the high efficiency of the ds cleavage. However, the enhancement of this type of cleavage at the lower pH is an unprecedented phenomenon. This effect is likely to stem from the presence of the protonated α-amino group in compound 4 which enhances the efficiency of DNA cleavage through one of the three mechanisms outlined in FIG. 11 (vide infra).

Figure 10:
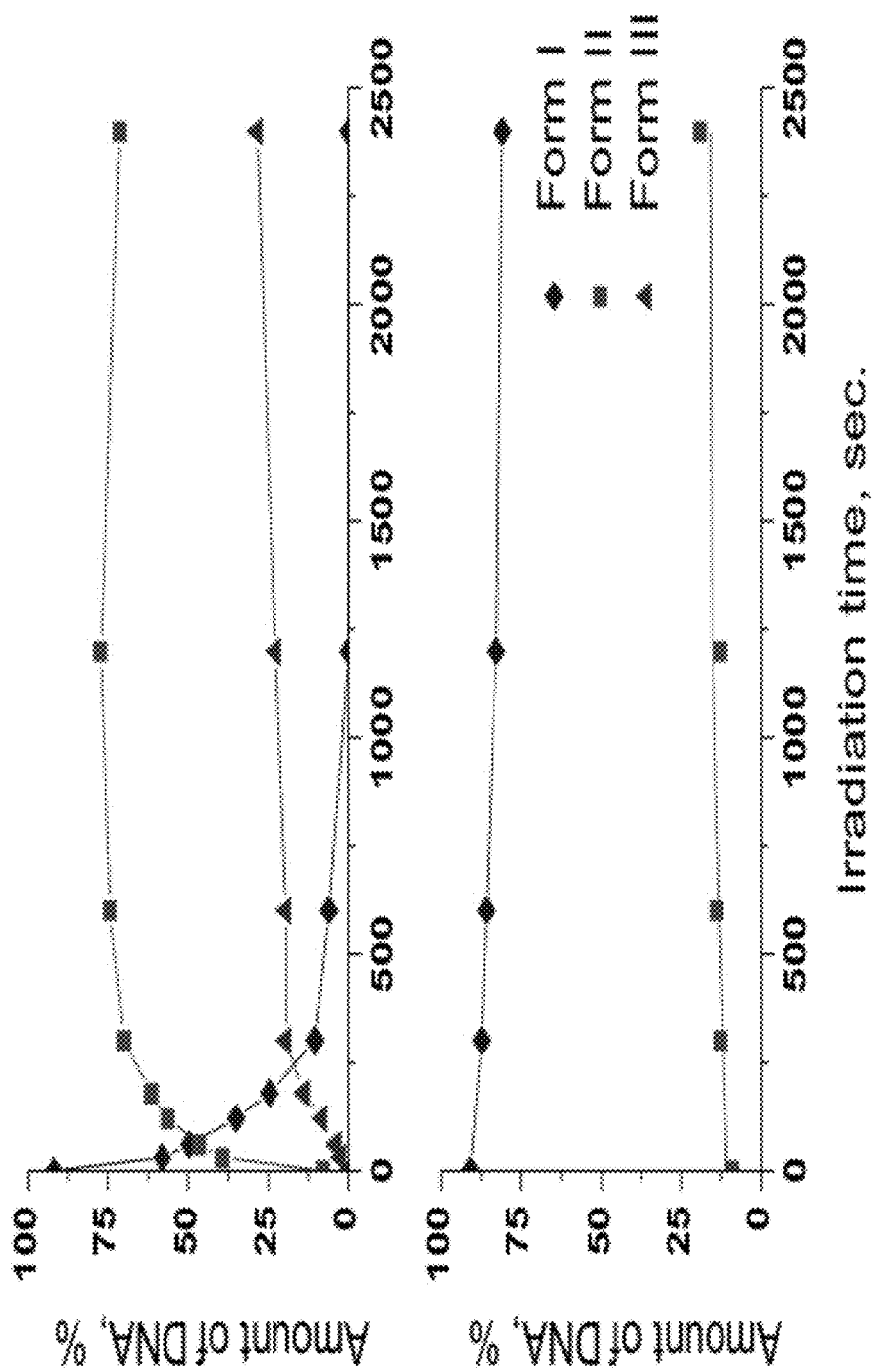
FIG. 10 provides quantified plots of pBR 322 plasmid (30 µM/bp) relaxation assays for 10 µM of compound 4 in 20 mM phosphate buffer at pH 6 (a), 7 (b) and 8 (c) as a function of the irradiation time; plots on the bottom show effect of UV on the DNA without the conjugate at different pHs; plots on the top illustrate reactivity in the presence of compound 4.
Figure 10:
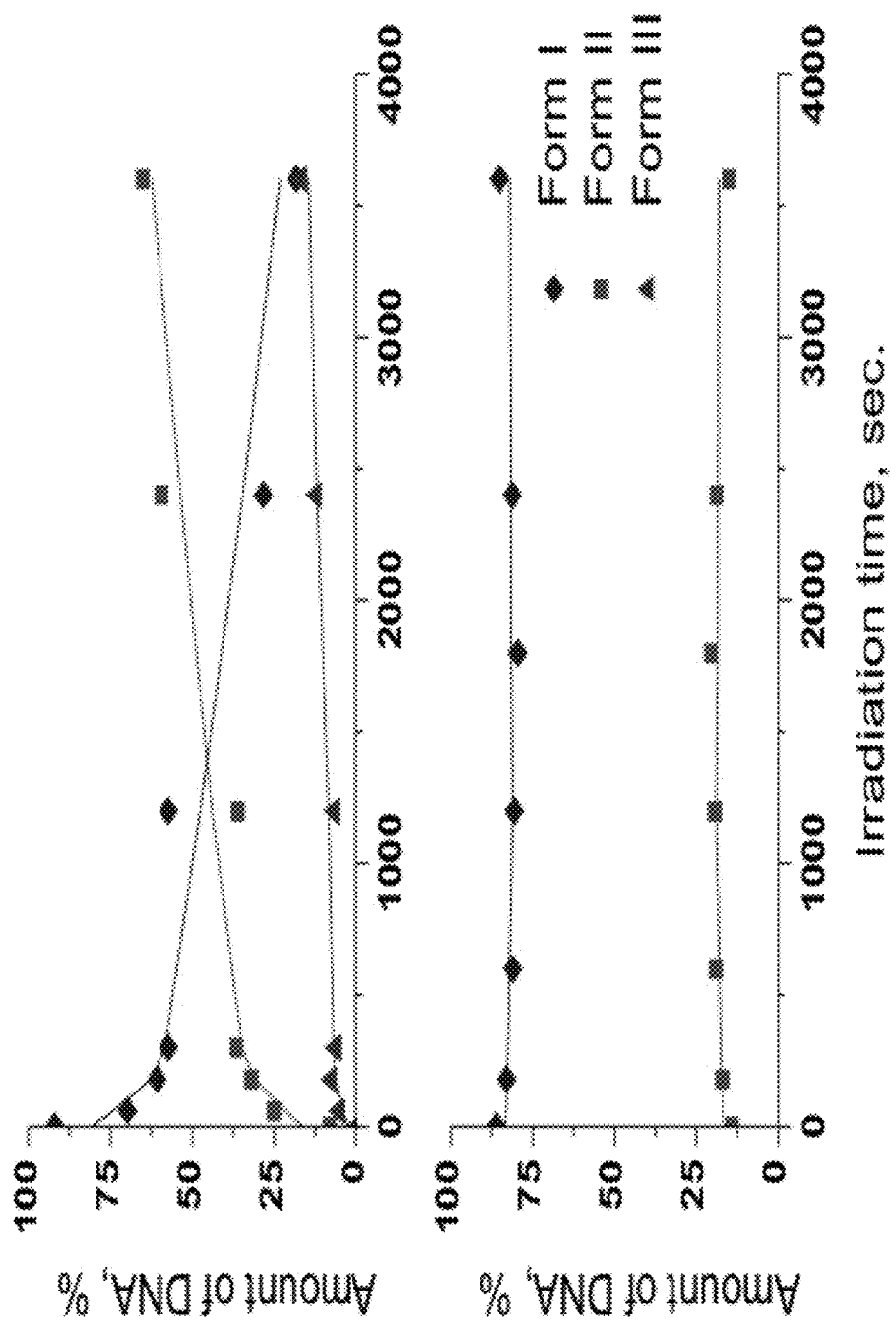
Figure 10:
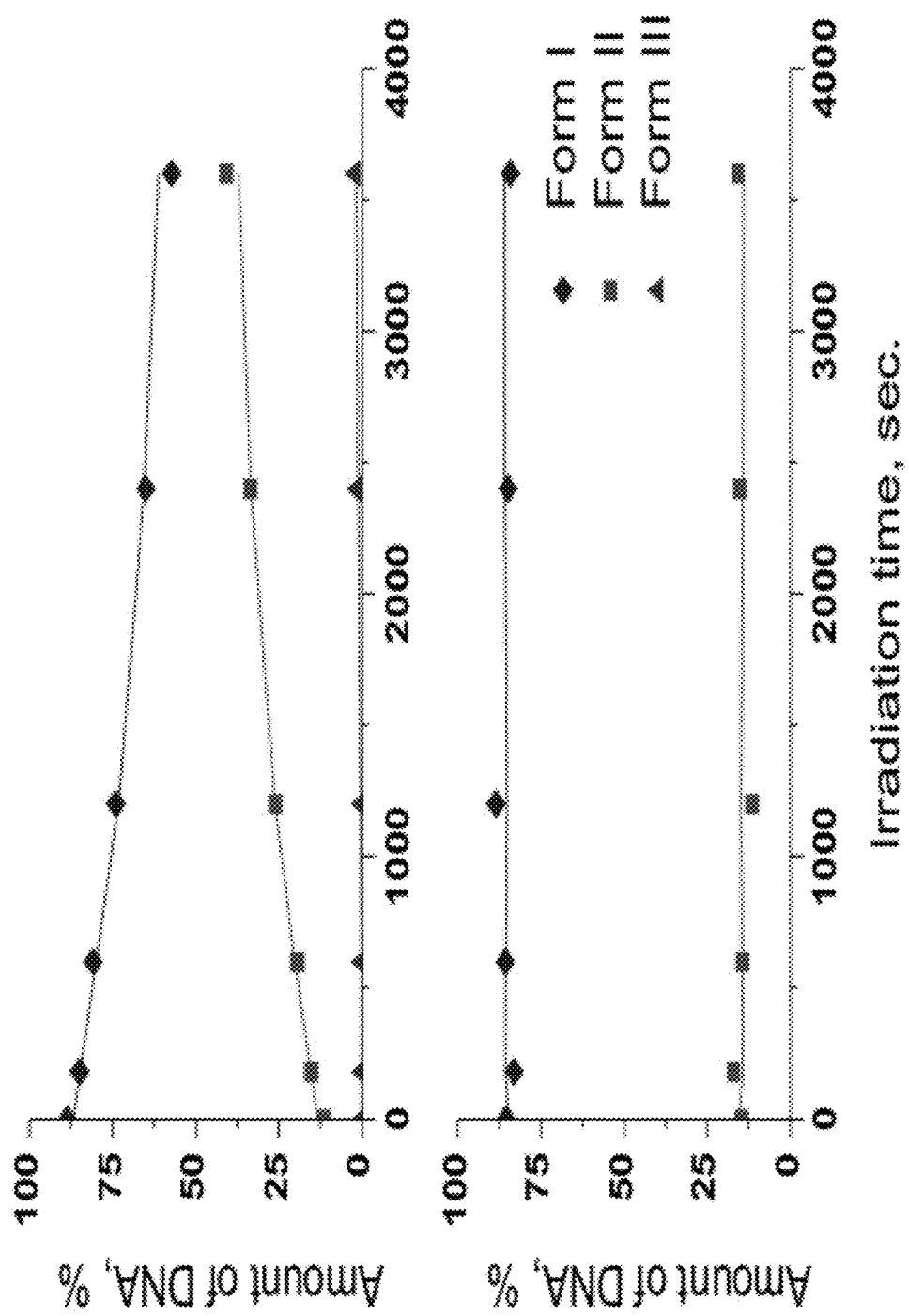

The difference in kinetics of DNA photocleavage by conjugate 4 at different pH values provides another illustration of the remarkable degree of pH-control (FIG. 10). DNA cleavage at pH 6 is remarkably fast—plasmid DNA is completely consumed within 5 minutes of irradiation, even though control experiments clearly show that there is very little of DNA damage by UV itself under these conditions. In a sharp contrast, DNA cleavage at pH 8 is slow—even after an hour of irradiation ~60% of DNA remains unreacted (note, however, that this reaction is still considerably faster than the damage by UV itself shown at the bottom part of FIG. 10). These observations indicate that, depending on the pH, compound 4 can induce DNA damage in two kinetically different ways. The DNA-damaging activity at pH 7 can be described as a superposition of the two different cleavage patterns described above. These experiments also provide the control data to confirm that change in the pH per se does not induce acceleration of DNA photocleavage (lower part of FIG. 10). Instead, the observed pH-dependence stems from the properties of the lysine conjugates.

Mechanistic Alternatives for the Observed pH-Dependence of DNA-Cleavage.

Figure 11:
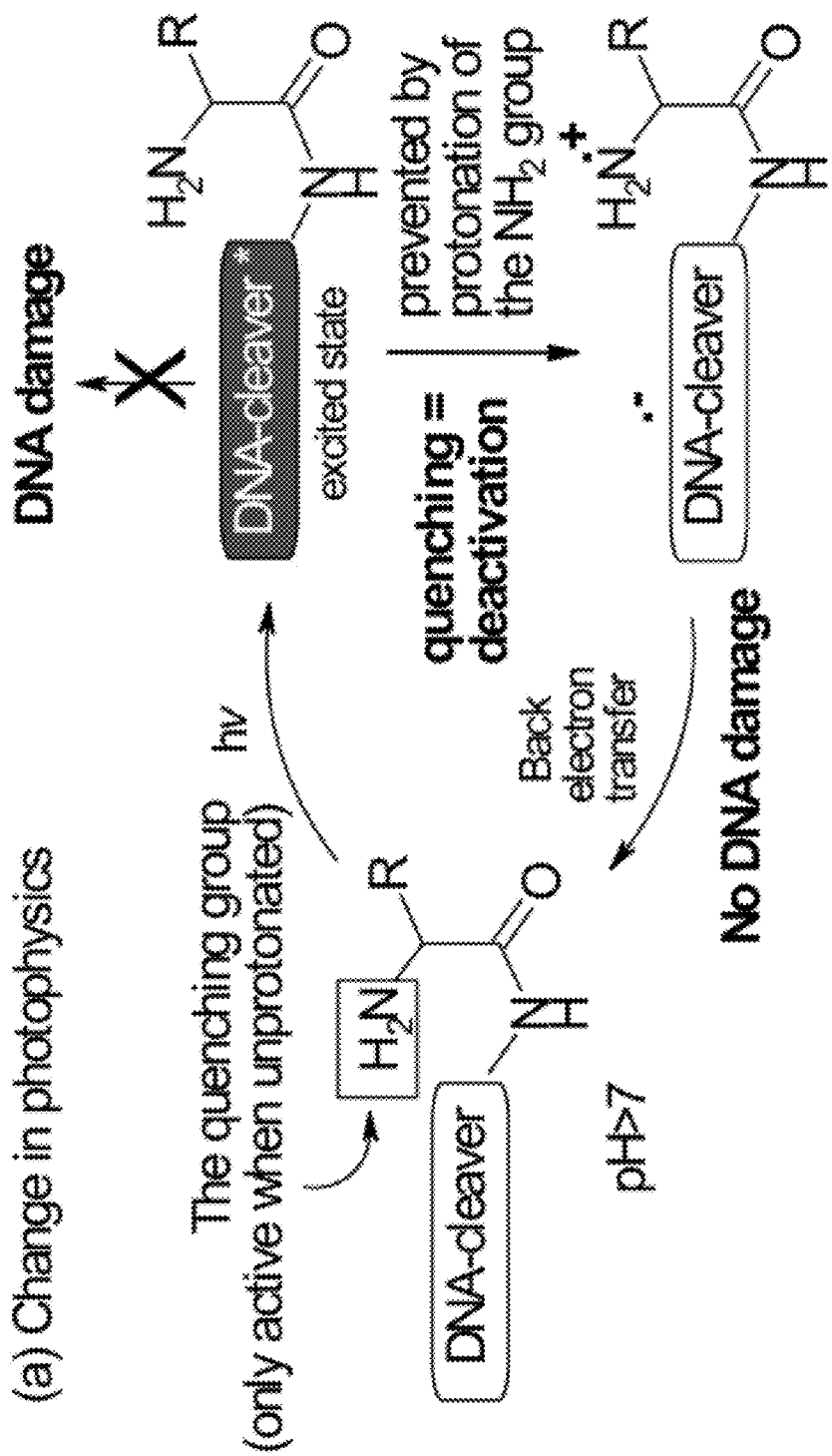
FIG. 11 illustrates three possible mechanisms for pH-regulated DNA modification by lysine conjugates.
Figure 11:
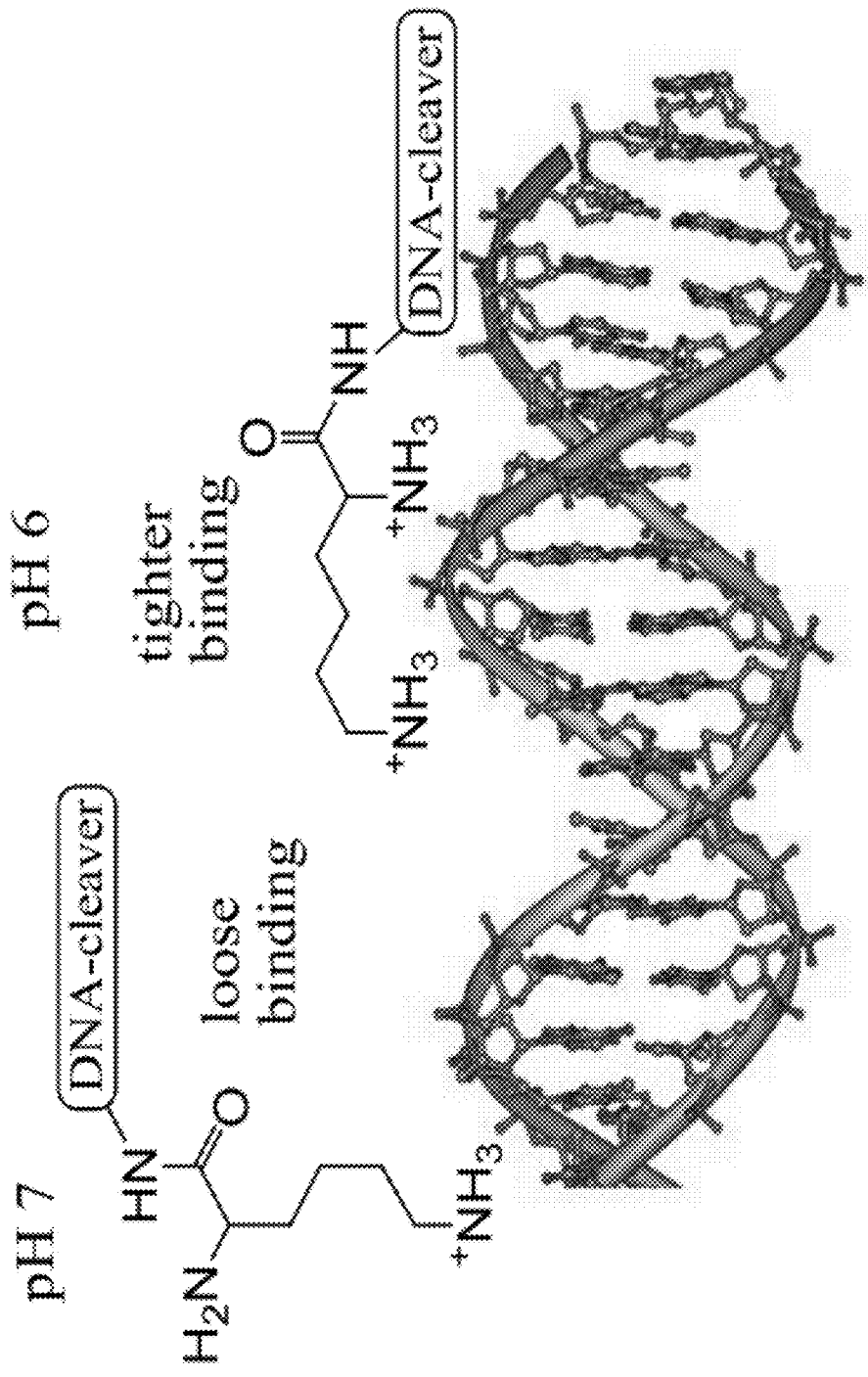
Figure 11:
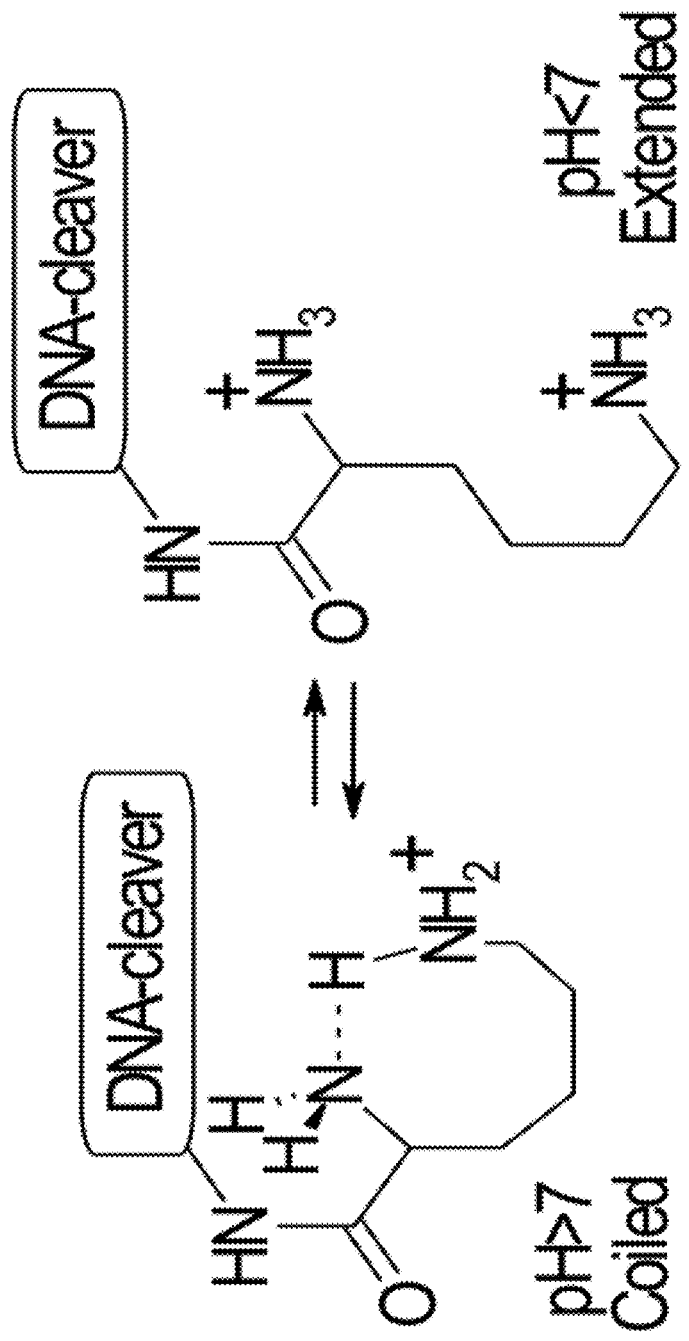
Figure 12:
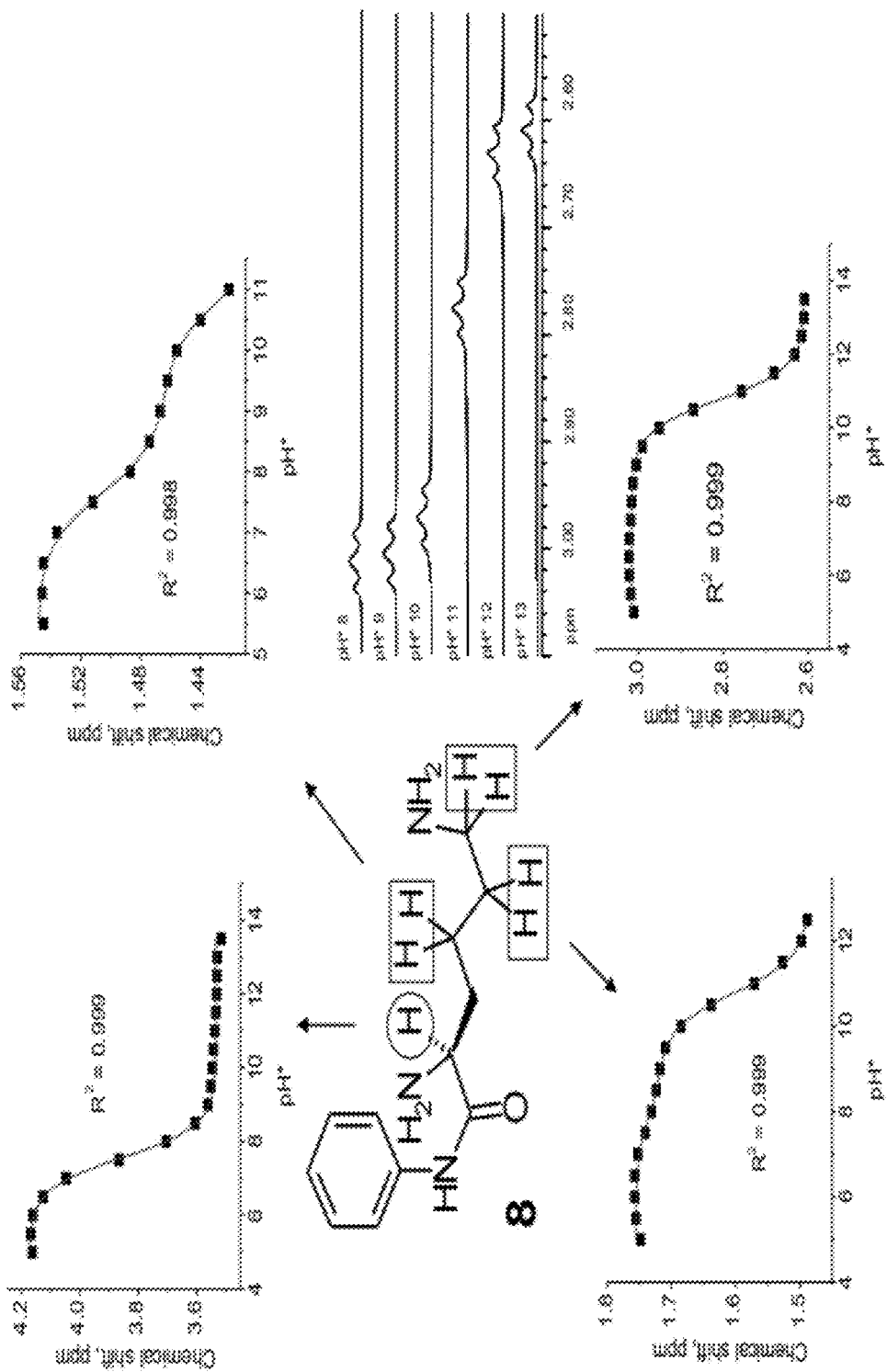
FIG. 12 shows $^1$H-NMR spectra of α- and ε-hydrogens in compound 8 (5 mM) in $D_2O$ at pD 5, 6, 7, 8, 9, 10, 11, 12, 13, and chemical shift-pD titration data for α- and ε-hydrogens in compound 8; these $pK_a$ values change to 7.44 and 10.40 when correction for going from $pK_a^{H*}$ to $pK_a$ is applied.

Several possible mechanisms which could lead to the observed pH-dependency for the interaction of lysine conjugates with DNA are outlined in FIG. 11. Mechanism (a) involves the control of deactivating intramolecular electron transfer from the donor α-amino group to the excited chromophore through protonation. Electron transfer intercepts the excited state of the DNA-cleaver, making it less active at higher pH. In contrast, at lower pH, both amino groups are protonated and the nitrogen lone pair is not available to deactivate the reactive excited state.

Another possibility is illustrated by a model for stronger binding of the diprotonated lysine moiety to DNA at lower pH, as shown in FIG. 11b. At neutral pH, only the more basic, remote amino group of the lysine moiety is protonated, leading to a relatively loose binding to DNA. At lower pH, the electrostatic interaction of positively charged ammonium groups and negatively charged phosphate groups of DNA brings the DNA-cleaving warhead close to the ribose backbone of DNA, providing a possible mechanism for the increase in the extent of DNA damage by this warhead.

Finally, we envisioned that a conformational change may occur upon the second protonation (FIG. 11c). Although it was not clear a priori whether the coiled conformation may gain sufficient importance in the strongly hydrogen bonding aqueous environment, it is interesting to consider such possibility as a protonation-induced shape change may lead to a change in the DNA binding mode.

Photophysical properties of the lysine conjugates with acceptor substituents will help us to determine whether the choice of photochemical DNA-cleavers activated through photoinduced electron transfer (PET) introduces a new component in the pH-controlled behavior (FIG. 11a). NMR analysis of different protonated species will elucidate the possibility of a conformational change (FIG. 11c) whereas pH-dependence in DNA binding will help to determine whether tighter binding is achieved for dications as illustrated in FIG. 11b.

However, before comparing the relative importance in the three possible pathways for the observed pH-dependence of DNA cleavage for the lysine conjugates, it is important to obtain reliable answers regarding the basicities of the two amino groups in the lysine conjugates. Is the presence of an acceptor moiety next to the α-amino group and another already protonated amino group sufficient to decrease the basicity of the α-amino group to the extent where the change in its protonation will occur in the vicinity of pH 6-7? If yes, how are these changes in the protonation state related to the changes in the efficiency of DNA binding? In order to address these questions, we proceeded to determine $pK_a$s for the two amino groups of the lysine moiety as well as binding affinities of the different protonated states to DNA.

Determination of $pK_a$ Values

Direct potentiometric pH determination of both $pK_a$ values is inaccurate for most of the conjugates because, at a pH where both ammonium groups are deprotonated and these molecules lose all their charge, the solubility in water becomes very low (<1 mM). The decrease in solubility leads to the apparent aggregation and distortion of potentiometric curves at the higher pH. This distortion prevents accurate curve fitting (see FIG. 25). Thus, we had to resort to alternative spectral methods. Fortunately, there is a selection of convenient procedures which provide complementary information which can be used for cross-checking the accuracy of the alternative approaches.

NMR titrations: The advantage of NMR titrations is that they provide direct structural information, allowing for differentiation of the two protonation events through observations of chemical shifts for hydrogens spatially close to one of the two amino groups. Such differentiation can confirm unambiguously whether the presence of a carbonyl group next to the amino group leads to a decrease in the $pK_a$ of the respective ammonium ion.

Favorable solubility of N-phenyl-lysine amide 8 in $D_2O$ rendered this molecule a particularly convenient substrate for the $^1$H-NMR studies. These studies followed changes in the chemical shifts of the lysine chain protons upon the protonation/deprotonation of the two amino groups during the pH (pD) titration. The titrations curves clearly showed that the α-amino group is less basic ($pK_a$=7.56) than the ε-amino group ($pK_a$=10.75). To allow comparison of these $pK_a$s with $pK_a$s obtained by other methods, one has to take into account the difference between $pK_a^{H*}$, which is obtained by a direct reading of the $H_2O$-calibrated pH-meter in a $D_2O$ solution, and $pK_a$ ($pK_a$=0.929$pK_a^{H*}$+0.42).

Figure 4:
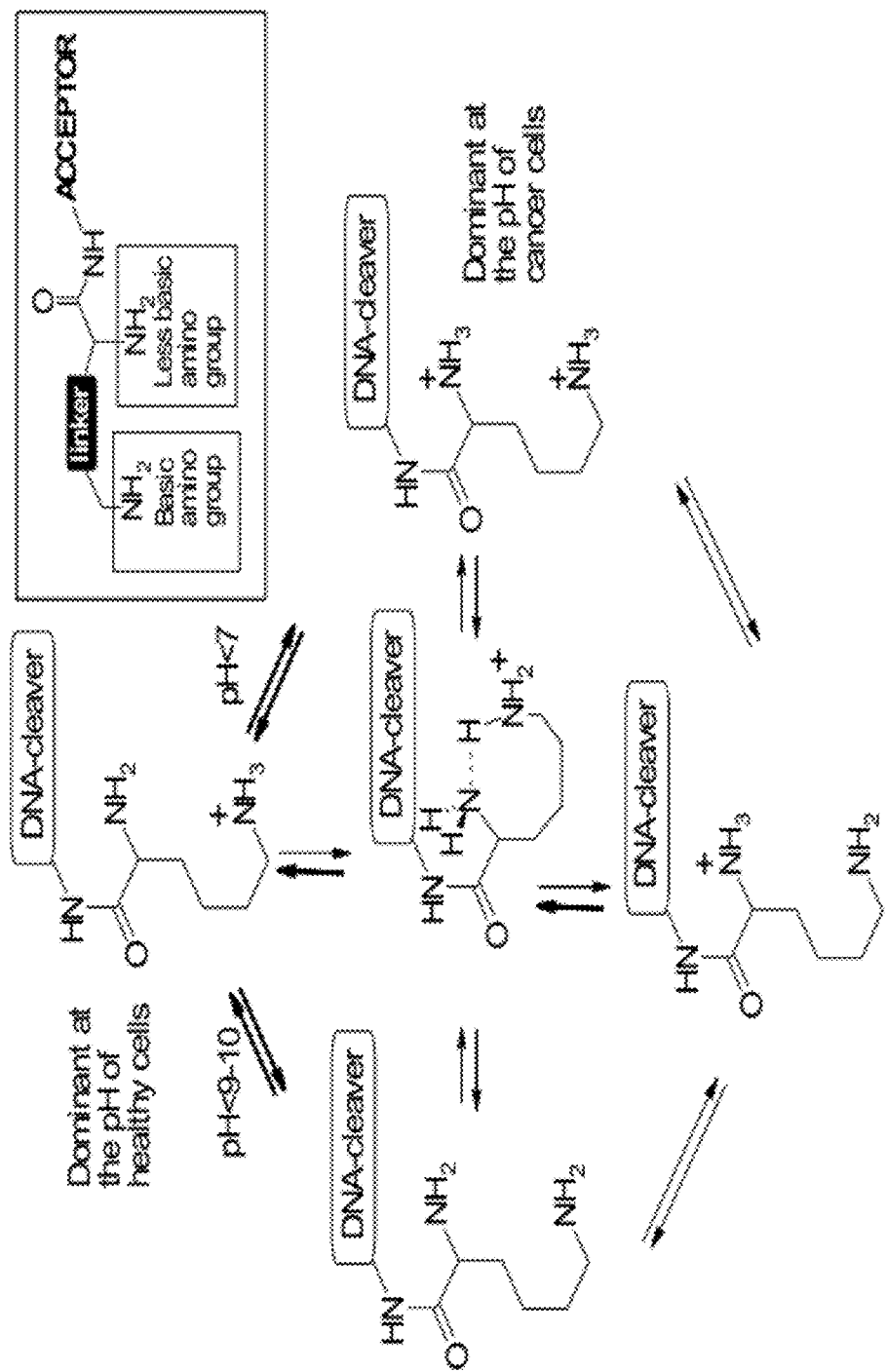
FIG. 4 provides schematics of the design of pH-dependent DNA-cleavers based on different stages of protonation of the lysine side chain, with the dominant protonation pathway indicated by the bold arrows.

Interestingly, monitoring of protons on the β, γ and δ-carbons produced two protonation curves with their relative sensitivity being directly proportional to the proximity to the respective amino groups. The observation that α-hydrogens are not sensitive to the change in protonation of the ε-amino group suggests a lack of communication between the two amino groups, thus eliminating the cyclic H-bonded structure in the monoprotonated species where the ammonium group is hydrogen bonded to the other $NH_2$ group of the same molecule (the central structure in FIG. 4 which corresponds to the mechanism (c) of pH-regulation in FIG. 11).

Figure 13:
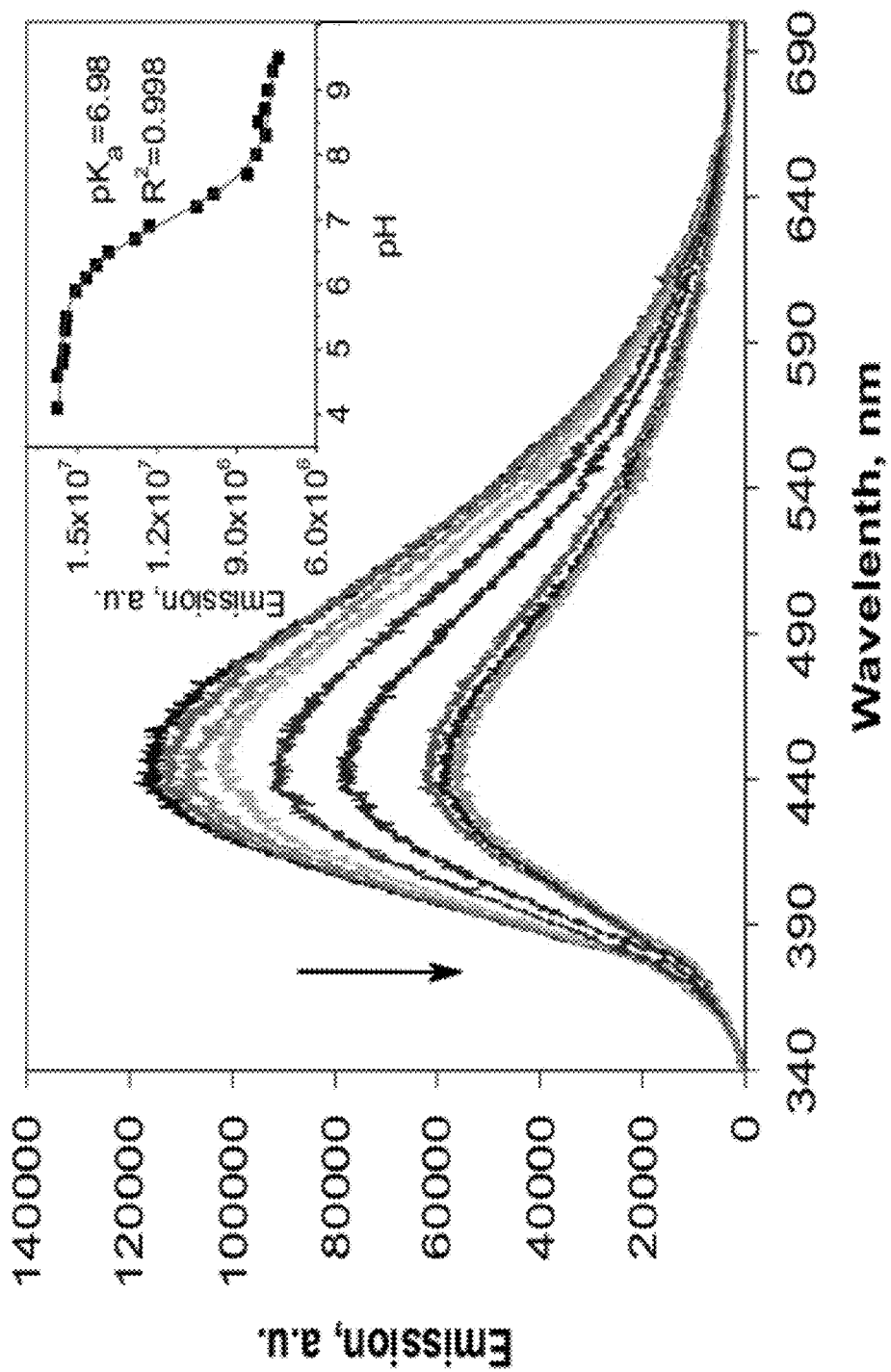
FIG. 13 shows fluorescence spectra of compound 4 (10 µM) at pH 4.1, 5.0, 6.1, 6.5, 6.9, 7.2, 8.0, 9.0, and 9.5; the insert shows quantified changes in fluorescence intensity as a function of pH and their fit to the Henderson-Hasselbach equation for an acid-base equilibrium involving one amino group.

Fluorometric determination of $pK_a$ of α-amino group: Highly sensitive fluorescence methods are especially convenient for compounds of limited solubility. We determined the basicity of the α-amino group using intramolecular quenching of fluorescence through photoinduced electron transfer (PET) from the α-nitrogen lone pair to the excited chromophore. At the lower pH, both amino groups are protonated and the lone pair of electrons at nitrogen is unavailable for inter- or intramolecular electron transfer. However, as the ammonium group adjacent to the chromophore loses the proton at the higher pH, electron transfer becomes possible and quenches the fluorescence (FIG. 13). Although the validity of this approach is based on the assumption that changes in intermolecular PET and other fluorescence quenching pathways with the pH are insignificant relative to intramolecular PET at the $10^{-5}$ M concentration. The advantage of fluorescence is that it is more sensitive to changes in the immediate vicinity of the chromophore and, thus, directly reports protonation of the α-amino group.

Figure 14:
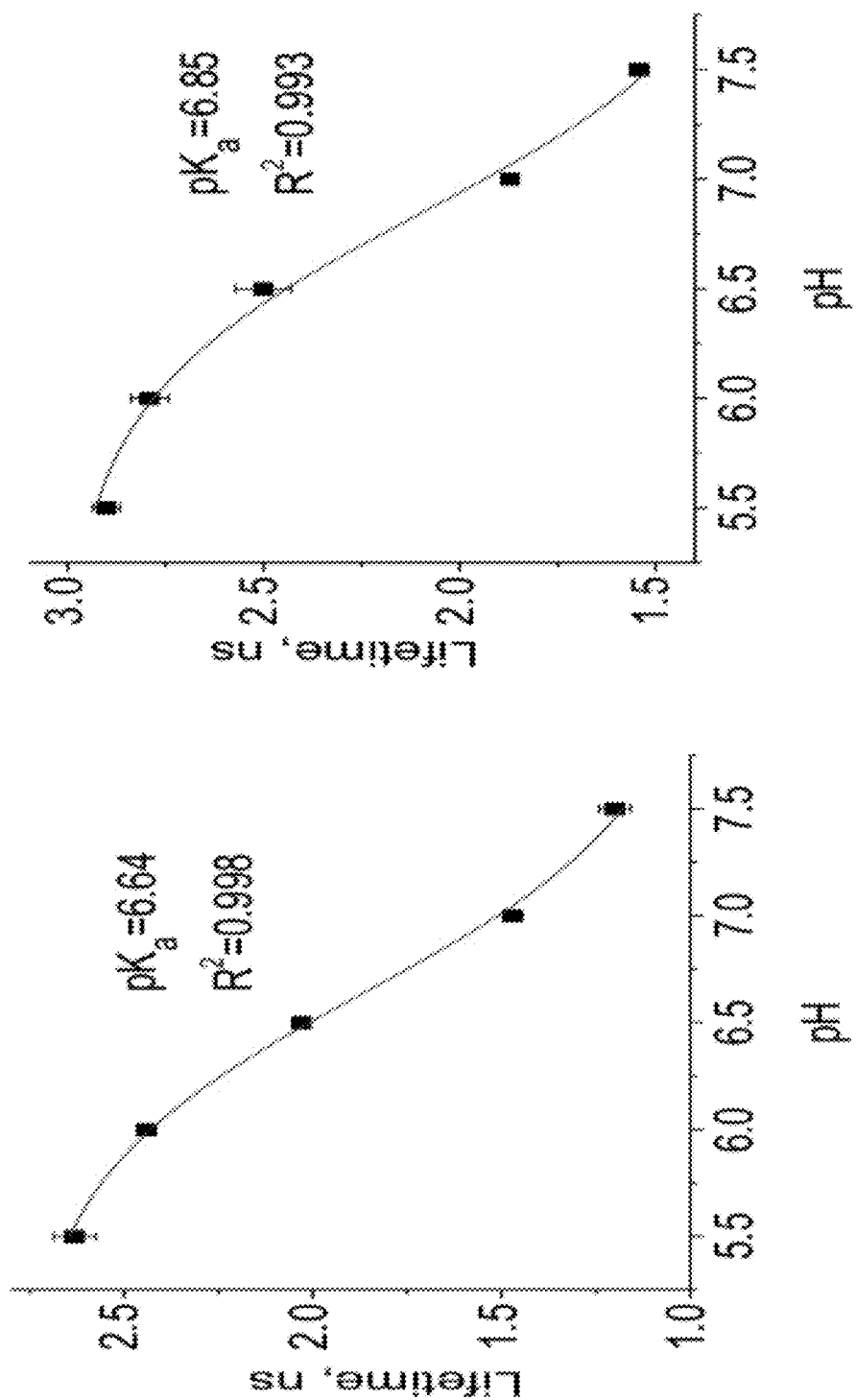
FIG. 14 provides line graphs showing the pH-dependent lifetimes of the singlet excited state for conjugates 4 and 6 (10 µM), measured in 20 mM phosphate buffer.

Lifetimes: To gain further insight into the effect of protonation on the excited state properties, we measured the singlet excited state lifetimes for compounds 4 and 6 as a function of pH. Within the error of measurement, all TFP-substituted compounds show a clear decrease in the lifetime of the singlet excited state at the higher pH. An illustration of the pH-dependence for the singlet excited state lifetimes of compound 4 and 6 is provided in FIG. 14.

The observed pH-dependency in the lifetimes means that the $S_1$ state is less available for triggering DNA-cleavage at the higher pH, a factor which should contribute to the observed decrease in activity under these conditions. At the lower pH, both amino groups are protonated, and hence electron transfer from the nitrogen lone pair does not deactivate the excited state, exactly as it is described in FIG. 11a.

UV-absorption titrations: Similar $pK_a$ values can be obtained using pH-dependent changes in the UV-Vis absorption spectra of the conjugates. This method is less sensitive as the changes observed are much smaller (about 10% increase in absorption upon transition from pH 11 to 5.5) than the analogous changes in the fluorescence spectra discussed in the previous section. In contrast to fluorescence, there are two titration curves for compound 4 which correspond to absorption changes of almost equal magnitude (Figure S4). The $pK_a$ for the first of these curves corresponds exactly to the $pK_a$ obtained from the fluorescence titrations. Interestingly, $pK_a$ for the ε-ammonium group of compound 7 is >1 $pK_a$ units lower than that derived from the fluorescence changes. Although the reasons for this interesting behavior of the terminal amino group extend beyond the scope of this disclosure, this subtle difference is irrelevant at the biologically relevant pH region where we observe the enhancement of ds-DNA cleavage. It is clear that, independent on the method, the $pK_a$ of the auxiliary ammonium group is sufficiently high to allow more than 99% of the respective amine to be protonated even at neutral pH. The above experiments do confirm unequivocally that the two amino groups of lysine conjugates possess different basicities and that the less basic α-group has the right properties to serve as a pH trigger for selective targeting of cancer cells. The term "basicity" is used herein, as known in the art, to indicate an ability to accept a proton or serve as a base in an acid-base reaction.

Summary of experimental $pK_a$ trends: The results for conjugates 4, 6, 7 and 8 are summarized in Table 1. The α-$pK_a$ for the lysine conjugates 4 is ~0.5 units lower than the $pK_a$ for the analogous alanine conjugate 6. This difference indicates that, as expected, the presence of a second cationic moiety does play some role in the decrease of α-amino moiety basicity. However, the relatively close $pK_a$ values for the α-ammonium groups in compounds 4 and 6 together with their large deviation from the $pK_a$ values for the ε-ammonium groups in compounds 4 and 7 illustrate that the lowered basicity of the α-amino group in the lysine conjugates is mostly due to its proximity to the amide moiety. It is also interesting that the presence of the acceptor tetrafluoropyridinyl moiety in 4 leads to a noticeable (~0.5-0.6 $pK_a$ units) decrease in the basicity of the α-amino group relative to that of the simple phenyl conjugate 8.

TABLE 1

The $pK_a$ values of amino groups in lysine conjugates 4, 8 and related monoamines 6, 7 according to emission/absorption and NMR spectra.

| Compound | 4 | 6 | 7 | 8 | Lysine |
|---|---|---|---|---|---|
| Method | Emission/absorption | Emission/absorption | Emission/absorption | $^1$H-NMR | — |
| $pK_a1$ | 6.98/6.9 | 7.6/7.4 | 10.8/9.4 | 7.56 (7.44)$^a$ | 8.95$^b$ |
| $pK_a2$ | —/9.5 | — | — | 10.75 (10.40)$^a$ | 10.53$^b$ |

$^a$Data in parenthesis include a correction factor;
$^b$from published literature Computational analysis of $pK_a$ trends: In order to provide a theoretical rationale to the observed differences in basicity, we investigated the electronic properties of the two amino groups in diamines 4 and 8. Natural Bond Orbital (NBO) analysis of the electronic structure of these compounds at the B3LYP/6-31G(d,p) level clearly shows that the α-nitrogen lone pair is lower in energy and has a significantly lower population than the ε-nitrogen lone pair (see Table 2). Both of these factors render the α-nitrogen a less efficient donor and a weaker base than the ε-nitrogen.

TABLE 2

NBO analysis of electronic properties of α- and ε-nitrogen lone pairs of diamines 4 and 8 at the B3LYP/6-31G(d,p) level of theory with the Polarizable Continuum Model (PCM) for solvation in $H_2O$.

| | Neutral | | | Protonated at the -nitrogen atom | | |
|---|---|---|---|---|---|---|
| | Occupancy, e | Energy, a.u. | Hybrid character, n in sp$^n$ orbital | Occupancy, e | Energy, a.u. | Hybrid character, n in sp$^n$ orbital |
| Compound 4 | | | | | | |
| α | 1.92791 | −0.30618 | 4.42 | 1.92765 | −0.30724 | 4.49 |
| ε | 1.96564 | −0.29939 | 3.50 | — | — | — |
| Compound 8 | | | | | | |
| α | 1.92941 | −0.30457 | 4.39 | 1.92906 | −0.30557 | 4.46 |

Figure 15:
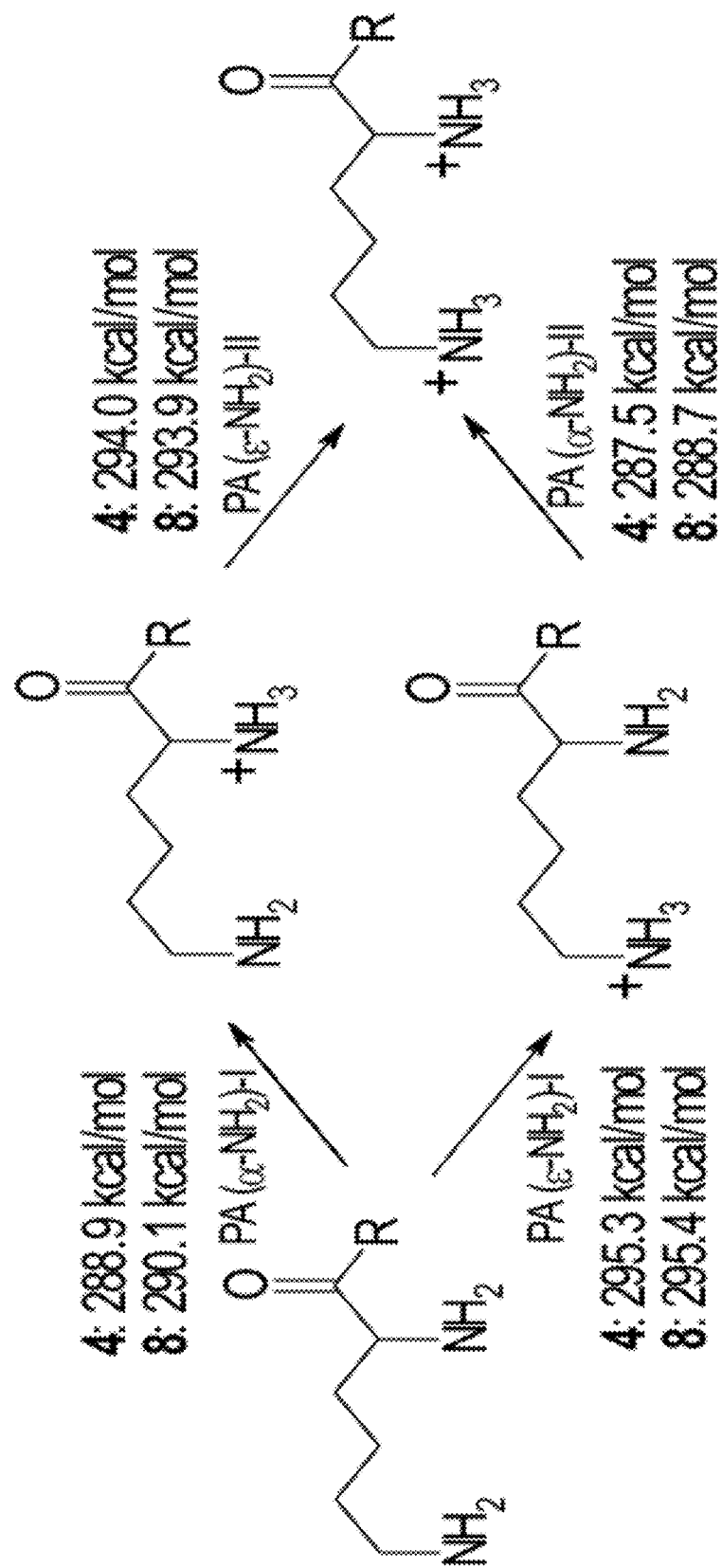
FIG. 15 shows proton affinities (in kcal/mol) of α- and ε-nitrogen lone pairs of diamines 4 and 8 at the B3LYP/6-31 G(d,p) level of theory with PCM solvation in $H_2O$.
Figure 16:
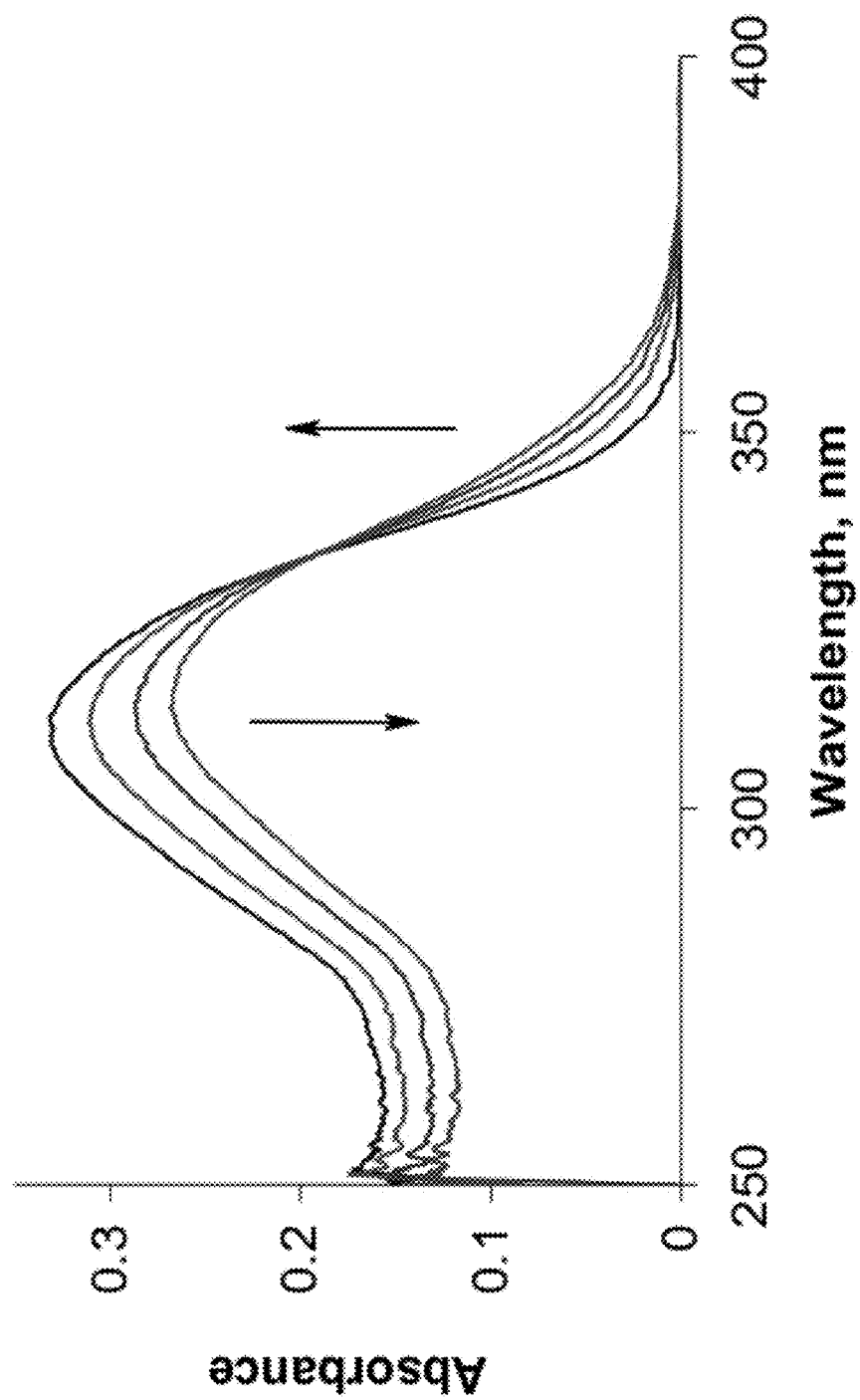
FIG. 16 depicts the results of UV-Vis absorbance titrations of 4 (10 µM) in 20 mM phosphate buffer with 0, 1, 2, 3 equivalents of 30 µM/bp CT DNA at pH 5.5 (a), pH 7 (b) and pH 8 (c)
Figure 16:
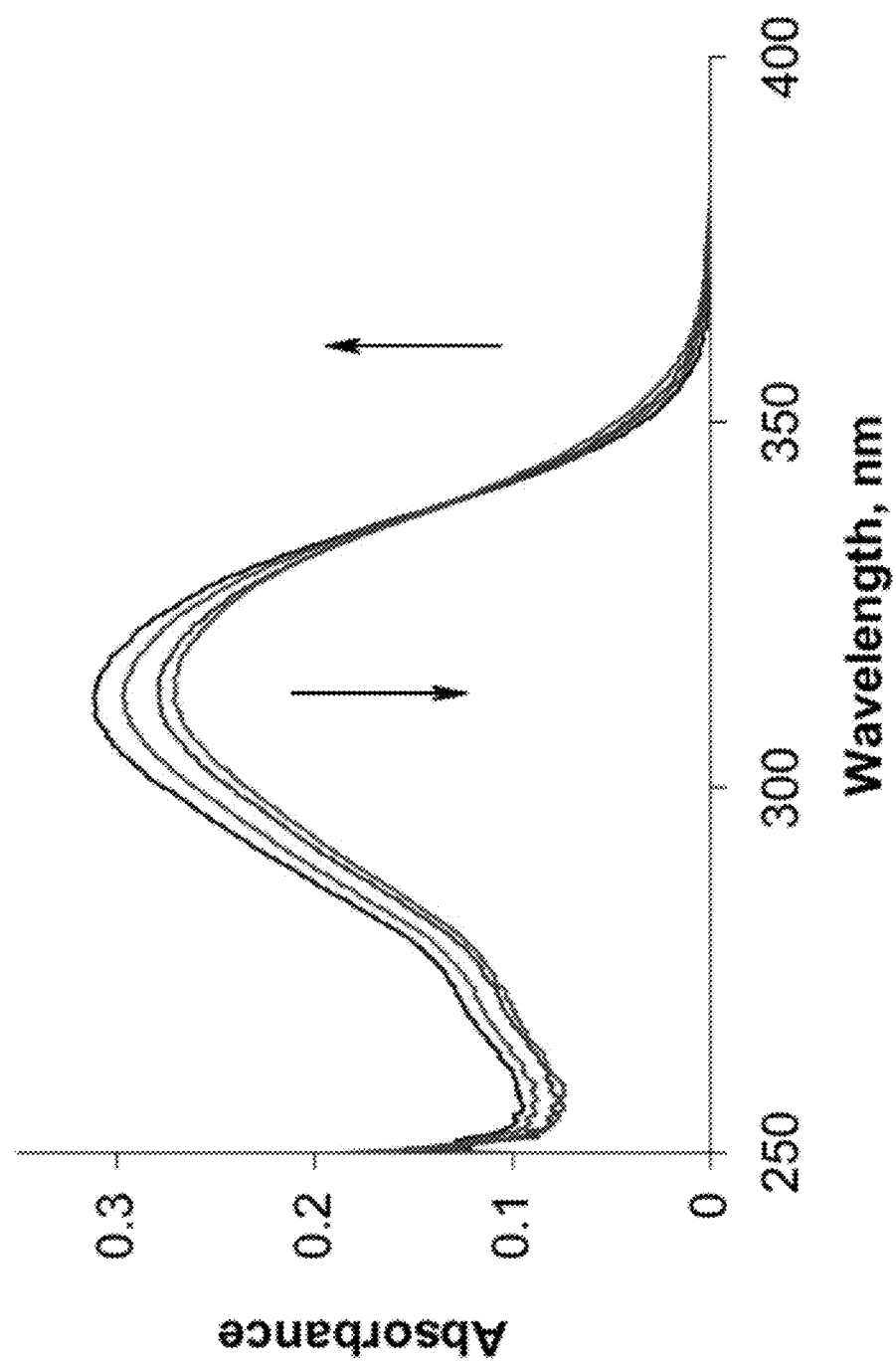
Figure 16:
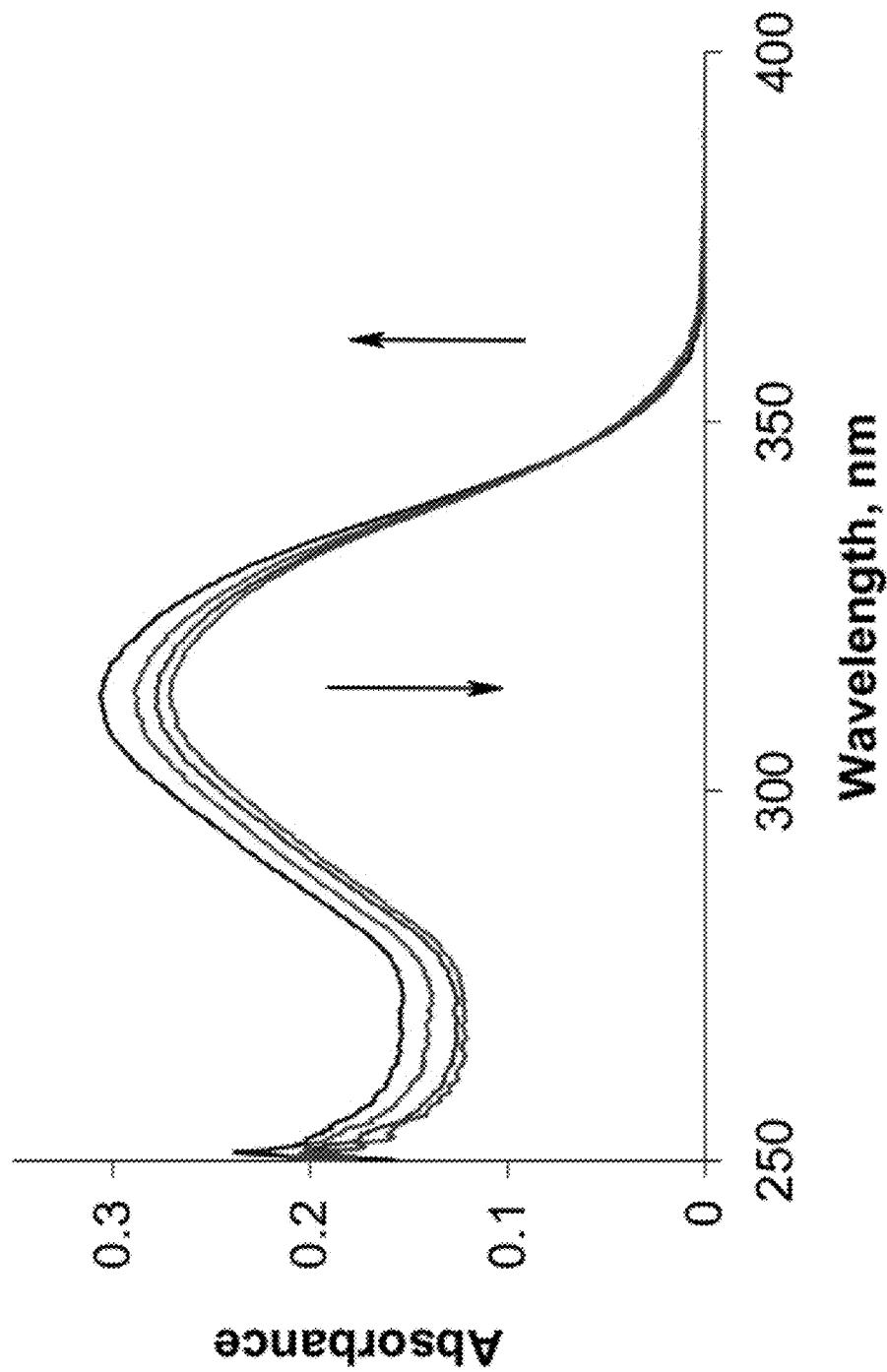

Proton affinities calculated at the B3LYP/6-31G(d,p) level in water (FIG. 15) support the above experimental findings very well. For both compounds 4 and 8, proton affinity of the ε-nitrogen is significantly higher than that of the α-nitrogen. In agreement with the experimental $pK_a$ values for monoamines 6 and 7 relative to the two $pK_a$ values of the diamines 4 and 8, the first protonation has some effect on the basicity of the second amino group but the effect is not dramatic (1.2-1.5 kcal/mol difference in the proton affinity values). In addition, and again in a full agreement with the experiment, the α-amino group in compound 8 is noticeably more basic than the α-amino group in compound 4 (1.2 kcal/mol difference).

pH-Dependent DNA Binding.

From a practical perspective, the $pK_a$ value of 7.0 for the TFP-acetylene 4 suggests that this compound exists mostly as the monocation at the slightly basic pH and it should be converted into >90% of the dicationic species at the same pH region (pH<6) where we observe the amplification of the ds DNA cleavage. The following section concentrates on interaction (binding) of DNA and lysine conjugates in the different protonation states. We approached this question through a combination of several methods outlined below. Note that qualitative treatments of binding affinities in these systems are difficult due to the presence of several species with different spectroscopic properties (the three protonation states of diamines) and inherent complexity of calf thymus (CT) DNA which offers numerous types of binding environments to the DNA-cleaver. As the result, we will limit ourselves in providing sufficient information for illustrating the differences in binding at the semi-quantitative basis.

Absorbance and Fluorescence Titration.

Titrations of 10 μM solutions of compounds 1-5 with calf thymus (CT) DNA revealed significant difference in absorbance and emission changes at different pH values. Results for compound 4 are discussed in more detail in this section. While little or no shift of $\lambda_{max}$ and small hypochromicity (14%, 12%, respectively) are observed for the titrations of conjugate chromophore with DNA at pH 7 and 8, the $\lambda_{max}$ changes from 310 nm to 315 nm during the titrations with the same amounts of DNA at pH 5.5 and 20% hypochromicity is observed. The greater change of absorbance at pH 5.5 indicates the larger interaction between the chromophore and DNA.

Changes in fluorescence upon the DNA titrations followed a similar pattern where greater changes were observed at the lower pH, indicating a stronger binding affinity to DNA. Interestingly, while emission of TFP-enediyne-lysine conjugate 1 was quenched with DNA (Figure S6), most likely through electron transfer pathway, we observed an increase in fluorescence for compound 4. This finding is likely to indicate that the DNA-binding modes for these two compounds are different. In particular, the fluorescence increase displayed by compound 4 suggests that it may be a DNA groove binder. Although fluorescence increase is often observed for intercalated chromophores as well, intercalation is unlikely in this system because close proximity to the nucleobases should quench fluorescence of 4 through electron transfer.

Figure 18:
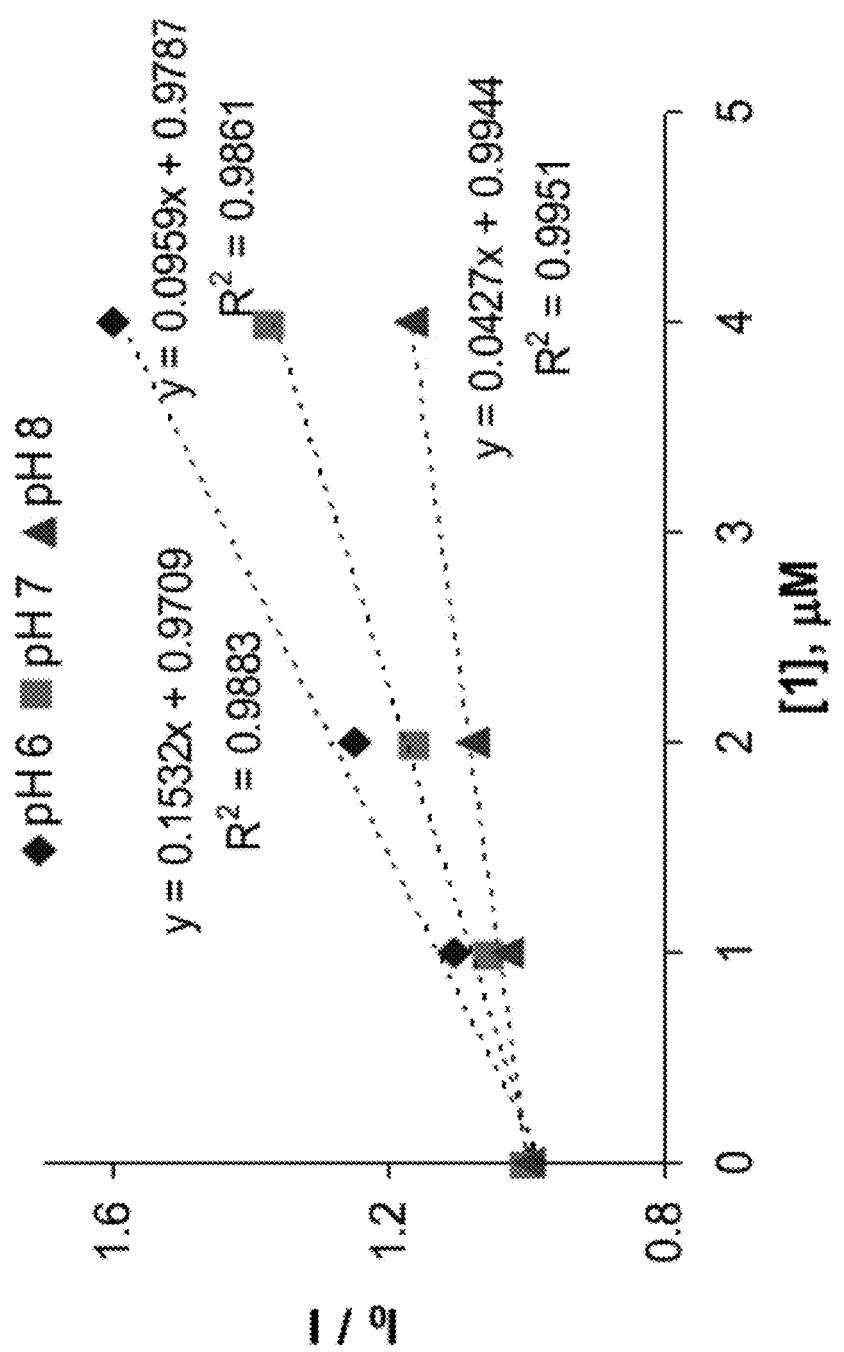
FIG. 18 shows changes in fluorescence of ethidium bromide (10 µM, the excitation wavelength=535 nm) in CT DNA (10 µM) as a function of displacement by compound 1.

Further evidence for a significant difference in binding modes of enediyne 1 and acetylene 4 is provided by the ethidium bromide displacement assays (FIG. 18). Only compound 1 displaces intercalated ethidium bromide from its complex with DNA, whereas addition of compound 4 does not lead to the displacement. This observation indicates again that compound 4 is not an intercalator. Nevertheless, despite the above differences in the DNA-binding mode, both lysine conjugates display similar pH-dependence in their DNA-cleavage.

Overall, both compounds show a much greater spectral response at the lower pH. As pH increases, the changes become less pronounced, indicating a lower degree of interaction between the compounds and DNA at the higher pH. This trend was also shown in measurement of binding affinity of compound 4 to CT DNA by isothermal titration calorimetry (ITC, see the SI part for details). These observations are consistent with the protonation behavior of these diamines discussed in the previous sections. At the lower pH, both amino groups are protonated to provide a higher degree of attraction between the two positive charges of the ammonium groups and the negative charges of the DNA phosphate backbone.

Mechanistic Considerations and pH-Dependence of the Involvement of Diffusing Radicals in the DNA Cleavage.

Figure 19:
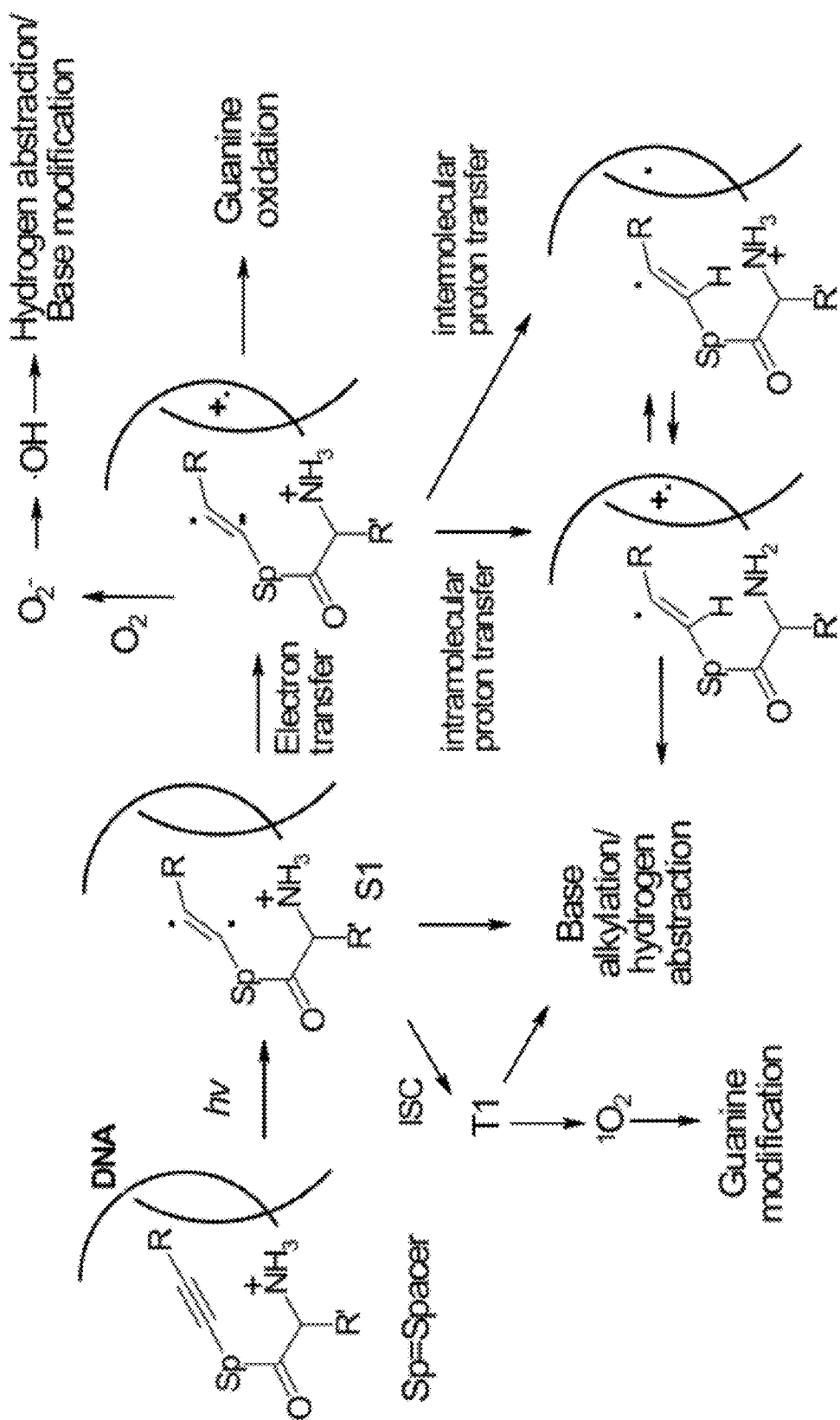
FIG. 19 provides a schematic diagram summary of possible mechanistic alternatives for the observed DNA cleavage by amino acid/acetylene conjugates.

The potential complexity of chemical mechanisms which can be involved into DNA photocleavage by lysine acetylene conjugates is illustrated in FIG. 19. A priori, a number of mechanisms may be considered as an explanation for the observed photochemical DNA cleavage by compound 4. In the first step, photochemical excitation leads to the formation of acetylene excited singlet state. After this necessary step, the list of diverging possibilities includes a number of choices such as generation of reactive oxygen species like singlet oxygen, superoxide and OH radical; direct hydrogen abstraction from DNA sugar backbone by photogenerated radicals, or singlet and triplet excited states; oxidative damage due to electron transfer from DNA nucleobases; and photoinduced DNA alkylation.

We have shown previously that cleavage by the enediyne and acetylene derivatives discussed in the work proceeds with selectivity for guanine-rich parts of DNA which flank AT-tracts due to a compromise between AT-selectivity for binding and G-selectivity for the formation of reactive species through PET. Both the selectivity and the fact that the lesions in DNA-oligomers required piperidine treatment clearly indicated that PET is involved in the damage. However, purely oxidative damage could not be the only mechanism because several compounds including 4 caused noticeable damage at a single G inside of a 12-bp AT-tract. This observation suggested that these photocleavers may damage DNA through base alkylation as well. Subsequent work confirmed that compound 4 in capable of localized DNA cleavage and the damage does not dissipate through hole hopping when the same single G site is chosen as a target using phosphate-lysine recognition. Furthermore, we also observed frank cleavage in 5-(AATT)$_n$GG(AT)$_m$GG(AAATTT)$_r$-3' oligomers. The cleavage is amplified by heat which is indicative of either base pair alkylation or abstraction of a C1'-hydrogen by reactive radical species. We have confirmed that triplet excited states of TFP-acetylenes behave as strongly electrophilic radicals which can alkylate π-systems. Taken together these observations suggest base pair alkylation is likely to complement direct PET damage as an important mechanism for the DNA damage, especially at the lower pH and tighter binding.

Further mechanistic details are unclear at the moment and a number of possible scenarios can be suggested. In particular, intersystem crossing (ISC) may convert this excited state into a triplet state of the TFP-acetylene moiety, shown to behave as a highly electrophilic diradical. In addition, the triplet state of the photocleaver may sensitize the formation of singlet oxygen. Alternatively, PET from DNA can lead to the formation of acetylene radical-anion and electron hole at one of the DNA bases. Electron transfer from acetylene radical-anion to dissolved oxygen would form superoxide anion which can be transformed into other reactive oxygen species.

Depending on the relative rates of hole hopping and hole trapping, the DNA electron hole can either be trapped at a suitable location to produce an oxidized DNA base (likely, a guanine) or transfer a proton to the DNA-cleaver radical-anion. This proton transfer (which can be classified as Proton-Assisted Electron Transfer) would transform the charge separated ion-pair into two new radicals, one at DNA and another at the partially reduced triple bond. The latter vinyl radical can be also formed when the intermediate radical anion of the DNA-cleaver receives a proton (possibly through a solvent-mediated mechanism) from the adjacent α-ammonium group (FIG. 19). Independent on the formation pathway, this vinyl radical can either abstract hydrogen from the deoxyribose backbone or alkylate an adjacent base.

Figure 20:
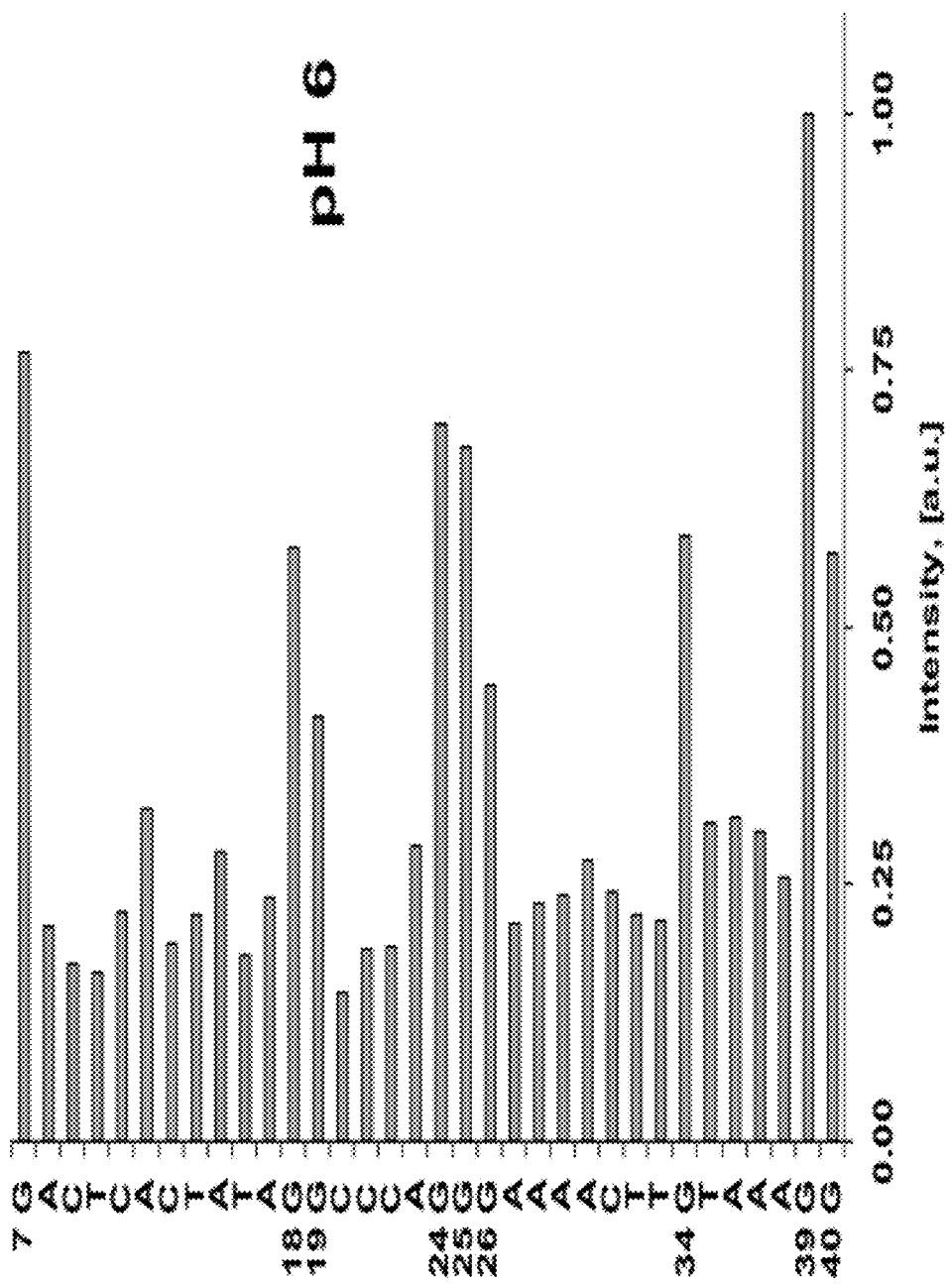
FIG. 20 includes three histograms showing the quantified cleavage data in the DNA 54-mer at the different pH values; the DNA oligomer (1 µM) was irradiated in the presence of compound 4 (10 µM) in 20 mM sodium phosphate buffer.
Figure 20:
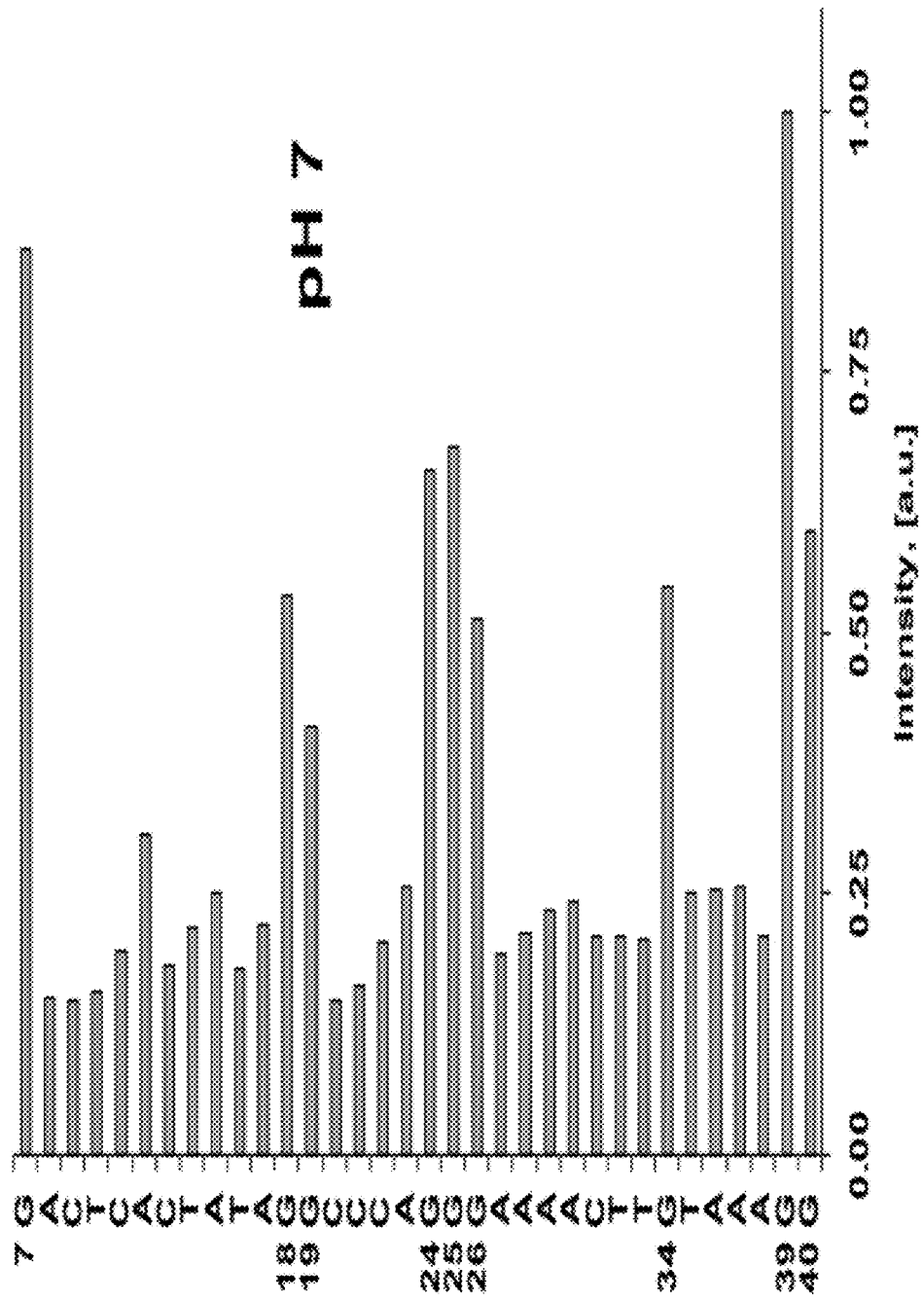
Figure 20:
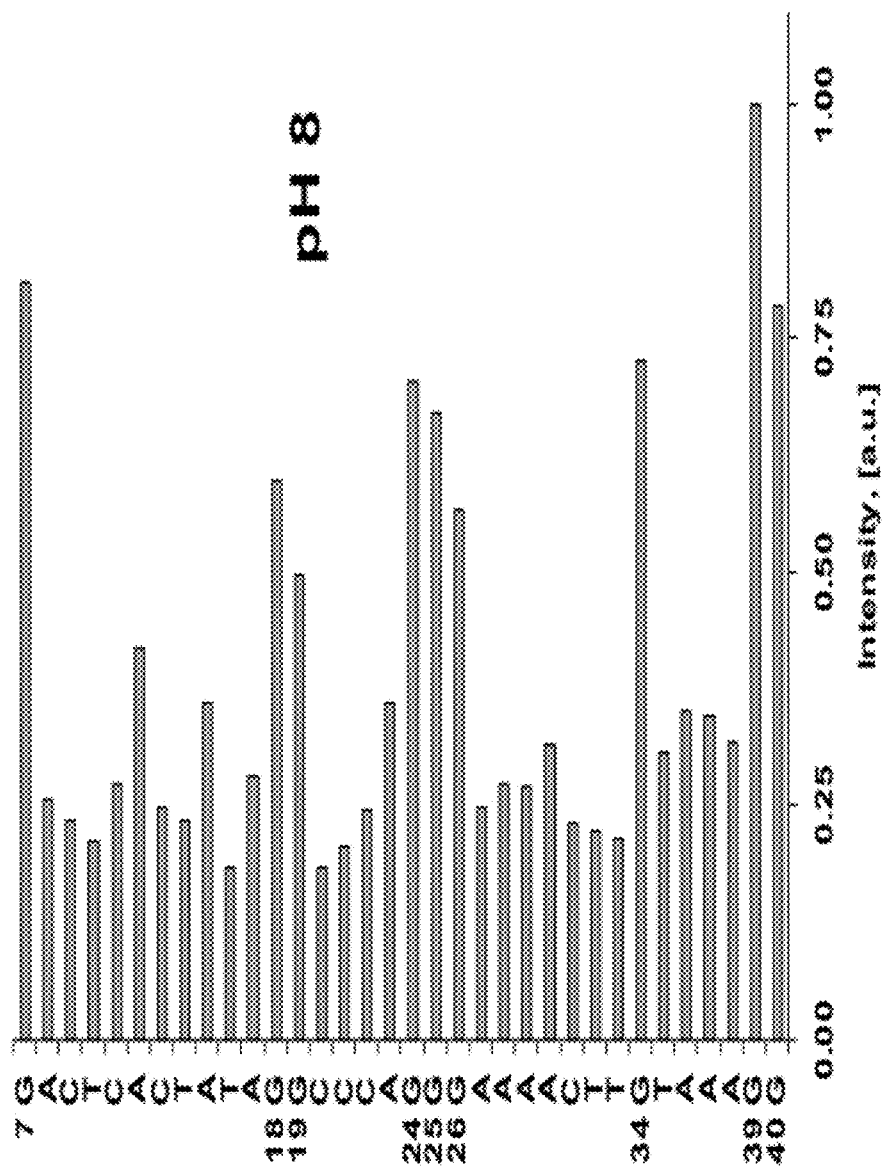

We further tested whether sequence selectivity depends on the pH using 5'-$^{32}$P-labeled ds-DNA oligomer (5' TAA TAC $G_7$AC TCA CTA $TAG_{18}$ $G_{19}$CC $CAG_{24}$ $G_{25}G_{26}$A AAA CTT $G_{34}$TA $AAG_{39}$ $G_{40}$TC TAC CTA TCT *ATT, paired with a complementary counterstrand; $^{32}$P-label indicated by asterisk, FIG. 20. This model 54-mer incorporates several isolated guanine (G) nucleotides as well as GG diads and GGG triads. Interestingly, for this sequence we did not observe dramatic differences in the selectivity of cleavage at the different pH values. This observation along with the remarkably well-defined patterns for the formation of linear DNA in plasmid experiments suggest that the larger plasmid DNA may contain certain sequences which provide a much better binding environment to the lysine-conjugates and affected much stronger by the pH-changes.

In order to get further insight in the mechanism of the DNA cleavage by the conjugates, we used the plasmid relaxation assays for the cleavage with enediyne conjugate 1 and TFP-acetylene conjugate 4 in the presence of hydroxyl radical (glycerol, DMSO) and singlet oxygen ($NaN_3$) scavengers. The results are summarized in FIG. 21.

For compound 1, a small protecting effect of the hydroxyl radical scavengers is observed at all pH values. The protecting effect seems to be slightly lower at pH 6 then at the higher pH values. It is noteworthy, however, that the ds cleavage at pH 6 is not affected by any of the additives. Singlet oxygen scavengers show no effect upon the efficiency of DNA damage by compound 1 at pH 6 and 7.

Remarkably, neither of the additives is able to protect DNA from damage by acetylene-lysine conjugate 4 at pH 6. Some protecting effect is observed only at the higher pH. These results clearly indicate that reactive oxygen species are not involved in the mechanism of DNA cleavage at the lower pH, perhaps due to the tighter binding under these conditions. This observation provides additional support for a direct mechanism of DNA damage such as base pair alkylation. From a practical perspective, this is valuable not only because many solid tumors are hypoxic but also because cleavage which does not depend on diffusing species is more localized and efficient.

Figure 22:
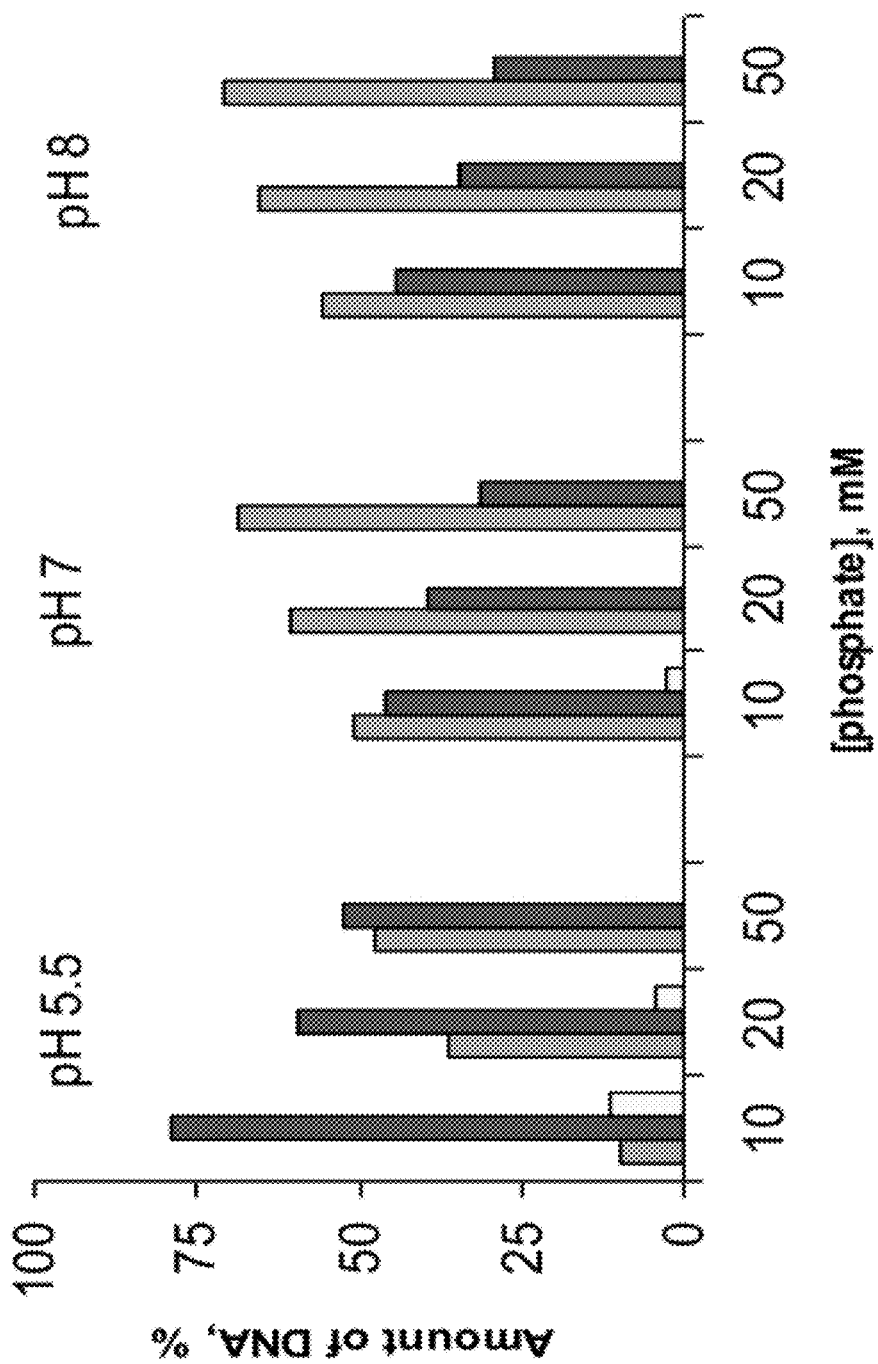
FIG. 22 shows quantified cleavage data of pBR 322 plasmid (30 µM/bp) relaxation assays of compound 4 (10 µM) at different concentrations of phosphate buffer at pH 5.5, 7 and 8; color coding: light blue—Form I, dark purple—Form II, light yellow—Form III.

The final insight on the nature of lysine conjugates/DNA interaction came from the effect of ionic strength on the efficiency of DNA cleavage (FIG. 22). Increasing concentration of phosphate buffer from 10 mM to 50 mM decreases the total DNA cleavage activity of compound 4 by 48%, 40%, 34% at pH 5.5, 7 and 8, respectively. This result suggests that the electrostatic interaction between the positive charges of ammonium group of compound 4 and the negative charges of DNA backbone is an important factor for the cleavage. Again, this observation indicates relatively close binding between the DNA-cleaver and its target which should be particularly important for the DNA-cleavage mechanisms based on alkylation and hydrogen abstraction. In contrast, the cleavage at pH 8 has greater contributions from processes not affected strongly by the ionic strength, such as the generation of diffusing reactive oxygen species.

Cancer Cell Proliferation Assays.

Figure 23:
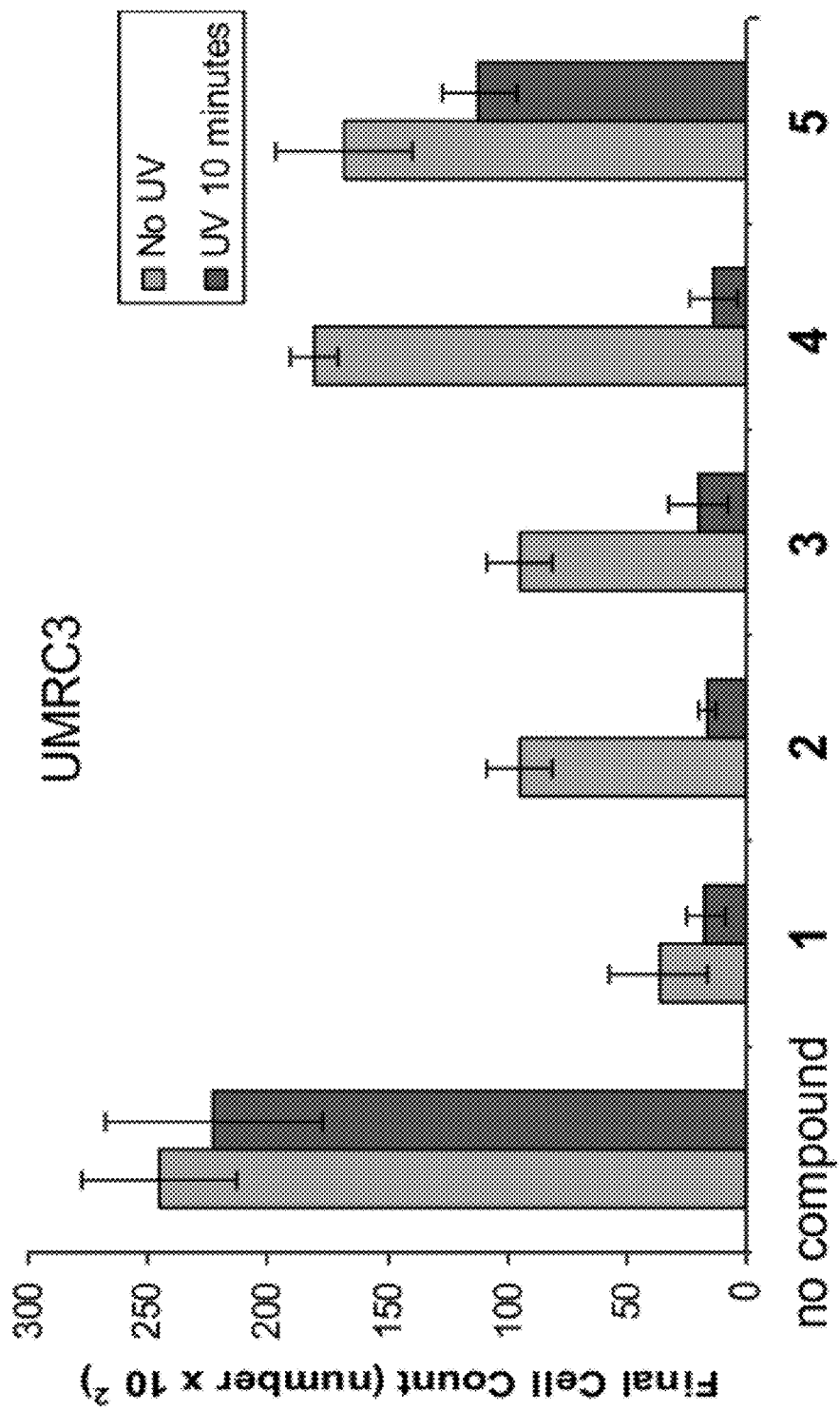
FIG. 23 provides the results of cell proliferation assays using three different RCC cell lines: (a) UMRC3, (b) UMRC6 and (c) 786-O, and compounds I-5; RCC cells were resuspended in media and treated with UV radiation (350 nm) for 10 minutes with and without indicated compounds; control cells were exposed to the indicated compound 1-5 at final concentration of 10 µM; cell numbers determined after 72 hours as described in the SI Section.
Figure 23:
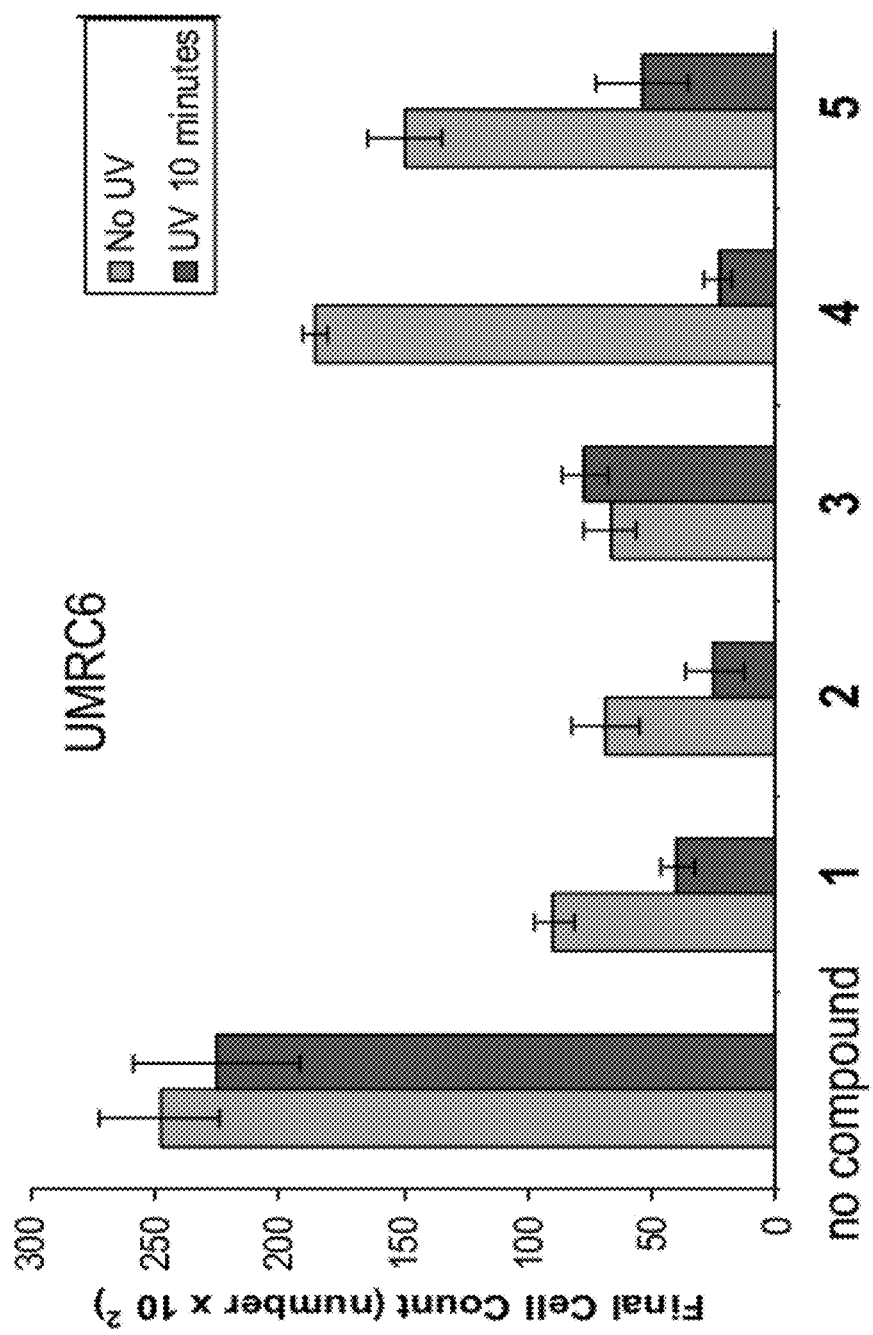
Figure 23:
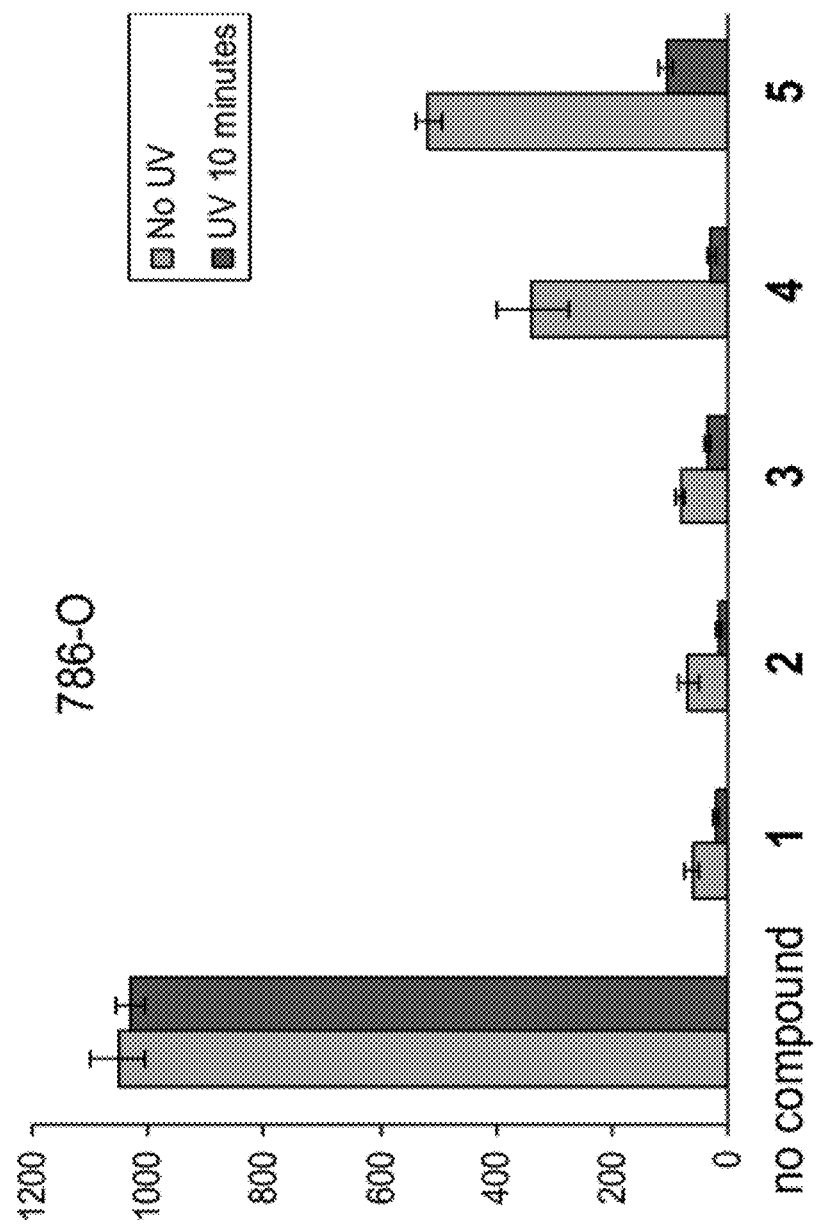
Figure 24:
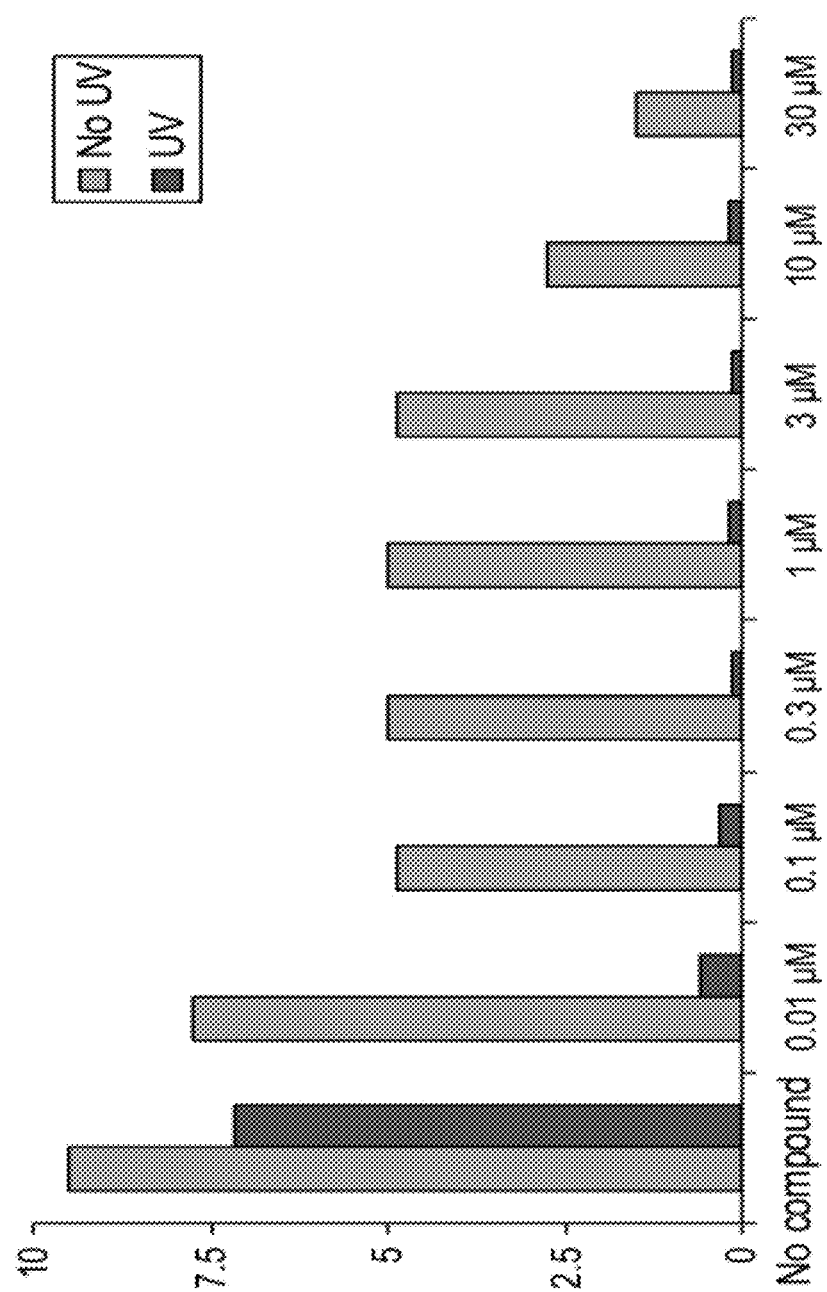
FIG. 24 depicts the results of LNCap cell proliferation assays with varying concentration of compound 4; the cells were exposed to UV for 10 minutes; cells were counted 48 hours after the exposure.

The ability of compounds 1-5 to inhibit cell proliferation in three human clear cell renal cell carcinoma (RCC) cell lines was tested in the dark and under photoactivation (FIG. 23). No difference was detected in the control experiments between cells not exposed to UV versus those that were exposed to UV at 350 nm for 10 minutes in any of the three RCC cell lines tested (FIG. 23 A, B & C; first two columns). On the other hand, all five compounds inhibited growth in each of the three cell lines but to varying degrees both in the dark and after UV radiation. Although UV treatment always enhanced the ability of conjugates 1-3 to inhibit cell proliferation, these compounds had strong growth inhibitory activity even without photoactivation in all three cell lines (FIG. 23 A-C) with a range of 62-94% inhibition. On the other hand, compounds 4 and 5 were considerably less cytotoxic in the dark. Compound 4 seems to be an especially promising lead for the future development of anticancer agents because the decrease of cell numbers in control UV-irradiated cells as compared to control without UV-irradiation in UMRC3 and UMRC6 cells was not statistically significant (FIG. 23 A, B) but, when exposed to UV radiation and the conjugate, these cells displayed mortality of 94% in UMRC3 and 90% in UMRC6 cells.

Encouraged by these results, we studied the concentration effects of compound 4 at the proliferation of in LNCap human prostate adenocarcinoma cells in the dark and under photoactivation conditions in more detail. Remarkably, even at the low 10 nM concentration, this system destroys more than 90% of LNCap cells in one treatment whereas almost no toxicity is observed without light.

CONCLUSION

Hybrid molecules which combine pH-regulated lysine moiety with a powerful DNA-photocleaver display dramatically increased DNA-cleaving reactivity at the lower pH. Synergistic effects associated with the protonation of the α-amino group, such as pH-dependent changes in photophysical properties as well as in pH-dependent DNA-binding (FIG. 11), account for the increase in reactivity. Deactivation of the internal quenching pathway (FIG. 11a) increases the lifetime of reactive singlet state while transformation of the conjugates into their dicationic form (FIG. 11b) changes their binding mode with the polyanionic backbone of DNA.

Remarkably, the observed switch from negligible to record-breaking efficiency of the most therapeutically useful form of DNA cleavage (the ds DNA cleavage) occurs upon a relatively small change in the pH which can be used to differentiate healthy cells from hypoxic cancer tissues. The amplification of DNA-cleaving activity seems to be quite general and manifests itself for DNA-cleaving agents which bind DNA in different way and attack DNA through different chemical mechanisms. Cleavage at the lower pH for the conjugate 4 is not affected by the reactive oxygen species scavengers, suggesting possible value of this DNA-cleaver for targeting hypoxic cancer tissues. Cancer cell proliferation assays further confirm remarkable potential of these molecules for the development of light-activated anticancer agents.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

Figure 5:
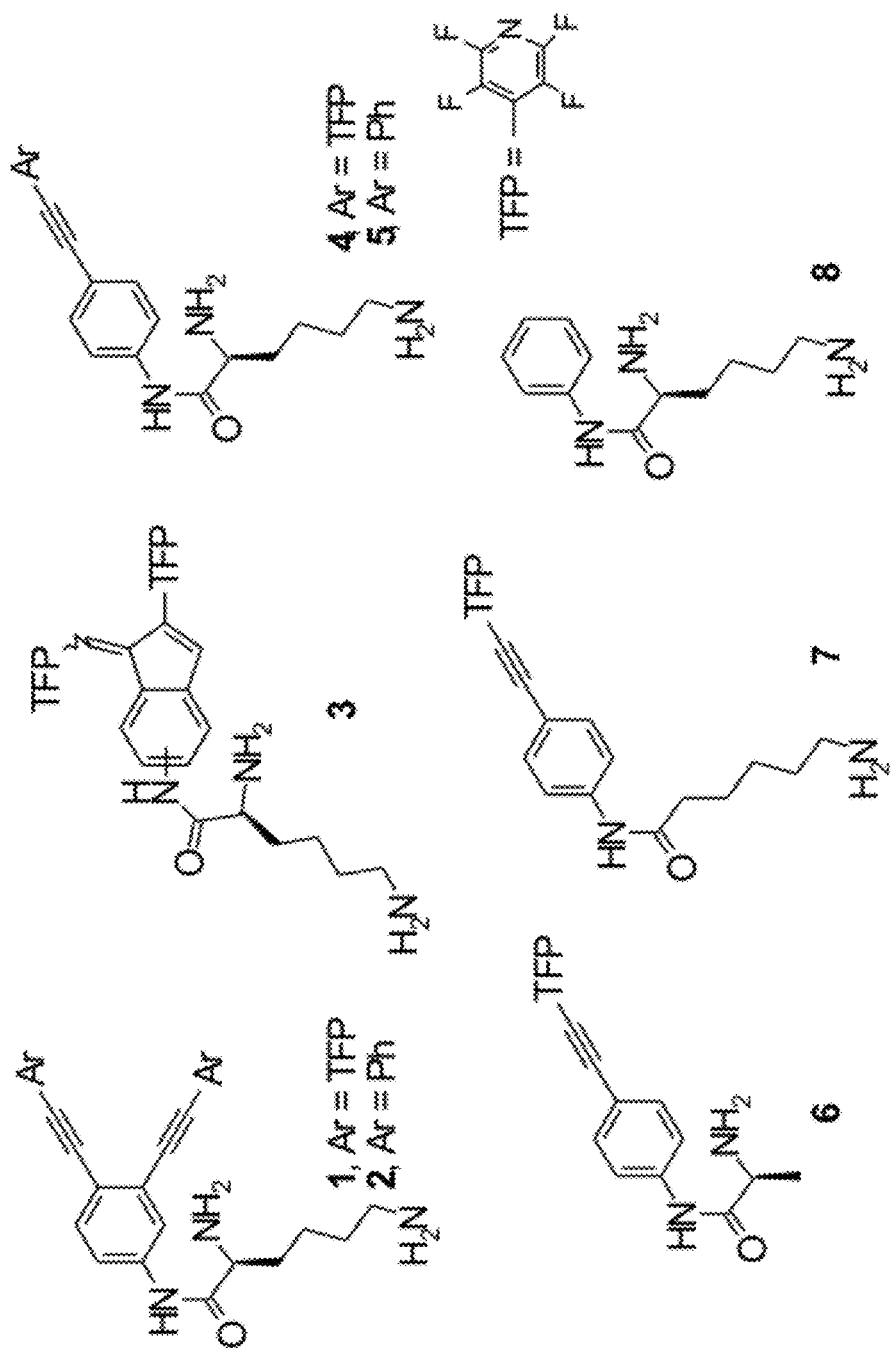
FIG. 5 shows the structures of lysine conjugates 1-5 and related control compounds 6-8.

That which is claimed:

1. A lysine conjugate selected from the group consisting of compounds having a structure according to formula 1, formula 2, formula 3, formula 4 and formula 5 as shown in FIG. 5.

2. A method for producing double-strand cleavage in DNA, the method comprising:
    contacting a double-stranded DNA molecule at a pH between approximately 5.5 and 8 with the lysine conjugate of claim 1; and
    irradiating with ultraviolet light.

3. A method of increasing efficiency of double-stranded DNA cleavage, the method comprising:
    contacting a double-stranded DNA molecule with a lysine conjugate selected from the group consisting of formula 1, formula 2, formula 3, formula 4 and formula 5, in a physiologically acidic environment; and
    irradiating the contacted DNA with ultraviolet light.

4. The method of claim 3, wherein the physiologically acidic environment comprises approximately pH 5.5 to 7.

5. The method of claim 3, wherein irradiation with ultraviolet light is at approximately 350 nm.

6. A method of inhibiting a mammalian cell, the method comprising:
    contacting the cell with the lysine conjugate of claim 1;
    binding the lysine conjugate with the cell's double-stranded DNA at a pH between approximately 5.5 and 8; and
    irradiating the cell with ultraviolet light to photochemically activate the bound lysine conjugate to cause a double-stranded cleavage in said DNA.

7. The method of claim 6 wherein the mammalian cell is a human cell.

8. The method of claim 6, wherein the mammalian cell is a cancer cell.

9. The method of claim 6, wherein the mammalian cell is a human cancer cell.

10. A method of inhibiting a human cancer cell, the method comprising:
    contacting the cell's double-stranded DNA with a lysine conjugate having a structure selected from formulas 1-5; and
    irradiating the cell with ultraviolet light.

11. The method of claim 10, wherein contacting is effected at between approximately pH 5.5 and 8.

12. The method of claim 10, wherein irradiating is conducted with ultraviolet light having a wavelength of approximately 350 nm.

13. A method of controlling electron transfer from DNA to a photochemical cleaver compound, the method comprising:
    functionalizing the photochemical cleaver compound by attaching thereto a pH-sensitive functional chain or ring having one or more amino groups of sufficient basicity;
    protonating the one or more amino groups of the photochemical cleaver at a physiologically acidic pH;
    binding the protonated photochemical cleaver to double-stranded DNA;
    irradiating the bound protonated photochemical cleaver with ultraviolet light;
    whereby one or more electrons are transferred from the DNA to the bound protonated photochemical cleaver to thereby cause damage to the DNA.

14. The method of claim 13, wherein the functionalized photochemical cleaver compound is a compound according to claim 1.

15. The method of claim 13, wherein binding comprises having the functionalized photocleaver compound positioned adjacent a single-strand nick in the DNA.

16. The method of claim 13, wherein the physiologically acid pH comprises from approximately pH 5.5 to approximately pH 7.

17. The method of claim 13, wherein the DNA is intracellular.

* * * * *